(12) United States Patent
Nyce

(10) Patent No.: US 6,825,174 B2
(45) Date of Patent: Nov. 30, 2004

(54) COMPOSITION, FORMULATIONS & METHOD FOR PREVENTION & TREATMENT OF DISEASES AND CONDITIONS ASSOCIATED WITH BRONCHOCONSTRICTION, ALLERGY(IES) & INFLAMMATION

(75) Inventor: Jonathan W. Nyce, Titusville, NJ (US)

(73) Assignee: East Carolina University, Greenville, NC (US)

( * ) Notice: Subject to any disclaimer, the term of this patent is extended or adjusted under 35 U.S.C. 154(b) by 258 days.

(21) Appl. No.: 09/093,972

(22) Filed: Jun. 9, 1998

(65) Prior Publication Data

US 2003/0087845 A1 May 8, 2003

Related U.S. Application Data

(63) Continuation-in-part of application No. 09/016,464, filed on Jan. 30, 1998, and a continuation-in-part of application No. 08/757,024, filed on Nov. 26, 1996, now Pat. No. 6,025,339, and a continuation-in-part of application No. 08/472,527, filed on Jun. 7, 1995, now Pat. No. 6,040,296, and a continuation-in-part of application No. 08/474,497, filed on Jun. 7, 1995, now Pat. No. 5,994,315, said application No. 08/757,024, is a continuation-in-part of application No. 08/472,527, filed on Jun. 7, 1995, now Pat. No. 6,040,296.

(51) Int. Cl.⁷ ...................... A01N 43/04; C12N 15/87; A61K 31/07; C07H 21/04

(52) U.S. Cl. ........................ 514/44; 435/6; 435/325; 435/375; 435/455; 536/24.3; 536/24.31; 536/24.33; 536/24.5

(58) Field of Search ...................... 536/23.1, 24.3, 536/24.31, 24.5; 514/44; 435/91.1, 6, 375, 325, 69.1, 320.1

(56) References Cited

U.S. PATENT DOCUMENTS

| 5,320,962 A | * | 6/1994 | Stiles et al. ............... 435/252.3 |
| 5,514,788 A | * | 5/1996 | Bennett et al. ............ 536/23.1 |
| 5,733,572 A | | 3/1998 | Unger et al. |
| 5,994,315 A | * | 11/1999 | Nyce et al. ................ 514/44 |
| 6,207,646 B1 | | 3/2001 | Krieg et al. |

FOREIGN PATENT DOCUMENTS

| WO | 9310820 | 6/1993 | |
| WO | 9312756 | 7/1993 | |
| WO | 9402605 | 2/1994 | |
| WO | 9640162 | 12/1996 | |
| WO | WO9640162 A1 | * 12/1996 | ......... A61K/31/70 |
| WO | WO9640266 A1 | * 12/1996 | ......... A61K/48/00 |
| WO | 9640266 | 12/1996 | |
| WO | 9811211 | 3/1998 | |
| WO | 9823294 | 6/1998 | |
| WO | 9960166 | 11/1999 | |
| WO | 0009525 | 2/2000 | |

OTHER PUBLICATIONS

Bracket et al., Activities of caffeine, theophyline, and enprofyline analogs as tracheal relaxants, Biochem. Pharmacol. (1990), 39(12), 1897–904, 1990.*

Rahman, M. Sayeedur, et al., "Nebularine (9–2'–deoxy–beta–D–ribofuranosylpurine) has the template characteristics of adenosine in vivo and in vitro", Mutation Research, vol. 377, No. 2, 1997, pp. 263–268.

Loakes, D. et al., "5–Nitroindole as an universal base analogue", Nucleic Acids Research, vol. 22, No. 20, 1994, pp. 4039–4043.

Ohtsuka, E. et al., "An alternative approach to deoxyoligonucleotides as hybridization probes by insertion of deoxyinosine at ambiguous codon positions", Journal of Biological Chemistry, vol. 260, No. 5, Mar. 10, 1985, pp. 2605–2608.

Nichols, R. et al., "A universal nucleoside for use at ambiguous sites in DNA primers",Nature, vol. 369, No. 6480, Jun. 9, 1994, pp. 492–493.

Metzger W. James et al., "Oligonucleotide therapy of allergic asthma", Journal of Allergy and Clinical Immunology, vol. 104, No. 2 part 1, Aug. 1999, pp. 260–266.

Nyce, J.W., "Respirable Antisense Oligonucleotides as Novel Therapeutic Agents for Asthma and Other Pulmonary Diseases", Exp. Opin. Invest. Drugs, 6(9): 1–7, (1997).

(List continued on next page.)

Primary Examiner—John L. LeGuyader
Assistant Examiner—Janet L. Epps-Ford
(74) Attorney, Agent, or Firm—Albert P. Halluin; Robin C. Chiang; Howrey Simon Arnold & White, LLP

(57) ABSTRACT

A pharmaceutical composition effective for preventing and alleviating bronchoconstriction, lung allergy(ies) and inflammation comprises a surfactant and an oligonucleotide anti-sense to an adenosine receptor gene, flanking regions or regions bridging the intro/exon borders, analogues which bind thymidine but have low adenosine content or exhibit lower or no adenosine receptor agonist activity, or antisense to the corresponding mRNA, combinations, sales or mixtures thereof, and a carrier, and optionally other therapeutic agents and formulation products. The composition is formulated for administration by a multiplicity of routes, and finds applications in the prevention and treatment of asthma, kidney damage or failure, ARDS, pulmonary vasoconstriction, inflammation, allergies, impeded respiration, respiratory distress syndrome, pain, cystic fibrosis, pulmonary hypertension, pulmonary vasoconstriction, emphysema, chronic obstructive pulmonary disease (COPD), and cancer, to counter the renal damage and failure associated with ischemic conditions and the administration of certain drugs and radio active diagnostic and therapeutic agents, as well as a joint therapy with the administration of adenosine and adenosine-like agents in the treatment of arrhythmias such as SVT and in cardiovascular function tests (stress tests). The present agent(s) is (are) also suitable for administration before, during and after other treatments, including radiation, chemotherapy, antibody therapy, phototherapy and cancer, and other types of surgery.

16 Claims, 4 Drawing Sheets

OTHER PUBLICATIONS

Nyce, J.W. et al., "DNA Antisense Therapy for Asthma in an Animal Model", *Nature*, 385(20): 721–725, (1997).

Akhter, S. et al., "In Vivo Studies with Antisense Oligonucleotides", *Trends in Pharmacol. Sciences*, 18: 12–18, (1997).

Webb, A. et al., "BCL–2 Antisense Therapy in Patients with Non–Hidgkin Lymphoma", *Lancet*, 349(9059): 1137–41, (1997).

Yazaki, T. et al., "Treatment of Glioblastoma U–87 by Systemic Administration of an Antisense Protein Kinase C–Alpha Phosphorthioate Oligodeoxynucleotide", *Molecular Pharmacol.*, 50(2): 236–242, (1996).

Farmer, S.G. et al., "Adenosine Receptor–mediated Contraction and Relaxation of Guinea–pig Isolated Tracheal Smooth Muscle: Effects of Adenosine Antagonists", *Br. J. Pharmacol.*, 95: 371–378 (1988).

Marquardt, D.L. et al., "Aminophylline Exposure Alters Mouse Bone Marrow–derived Mast Cell Adenosine Responsiveness", *J. Allergy Clin Immunol.* 78: 462–469, (1986).

Stull, R.A. et al., "Predicting antisense oligonucleotide inhibitory efficacy: a computational approach using histograms and thermodynamic indices", Nucleic Acids Research, 20(13): 3501–3508 (1992).

Monia, B.P. et al., "Selective Inhibition of Mutant Ha–ras mRNA Expression by Antisense Oligonucleotides", J. Biol. Chem., vol. 2G7 No. 28, Issue of Oct. 5, 19954–19962 (1992).

Pasternak, Gavril W., "Molecular Neuropharmacology", The Scientist, 10(8):14 (1996).

Akhtar, S. et al., "In vivo studies with antisense oligonucleotides", Trends in Pharmacological Science, Current Techniques, 18:12–18, (1997).

Nyce, J.W., "Antisense oligonucleotides as emerging drugs", Emerging Drugs, 3:365–375, (1998).

SIGMA: *Alphabetical List of Compounds, Material Safety Data Sheet and Polypropylene*, (2000).

National Library of Medicine: IGM Full Record Screen: Hill et al., PNASUSA, Apr. 14, 1998; 95(8):4258–63.

National Library of Medicine: IGM Full Record Screen: Medical Research Council et al.., Nucleic Acids Res Oct. 11, 1994; 22(20):4039–43.

* cited by examiner

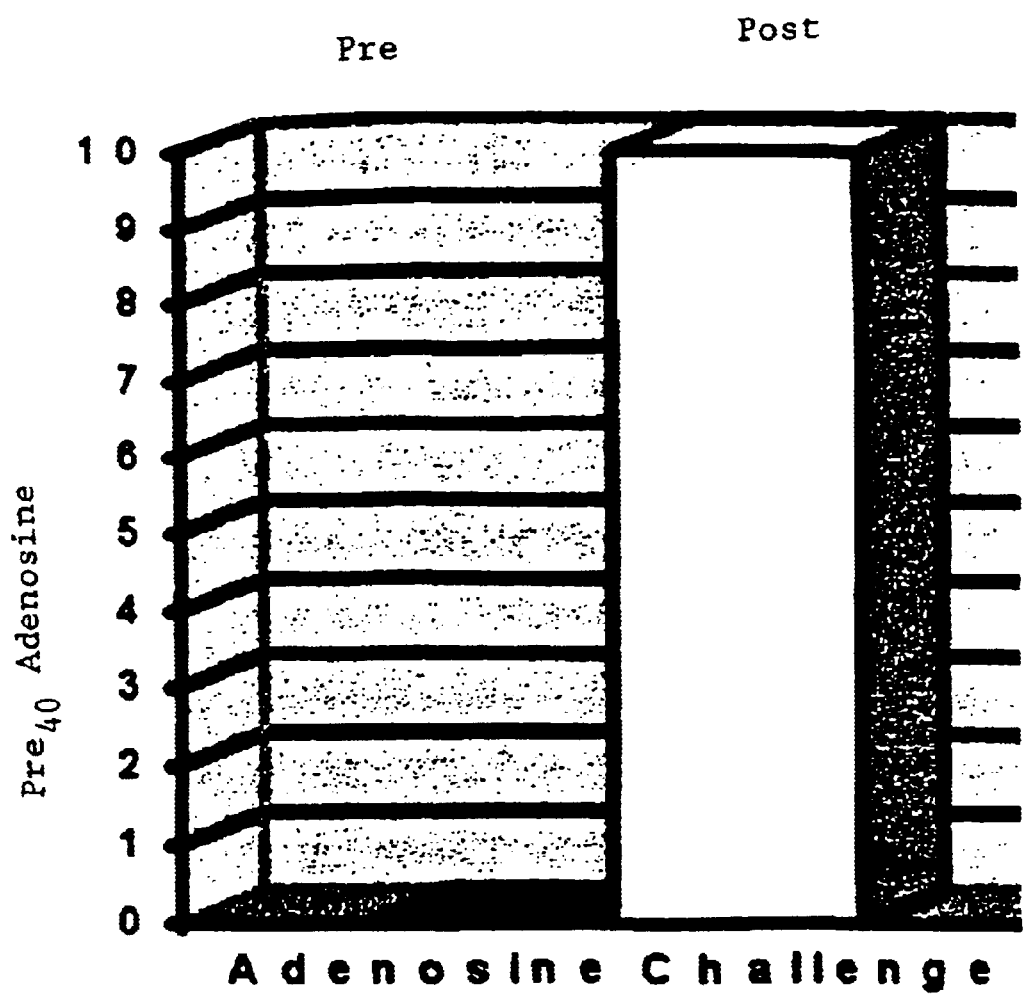
FIGURE 3A  Monkey 1

COMPOSITION, FORMULATIONS & METHOD FOR PREVENTION & TREATMENT OF DISEASES AND CONDITIONS ASSOCIATED WITH BRONCHOCONSTRICTION, ALLERGY(IES) & INFLAMMATION

RELATED APPLICATIONS

This application is a continuation-in-part of U.S. patent application Ser. No. 08/472,527, filed Jun. 7, 1995, CPA filed Feb. 27, 1998, now U.S. Pat. No. 6,040,296; a continuation-in-part of U.S. patent application Ser. No. 08/757,024, filed Nov. 26, 1996, by Jonathan W. Nyce, now U.S. Pat. No. 6,025,339, which is a continuation-in-part of U.S. patent application Ser. No. 08/472,527, filed Jun. 7, 1995; and a continuation-in-part of U.S. patent application Ser. Nos. 08/474,497 filed Jun. 7, 1995, now U.S. Pat. No. 5,994,315, and 09/016,464, filed Jan. 30, 1998, by Jonathan W. Nyce and W. James Metzger, CPA filed Jun. 3, 1998, now pending.

This invention was made at least partially with United States Government support under grant RO1CA47217-06 from National Cancer Institute. The Government may have certain rights to this invention.

BACKGROUND OF THE INVENTION

1. Field of the Invention

This invention relates to compositions and formulations of oligonucleotides and surfactants, which are highly effective for the prevention and treatment of diseases and conditions associated with difficult breathing, bronchoconstriction, impeded airways, allergy(ies) and inflammation of the lungs.

2. Description of the Background

Adenosine $A_1$-mediated diseases and conditions, such as asthma and Acute Respiratory Distress Syndrome (ARDS), among others, are common diseases in industrialized countries, and in the United States alone account for extremely high health care costs. These diseases or conditions have recently been increasing for an alarming rate, both in terms of prevalence and mortality. Occupational asthma is predicted to be the preeminent occupational lung disease in the next decade. In many of these, the underlying causes remain poorly understood.

Adenosine, a natural nucleoside, may constitute an important natural mediator of bronchial asthma and ARDS. The potential role of adenosine in these diseases or conditions is supported by experimental findings that, for example and in contrast to normal individuals, asthmatics respond to aerosolized adenosine with marked bronchoconstriction. Similarly, asthmatic rabbits produced using the dust mite allergic rabbit model of human asthma also were shown to respond to aerosolized adenosine with marked bronchoconstriction, while non-asthmatic rabbits showed no response. Recent work using this model system has suggested that adenosine-mediated bronchoconstriction in asthma is mediated through the stimulation of the adenosine $A_1$ receptor. Other experimental data suggest the possibility that adenosine receptors may also be involved in allergic and inflammatory responses.

Adenosine receptor antagonists, such as theophylline, are known to counter adenosine-mediated bronchoconstriction in asthmatic rabbits. Pre-treatment with another adenosine $A_1$-specific receptor antagonist, 8-cyclopentyl-1,3-dipropylxanthine (DPCPX), also inhibited adenosine-mediated bronchoconstriction and bronchial hyper-responsiveness in an allergic rabbit model. The therapeutic potential, however, of currently available adenosine $A_1$ receptor-specific antagonists is drastically limited by their toxicity. Theophylline, for example, although widely used in the treatment of asthma, may result in frequent and significant toxicity because of its narrow therapeutic dose range.

The availability of a novel strategy to prevent and/or counter adenosine receptor-associated effects of disorders and conditions associated with symptoms such as pulmonary bronchoconstriction, impeded respiration. Inflammation and allergy(ies), among others, of great practical importance. Such technology is clearly applicable to the treatment of ailments including Acute Respiratory Disorder Syndrome (ARDS), asthma, respiratory distress syndrome, pain, cystic fibrosis, pulmonary hypertension, pulmonary vasoconstriction, emphysema, chronic obstructive pulmonary disease (COPD), and cancers such as leukemias, lymphomas, carcinomas, and the like, including colon cancer, breast cancer, lung cancer, pancreatic cancer, hepatocellular carcinoma, kidney cancer, melanoma, hepatic metastases, etc., as well as all types of cancers which may metastasize or have metastasized to the lung(s), including breast and prostate cancer would clearly find an immediate therapeutic application. Similarly, a composition and method which are suitable for administration before, during and after other treatments, included radiation, chemotherapy, antibody therapy, phototherapy an cancer, and other types of surgery, and that may be effectively administered preventatively, prophylactically or therapeutically, and in conjunction with other therapies, or by itself for conditions without known therapies or as a substitute for therapies that have significant negative side effects is also of immediate clinical application.

SUMMARY OF THE INVENTION

The present invention relates to a pharmaceutical composition effective to alleviate bronchoconstriction, allergy and/or inflammation, comprising a surfactant, and an anti-adenosine $A_1$, $A_{2b}$, or $A_3$ receptor or anti-adenosine $A_{2a}$ receptor oligonucleotide exhibiting at least some adenosine $A_1$, $A_{2b}$, or $A_3$ receptor inhibitory activity, analogues thereof which bind to thymidine but evidence either reduced adenosine content or reduced adenosine receptor activating activity, combinations thereof, physiologically acceptable salts thereof or mixtures thereof. The composition of this invention may be formulated for administration by various different routes, such as topical and systemic, e.g. oral, parenteral, inhalable, and the like, and are generally administered in amounts which prevent or reduce adenosine receptor associated side effects such as bronchoconstriction, allergy(ies), inflammation and airway obstruction, among others. The present compositions and formulations, thus, are suitable for the prevention and alleviation of adenosine receptor associated bronchoconstriction, allergy and/or inflammation and, therefore, in the treatment of Acute Respiratory Disorder Syndrome (ARDS), asthma, side effects associated with adenosine administration in SupraVentricular Tachycardia (SVT) and in stress tests to hyper-sensitized individuals, ischemia, renal damage or failure induced by certain drugs, respiratory distress syndrome, pain, cystic fibrosis, pulmonary hypertension, pulmonary vasoconstriction, emphysema, chronic obstructive pulmonary disease (COPD), cancers such as leukemias, lymphomas, carcinmos, and the like, including colon cancer, breast cancer, lung cancer, pancreatic cancer, hepatocellular carcinoma, kidney cancer, melanoma, hepatic metastases, etc., as well as all types of cancers which may metastasize or have metastasized to the lung(s), including breast and prostate cancer, among others. The present technology is also applicable in conjunction with other procedures and/ other therapies, including other therapeutic agents such as antibody therapy and chemotherapy, among others, radiation, phototherapy, and cancer and other types of surgery, and is effectively administered preventatively, prophylactically or therapeutically.

BRIEF DESCRIPTION OF THE DRAWINGS

FIGS. 3a and 3b illustrate the response of two hyper-responsive monkeys (ascaris sensitive) to a challenge with inhaled adenosine. The right hand bar represents the $PC_{40}$ adenosine after administration of the Oligo I, whereas the left hand bar represents the $PC_{40}$ adenosine value prior to treatment with the Oligo I. The $PC_{40}$ adenosine, represented in the Y axis, is the amount of adenosine in mg that causes a 40% decrease in dynamic compliance in hyper-responsive airways.

FIG. 3a represents the experimental results obtained without and with pre-treatment of a first monkeys with a phosphorothioate agent of the invention (anti-sense oligo; I; SEQ. ID NO:1), prior to administrative of adenosine.

FIG. 3b represents the experimental results obtained without and with pre-treatment of a second monkey with a phosphorothioate agent of this invention (anti-sense oligo I; SEQ. ID NO:1), prior to administration of adenosine.

DETAILED DESCRIPTION OF THE PREFERRED EMBODIMENTS

Figure 1:
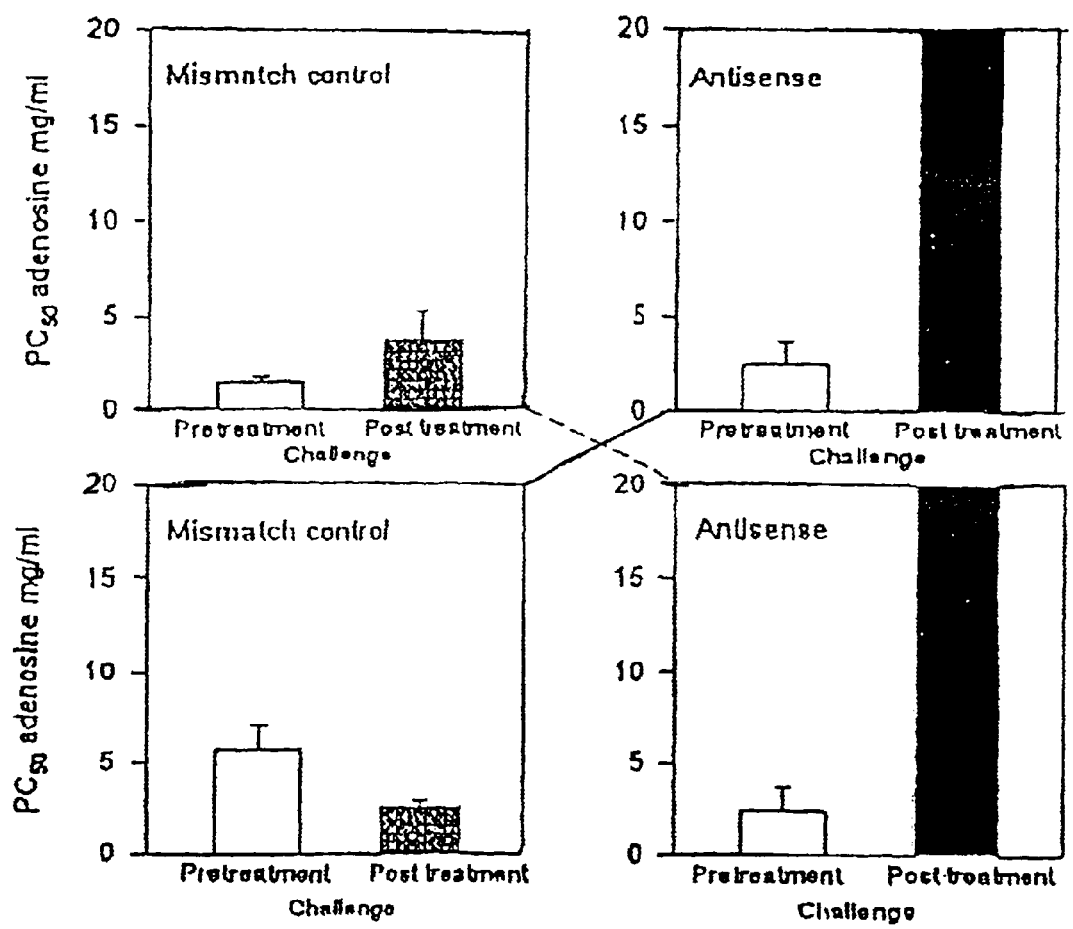
FIG. 1 illustrates the effects of $A_1$ adenosine receptor anti-sense oligonucleotides and mismatch control anti-sense oligonucleotides on the dynamic compliance of the bronchial airway in a rabbit model. The two stars represent significant difference at $p<0.01$, Student's t-test.

This invention arose from a desire by the inventor to improve on his own prior technology for the treatment of acute bronchoconstriction allergy and/or inflammation associated with various diseases and conditions, including Acute Respiratory Distress Syndrome (ARDS), asthma, adenosine administration e.g. in the treatment of Supra Ventricular Tachycardia (SVT) and other arrhythmias, and in stress tests to hyper-sensitized individuals, ischemia, renal damage of failure induced by certain drugs, infantile respiratory distress syndrome, pain cystic fibrosis, pulmonary hypertension, pulmonary vasoconstriction, emphysema, chronic obstructive pulmonary disease (COPD), and cancers such as leukemias, lymphomas, carcinomas, and the like, including colon cancer, breast cancer, lung cancer, pancreatic cancer, hepatocellular carcinoma, kidney cancer, melanoma, hepatic metastases, etc., as well as all types of cancers which may metastisize or have metastasized to the lung(s), including breast and prostate cancer. The inventor, in addition, wanted to provide a treatment which would improve the outcome and life stile of patients undergoing other procedures or being administered other therapies, including antibody therapy, chemotherapy, radiation, phototherapy, and surgery e.g. cancer surgery, and that could be effectively administered preventatively, prophylactically or therapeutically.

He succeeded in this endeavor and is providing in this patent novel and improved compositions, formulations and methods which afford greatly improved results when compared with previously known treatments for preventing and alleviating bronchoconstriction, allergy(ies), inflammation, breathing difficulties and blockage of airways. The nucleic acid and surfactant components of the bare bone composition of the invention may be formulated alone with a carrier, or with other therapeutic agents and formulation agents as is known in the art. The compositions of this invention, thus, may be incorporated into a variety of formulations for systemic and topical administration.

In the past, anti-sense oligonucleotides received considerable theoretical consideration as being potentially useful as pharmacologic agents for the treatment of human disease. R. Wagner, Nature 372: 333–335 (1994). However, it has been difficult to actually apply these molecules to alleviating and curing human diseases. Once important consideration in the pharmacologic application of these molecules has been the failure of various routes of administration to deliver the compounds to its target while avoiding invading the circulation and, therefore, other untargeted tissues which, thus, produces a plethora of side effects. Most in vivo experiments utilizing anti-sense oligonucleotides involved a direct application of the oligo to limited regions of the brain. See, C. Wahlestedt, Trends in Pharmacol. Sci. 15: 42–46 (1994); J. Lai et al., Neuroreport 5: 1049–1052 (1994); K. Standifer et al., Neuron 12: 805–810 (1994); A. Akabayashi et al., Brain Res. 21: 55–61 (1994). Others applied them into the spinal fluid See, e.g. L. Tseng et al., European J. Pharmacol. 258: R1–3 (1994); R. Raffa et al., European J. Pharmacol. 258: R5–7 (1994); F. Gillardon et al., European J. Neurosci. 6: 880–884 (1994). Such applications, clearly, have no practical clinical utility due to their invasive nature. Thus, the systemic administration of anti-sense oligonucleotides poses significant problems with respect to their pharmacologic application, not the least of which is the difficulty in selectively targeting disease-involved tissues.

The systemic administration of anti-sense oligonucleotides also poses significant problems with respect to their pharmacologic application, not the least of which is difficult in selectively targeting disease-involved tissues. The respiratory system, and in particular the lung, as the ultimate port of entry into the organism, however, is an excellent route of administration for anti-sense oligonucleotides. This is so not only for the treatment of lung disease, but also when utilizing the lung as a means for delivery, particularly because of its non-invasive and tissue-specific nature. Thus, local delivery of antisense oligonucleotides directly to the target tissue enables the therapeutic use of these compounds. Formivirsen (ISIS 2302) is an example of a local drug delivery into the eye to treat cytomegalovirus (CMV) retinitis, for which a new drug application has been filed by ISIS. The administration of a drug through the lung offers the further advantage that inhalation is non-invasive whereas direct injection in the vitreous of the eye is invasive.

The composition and formulations of this invention have been shown to have an exceedingly high efficacy for preventing and treating a disease or condition associated with bronchoconstriction, difficult breathing, impeded and obstructed lung always, allergy(ies) and/or inflammation. The examples provided below show a complete inhibition of such adenosine receptor associated symptoms in a rabbit model for human bronchoconstriction allergy(ies) and inflammation as well as the elimination of the ability of the adenosine receptor agonist par excellence, adenosine, to cause bronchoconstriction in hyper-responsive monkeys, which are animal models for human hyper-responsiveness to adenosine receptor agonists. The pharmaceutical composition and formulations of the invention, therefore, are suitable for preventing and alleviating the symptoms associated with stimulation of adenosine receptors, such as the adenosine $A_1$ receptors. The compositions and formulations of this invention, thus, are also suitable for prevent the untoward side effects of adenosine-mediated hyperresponsive in certain individuals, which are generally seen in disease affecting respiratory activity. Examples of disease and conditions, which may be treated preventatively, prophylactically and therapeutically with the compositions and formulations of this invention, are pulmonary vasoconstriction, inflammation, allergies, asthma, impeded respiration, Acute Respiratory Distress Syndrome (ARDS), renal damage and failure associated with ischemia as well as the administration of certain drugs, side effects associated with adenosine administration e.g. in SupraVentricular Tachycardia (SVT) and in adenosine stress tests, infantile Respiratory Distress Syndrome (infantile RDS), pain, cystic fibrosis, pulmonary hypertension, pulmonary vasoconstriction, emphysema, chronic obstructive pulmonary disease (COPD), and cancers such as leukemias, lymphomas, carcinomas, and the like, e.g. colon cancer, breast cancer, lung cancer, pancreatic cancer, hepatocellular, kidney cancer, melanoma, heparic metastases, etc., as well as all other metastic cancers, e.g. cancers with metastasized to the lung(s), breast and prostate. The present compositions and formulations are suitable for administration before, during and after other treatments, including radiation, chemotherapy, antibody therapy, phototherapy an cancer, and other types of surgery. The present compositions and formulations may also be administered effectively as a substitute for therapies that have significant negative side effects.

All nucleotide sequences are represented in this patent by a single strand only, and in the 5' to 3' direction, from left to right. All nucleotide and amino acids are represented in the manner recommended by the IUPAC-IUB Biochemical Nomenclature Commission, or (for amino acids) by three letter code, in accordance with 37 CFR 1.822 and established usage. See, e.g., PatentIn User Manual, 99–102 (Nov. 1990) (U.S. Patent and Trademark Office, Office of the Assistant Commissioner for Patents, Washington, D.C. 20231); U.S. Pat. No. 4,871,670 to Hudson et al., at col. 3, lines 20–43. The relevant sections of the disclosures of the above cited, and of all other patents and references cited in this patent are incorporated herein by reference.

The method of the present invention may be used to reduce adenosine receptor associated bronchoconstriction in the lungs of a subject for any reason, including, but not limited to, bronchoconstriction allergy(ies) and/or inflammation. The compositions and formulations of the invention comprise a surfactant and an oligonucleotide which is anti-sense to the adenosine $A_1$, $A_{2b}$ and $A_3$ receptors have shown to be effective in the down-regulation of the adenosine $A_1$, $A_{2b}$ or $A_3$ receptors, respectively, in the cell. Others which are anti-sense to the adenosine $A_2$, receptors are also effective as long as they have some adenosine $A_1$ inhibitory activity. One novel feature of this treatment, as compared to traditional treatments for adenosine-mediated bronchoconstriction and other symptoms, is that the compositions and formulations of this invention may be administered directly into the respiratory system of an individual, and even to his/her lungs. In addition, the present treatment may reduce the amount or level of a receptor proteins itself rather than merely acting at the receptor as is the case with treatments and/or where the agent is merely an antagonist acting at the receptor site. The selective characteristic of the present compositions and formulations along with their administration by a selected route results in reduced toxicity.

As used herein, the terms "prevent", "preventing","treat" or "treating" refer to a preventive or therapeutic treatment which decreases the likelihood that the subject administered such treatment will manifest symptoms associated with adenosine receptor stimulation. The term "down-regulate" refers to inducing a decrease in production, secretion or availability and, thus, a decrease in concentration of intracellular adenosine $A_1$, $A_{2b}$ or $A_3$ receptor or an increase in concentration of the adenosine. $A_2$, receptor. Although the present invention is primarily concerned with the treatment of human subjects, it is also applicable to the treatment of animals, such as other vertebrates, including mammals, large and small, wild and domesticated, including pets, e.g. dogs and cats, for veterinary purposes. In general, "anti-sense" refers to small, many times synthetic, oligonucleotides, resembling single-stranded DNA, targeted to a specific gene, its flanking regions, mRNA or protein encoded by the gene and mRNA, which may be utilized for inhibiting gene expression by inhibiting the function of the target messenger RNA (mRNA). Milligan, J. F. et al., J. Med. Chem. 36(14), 1923–1937 (1993). The present invention, thus, is intended for inhibiting gene expression of the adenosine. $A_1$, $A_{2b}$ and $A_3$ receptor as well as for promoting the gene expression of the adenosine $A_2$, receptor. As is generally known in the art, the inhibition of gene expression may be I brought about through anti-sense oligonucleotide hybridization to the coding (sense) sequences in a specific messenger RNA (mRNA) target, e.g. by hydrogen bonding according to Watson-Crick base pairing rules. In general, the exogenously administered anti-sense oligos decrease the mRNA and protein levels of the target gene or cause changes in the growth characteristics or shapes of the cells. Ibid. See, also Helene, C. and Toulme, J., Biochim. Biophys. Acta 1049: 99–125 (1990); Cohen, J. S., Ed., Oligodeoxynucleotides as Antisense Inhibitors of Gene Expression; CRC Press: Boca Raton, Fla. (1987). As used herein, "adenosine receptor anti-sense oligonucleotide" is a short sequence of synthetic nucleotide that (1) hybridizes to any coding sequence in an mRNA which codes for an adenosine receptor, e.g., the adenosine $A_1$, $A_{2b}$ or $A_3$ receptor, under in vivo hybridization conditions described below, and that (2) upon hybridization causes a decrease in gene expression of the adenosine $A_1$, $A_{2b}$ or $A_3$ receptor.

The mRNA sequence of the adenosine $A_1$, $A_{2b}$ and $A_3$ receptors may be derived from the DNA base sequences of the genes expressing either the adenosine $A_1$, $A_{2b}$ and $A_3$ receptors. The sequence of the genomic human adenosine $A_1$ receptor is known and is disclosed in U.S. Pat. No. 5,320, 962 to G. Stiles et al. The adenosine $A_{2b}$ receptor is also known. See, GenBank, Accession No. X68486; GenBank Accession No. X68487. The adenosine $A_3$ receptor has been cloned, sequenced and expressed in rat and humans. See, F. Zhou et al., Proc. Nat'l Acad. Sci. (USA) 89:7432 (1992); M. A. Jacobson et al., U.K. Patent Application No. 9304582.1 (1993). The antisense oligonucleotide that downregulate the production of the adenosine $A_1$, $A_{2b}$ and $A_3$ receptor may be produced in accordance with standard techniques.

The anti-sense agent of this invention binds specifically with any sequence of a mRNA molecule which encodes an adenosine $A_1$, $A_{2a}$, $A_{2b}$ or $A_3$ receptor, and prevents translation of the mRNA molecule. In one embodiment of the present invention, the anti-sense oligonucleotide has one of the following sequences. In another preferred embodiment, the agent of the invention comprises fragments of these sequences or their combinations as well as sequences with decreased adenosine contents when compared with the natural sequences, where one or more adenosines are replaced by a universal base or adenosine analogue which does not activate adenosine receptors, particularly adenosine $A_1$ receptors.

5'-GAT GGA GGG CGG CAT GGC GGG-3' (SEQ. ID NO:1)
5'-GTT GTT GGG CAT CTT GCC-3' (SEQ. ID NO:3)
5'-GTG GGC CTA GCT CTC GCC-3' (SEQ. ID NO:5)

In another embodiment of the invention, the sequence of the anti-sense oligonucleotide brackets the initiation condon of the adenosine $A_1$ receptor, for example that of the human receptor mRNA. Preferred human adenosine $A_1$ receptor anti-sense oligonucleotide may have the SEQ. ID NO:7 or any one of its fragments, including one of the following sequences. In another preferred embodiment, fragments of these sequences and/or their combinations are also within the confines of the invention.

5'-GGC GGC CTG GAA AGC TGA GAT GGA GGG CGG CAT GGC GGG CAC AGG CTG GGC-3' (SEQ. ID NO:7)

5'-GGC GGC CTG GAA AGC TGA GAT GGA GGG CGG CAT GGC GGG CAC AGG CTG GG-3' (Fragment 1) (SEQ. ID NO:8)

5'-GGC GGC CTG GAA AGC TGA GAT GGA GGG CGG CAT GGC GGG CAC AGG CTG G-3' (Fragment 2) (SEQ. ID NO:9)

5'-GGC GGC CTG GAA AGC TGA GAT GGA GGG CGG CAT GGC GGG CAC AGG CTG-3' (Fragment 3) (SEQ. ID NO:10)

5'-GGC GGC CTG GAA AGC TGA GAT GGA GGG CGG CAT GGC GGG CAC AGG CT-3' (Fragment 4) (SEQ. ID NO:11)

5'-GGC GGC CTG GAA AGC TGA GAT GGA GGG CGG CAT GGC GGG CAC AGG C-3' (Fragment 5) (SEQ. ID NO:12)

5'-GGC GGC CTG GAA AGC TGA GAT GGA GGG CGG CAT GGC GGG CAC AGG-3' (Fragment 6) (SEQ. ID NO:13)

5'-GGC GGC CTG GAA AGC TGA GAT GGA GGG CGG CAT GGC GGG CAC AG-3' (Fragment 7) (SEQ. ID NO:14)

5'-GGC GGC CTG GAA AGC TGA GAT GGA GGG CGG CAT GGC CGG CAC A-3' (Fragment 8) (SEQ. ID NO:15)

5'-GGC GGC CTG GAA AGC TGA GAT GGA GGG CGG CAT GGC GGG CAC-3' (Fragment 9) (SEQ. ID NO:16)

5'-GGC GGC CTG GAA AGC TGA GAT GGA GGG CGG CAT GGC GGG CA-3' (Fragment 10) (SEQ. ID NO:17)

5'-GGC GGC CTG GAA AGC TGA GAT GGA GGG CGG CAT GGC GGG C-3' (Fragment 11) (SEQ. ID NO:18)

5'-GGC GGC CTG GAA AGC TGA GAT GGA GGG CGG CAT GGC GGG-3' (Fragment 12) (SEQ. ID NO:19)

5'-GGC GGC CTG GAA AGC TGA GAT GGA GGG CGG CAT GGC GG-3' (Fragment 13) (SEQ. ID NO:20)

5'-GGC GGC CTG GAA AGC TGA GAT GGA GGG CGG CAT GGC G-3' (Fragment 14) (SEQ. ID NO:21)

5'-GGC GGC CTG GAA AGC TGA GAT GGA GGG CGG CAT GGC-3' (Fragment 15) (SEQ. ID NO:22)

5'-GGC GGC CTG GAA AGC TGA GAT GGA GGG CGG CAT GG-3'(Fragment 16) (SEQ. ID NO:23)

5'-GGC GGC CTG GAA AGC TGA GAT GGA GGG CGG CAT G-3' (Fragment 17) (SEQ. ID NO:24)

5'-GGC GGC CTG GAA AGC TGA GAT GGA GGG CGG CAT-3' (Fragment 18) (SEQ. ID NO:25)

5'-GGC GGC CTG GAA AGC TGA GAT GGA GGG CGG CA-3' (Fragment 19) (SEQ. ID NO:26)

5'-GGC GGC CTG GAA AGC TGA GAT GGA GGG CGG C-3' (Fragment 20) (SEQ. ID NO:27)

5'-GGC GGC CTG GAA AGC TGA GAT GGA GGG CGG-3' (Fragment 21) (SEQ. ID NO:28)

5'-GGC GGC CTG GAA AGC TGA GAT GGA GGG CG-3' (Fragment 22) (SEQ. ID NO:29)

5'-GGC GGC CTG GAA AGC TGA GAT GGA GGG C-3' (Fragment 23) (SEQ. ID NO:30)

5'-GGC GGC CTG GAA AGC TGA GAT GGA GGG-3' (Fragment 24) (SEQ. ID NO:31)

5'-GGC GGC CTG GAA AGC TGA GAT GGA GG-3' (Fragment 25) (SEQ. ID NO:32)

5'-GGC GGC CTG GAA AGC TGA GAT GGA G-3' (Fragment 26) (SEQ. ID NO:33)

5'-GGC GGC CTG GAA AGC TGA GAT GGA-3' (Fragment 27) (SEQ. ID NO:34)

5'-GGC GGC CTG GAA AGC TGA GAT GG-3' (Fragment 28) (SEQ. ID NO:35)

5'-GGC GGC CTG GAA AGC TGA GAT G-3"(Fragment 29) (SEQ. ID NO:36)

5'-GGC GGC CTG GAA AGC TGA GAT-3' (Fragment 30) (SEQ. ID NO:37)

5'-GGC GGC CTG GAA AGC TGA GA-3' (Fragment 31) (SEQ. ID NO:38)

5'-GGC GGC CTG GAA AGC TGA G-3' (Fragment 32) (SEQ. ID NO:39)

5'-GGC GGC CTG GAA AGC TGA-3' (Fragment 33) (SEQ. ID NO:40)

5'-GGC GGC CTG GAA AGC TG-3' (Fragment 34) (SEQ. ID NO:41)

5'-GGC GGC CTG GAA AGC T-3' (Fragment 35) (SEQ. ID NO:42)

5'-GGC GGC CTG GAA AGC-3' (Fragment 36) (SEQ. ID NO:43)

5'-GGC GGC CTG GAA AG-3' (Fragment 37) (SEQ. ID NO:44)

5'-GGC GGC CTG GAA A-3' (Fragment 38) (SEQ. ID NO:45)

5'-GGC GGC CTG GAA-3' (Fragment 39) (SEQ. ID NO:46)

5'-GGC GGC CTG GA-3' (Fragment 40) (SEQ. ID NO:47)

5'-GGC GGC CTG G-3' (Fragment 41 (SEQ. ID NO:48)

5'-GC GGC CTG GAA AGC TGA GAT GGA GGG CGG CAT GGC GGG CAC AGG CTG GGC-3' (Fragment 42 (SEQ. ID NO:49)

5'-GC GGC CTG GAA AGC TGA GAT GGA GGG CGG CAT GGC GGG CAC AGG CTG GG-3' (Fragment 43 (SEQ. ID NO:50)

5'-GC GGC CTG GAA AGC TGA GAT GGA GGG CGG CAT GGC GGG CAC AGG CTG G-3' (Fragment 44 (SEQ. ID NO:51)

5'-GC GGC CTG GAA AGC TGA GAT GGA GGG CGG CAT GGC GGG CAC AGG CTG-3' (Fragment 45) (SEQ. ID NO:52)

5'-GC GGC CTG GAA AGC TGA GAT GGA GGG CGG CAT GGC GGG CAC AGG CT-3' (Fragment 46) (SEQ. ID NO:53)

5'-GC GGC CTG GAA AGC TGA GAT GGA GGG CGG CAT GGC GGG CAC AGG C-3' (Fragment 47) (SEQ. ID NO:54)

5'-GC GGC CTG GAA AGC TGA GAT GGA GGG CGG CAT GGC GGG CAC AGG-3' (Fragment 48) (SEQ. ID NO:55)

5'-GC GGC CTG GAA AGC TGA GAT GGA GGG CGG CAT GGC GGG CAC AG-3' (Fragment 49) (SEQ. ID NO:56)

5'-GC GGC CTG GAA AGC TGA GAT GGA GGC CGG CAT GGC GGG CAC A-3' (Fragment 50) (SEQ. ID NO:57)

5'-GC GGC CTG GAA AGC TGA GAT GGA GGG CGG CAT GGC GGG CAC-3' (Fragment 51) (SEQ. ID NO:58)

5'-GC GGC CTG GAA AGC TGA CAT GGA GGG CGG CAT GGC GGG CA-3' (Fragment 52) (SEQ. ID NO:59)

5'-GC GGC CTG GAA AGC TGA GAT GGA GGG CGG CAT GGC GGG C-3' (Fragment 53) (SEQ. ID NO:60)

5'-GC GGC CTG GAA AGC TGA GAT GGA GGG CGG CAT GGC GGG-3' (Fragment 54) (SEQ. ID NO:61)

5'-GC GGC CTG GAA AGC TGA GAT GGA GGG CGG CAT GGC GG-3' (Fragment 55) (SEQ. ID NO:62)

5'-GC GGC CTG GAA AGC TGA GAT GGA GGG CGG CAT GGC G-3' (Fragment 56) (SEQ. ID NO:63)

5'-GC GGC CTG GAA AGC TGA GAT GGA GGG CGG CAT GGC-3' (Fragment 57) (SEQ. ID NO:64)

5'-GC GGC CTG GAA AGC TGA GAT GGA GGG CGG CAT GG-3' (Fragment 58) (SEQ. ID NO:65)

5'-GC GGC CTG GAA AGC TGA GAT GGA GGG CGG CAT G-3' (Fragment 59) (SEQ. ID NO:66)

5'-GC GGC CTG GAA AGC TGA GAT GGA GGG CGG CAT-3' (Fragment 60) (SEQ. ID NO:67)

5'-GC GGC CTG GAA AGC TGA GAT GGA GGG CGG CA-3' (Fragment 61) (SEQ. ID NO:68)

5'-GC GGC CTG GAA AGC TGA GAT GGA GGG CGG C-3' (Fragment 62) (SEQ. ID NO:69)

5'-GC GGC CTG GAA AGC TGA GAT GGA GGG CGG-3' (Fragment 63) (SEQ. ID NO:70)

5'-GC GGC CTG GAA AGC TGA GAT GGA GGG CG-3' (Fragment 64) (SEQ. ID NO:71)

5'-GC GGC CTG GAA AGC TGA GAT GGA GGG C-3' (Fragment 65) (SEQ. ID NO:72)

5'-GC GGC CTG GAA AGC TGA GAT GGA GGG-3' (Fragment 66) (SEQ. ID NO:73)

5'-GC GGC CTG GAA AGC TGA GAT GGA GG-3' (Fragment 67) (SEQ. ID NO:74)

5'-GC GGC CTG GAA AGC TGA GAT GGA G-3' (Fragment 68) (SEQ. ID NO:75)

5'-GC GGC CTG GAA AGC TGA GAT GGA-3' (Fragment 69) (SEQ. ID NO:76)

5'-GC GGC CTG GAA AGC TGA GAT GG-3' (Fragment 70) (SEQ. ID NO:77)

5'-GC GGC CTG GAA AGC TGA GAT G-3' (Fragment 71) (SEQ. ID NO:78)

5'-GC GGC CTG GAA AGC TGA GAT -3' (Fragment 72) (SEQ. ID NO:79)

5'-GC GGC CTG GAA AGC TGA GA-3' (Fragment 73) (SEQ. ID NO:80)

5'-GC GGC CTG GAA AGC TGA G-3' (Fragment 74) (SEQ. ID NO:81)

5'-GC GGC CTG GAA AGC TGA-3' (Fragment 75) (SEQ. ID NO:82)

5'-GC GGC CTG GAA AGC TG-3' (Fragment 76) (SEQ. ID NO:83)

5'-GC GGC CTG GAA AGC T-3' (Fragment 77) (SEQ. ID NO:84)

5'-GC GGC CTG GAA AGC-3' (Fragment 78) (SEQ. ID NO:85)

5'-GC GGC CTG GAA AG-3' (Fragment 79) (SEQ. ID NO:86)

5'-GC GGC CTG GAA A-3' (Fragment 80) (SEQ. ID NO:87)

5'-GC GGC CTG GAA-3' (Fragment 81) (SEQ. ID NO:88)

5'-GC GGC CTG GA-3'(Fragment 82) (SEQ. ID NO:89)

5'-C GGC CTG GAA AGC TGA GAT GGA GGG CGG CAT GGC GGG CAC AGG CTG GGC-3' (Fragment 83) (SEQ. ID NO:90)

5'-C GGC CTG GAA AGC TGA GAT GGA GGG CGG CAT GGC GGG CAC AGG CTG GG-3' (Fragment 84) (SEQ. ID NO:91)

5'-C GGC CTG GAA AGC TGA GAT GGA GGG CGG CAT GGC GGG CAC AGG CTG G-3' (Fragment 85) (SEQ. ID NO:92)

5'-C GGC CTG GAA AGC TGA GAT GGA GGG CGG CAT GGC GGG CAC AGG CTG-3' (Fragment 86) (SEQ. ID NO:93)

5'-C GGC CTG GAA AGC TGA GAT GGA GGG CGG CAT GGC GGG CAC AGG CT-3' (Fragment 87) (SEQ. ID NO:94)

5'-C GGC CTG GAA AGC TGA GAT GGA GGG CGG CAT GGC GGG CAC AGG C-3' (Fragment 88) (SEQ. ID NO:95)

5'-C GGC CTG GAA AGC TGA GAT GGA GGG CGG CAT GGC GGG CAC AGG-3' (Fragment 89) (SEQ. ID NO:96)

5'-C GGC CTG GAA AGC TGA GAT GGA GGG CGG CAT GGC GGG CAC AG-3' (Fragment 90) (SEQ. ID NO:97)

5'-C GGC CTG GAA AGC TGA GAT GGA GGG CGG CAT GGC GGG CAC A-3' (Fragment 91) (SEQ. ID NO:98)

5'-C GGC CTG GAA AGC TGA GAT GGA GGG CGG CAT GGC GGG CAC-3' (Fragment 92) (SEQ. ID NO:99)

5'-C GGC CTG GAA AGC TGA GAT GGA GGG CGG CAT GGC GGG CA-3' (Fragment 93) (SEQ. ID NO:100)

5'-C GGC CTG GAA AGC TGA GAT GGA GGG CGG CAT GGC GGG C-3' (Fragment 94) (SEQ. ID NO:101)

5'-C GGC CTG GAA AGC TGA GAT GGA GGG CGG CAT GGC GGG-3' (Fragment 95) (SEQ. ID NO:102)

5'-C GGC CTG GAA AGC TGA GAT GGA GGG CGG CAT GGC GG-3' (Fragment 96) (SEQ. ID NO:103)

5'-C GGC CTG GAA AGC TGA GAT GGA GGG CGG CAT GGC G-3' (Fragment 97) (SEQ. ID NO:104)

5'-C GGC CTG GAA AGC TGA GAT GGA GGG CGG CAT GGC-3' (Fragment 98) (SEQ. ID NO:105)

5'-C GGC CTG GAA AGC TGA GAT GGA GGG CGG CAT GG-3' (Fragment 99) (SEQ. ID NO:106)

5'-C GGC CTG GAA AGC TGA GAT GGA GGG CGG CAT G-3' (Fragment 100) (SEQ. ID NO:107)

5'-C GGC CTG GAA AGC TGA GAT GGA GGG CGG CAT-3' (Fragment 101) (SEQ. ID NO:108)

5'-C GGC CTG GAA AGC TGA GAT GGA GGG CGG CA-3' (Fragment 102) (SEQ. ID NO:109)

5'-C GGC CTG GAA AGC TGA GAT GGA GGG CGG C-3' (Fragment 103) (SEQ. ID NO:110)

5'-C GGC CTG GAA AGC TGA GAT GGA GGG CGG-3' (Fragment 104) (SEQ. ID NO:111)

5'-C GGC CTG GAA AGC TGA GAT GGA GGG CG-3' (Fragment 105) (SEQ. ID NO:112)

5'-C GGC CTG GAA AGC TGA GAT GGA GGG C-3' (Fragment 106) (SEQ. ID NO:113)

5'-C GGC CTG GAA AGC TGA GAT GGA GGG-3' (Fragment 107) (SEQ. ID NO:114)

5'-C GGC CTG GAA AGC TGA GAT GGA GG-3' (Fragment 108) (SEQ. ID NO:115)

5'-C GGC CTG GAA AGC TGA GAT GGA G-3' (Fragment 109) (SEQ. ID NO:116)

5'-C GGC CTG GAA AGC TGA GAT GGA-3' (Fragment 110) (SEQ. ID NO:117)

5'-C GGC CTG GAA AGC TGA GAT GG-3' (Fragment 111) (SEQ. ID NO:118)

5'-C GGC CTG GAA AGC TGA GAT G-3' (Fragment 112) (SEQ. ID NO:119)

5'-C GGC CTG GAA AGC TGA GAT-3' (Fragment 113) (SEQ. ID NO:120)

5'-C GGC CTG GAA AGC TGA GA-3' (Fragment 114) (SEQ. ID NO:121)

5'-C GGC CTG GAA AGC TGA G-3' (Fragment 115) (SEQ. ID NO:122)
5'-C GGC CTG GAA AGC TGA-3' (Fragment 116) (SEQ. ID NO:123)
5'-C GGC CTG GAA AGC TG-3' (Fragment 117) (SEQ. ID NO:124)
5'-C GGC CTG GAA AGC T-3' (Fragment 118) (SEQ. ID NO:125)
5'-C GGC CTG GAA AGC-3' (Fragment 119) (SEQ. ID NO:126)
5'-C GGC CTG GAA AG-3' (Fragment 120) (SEQ. ID NO:127)
5'-C GGC CTG GAA A-3' (Fragment 121) (SEQ. ID NO:128)
5'-C GGC CTG GAA-3' (Fragment 122) (SEQ. ID NO:129)
5'-GGC CTG GAA AGC TGA GAT GGA GGG CGG CAT GGC GGG CAC AGG CTG GGC-3' (Fragment 123) (SEQ. ID NO:130)
5'-GGC CTG GAA AGC TGA GAT GGA GGG CGG CAT GGC GGG CAC AGG CTG GG-3' (Fragment 124) (SEQ. ID NO:131)
5'-GGC CTG GAA AGC TGA GAT GGA GGG CGG CAT GGC GGG CAC AGG CTG G-3' (Fragment 125) (SEQ. ID NO:132)
5'-GGC CTG GAA AGC TGA GAT GGA GGG CGG CAT GGC GGG CAC AGG CTG-3' (Fragment 126) (SEQ. ID NO:133)
5'-GGC CTG GAA AGC TGA GAT GGA GGG CGG CAT GGC GGG CAC AGG CT-3' (Fragment 127) (SEQ. ID NO:134)
5'-GGC CTG GAA AGC TGA GAT GGA GGG CGG CAT GGC GGG CAC AGG C-3' (Fragment 128) (SEQ. ID NO:135)
5'-GGC CTG GAA AGC TGA GAT GGA GGG CGG CAT GGC GGG CAC AGG-3' (Fragment 129) (SEQ. ID NO:136)
5'-GGC CTG GAA AGC TGA GAT GGA GGG CGG CAT GGC GGG CAC AG-3' (Fragment 130) (SEQ. ID NO:137)
5'-GGC CTG GAA AGC TGA GAT GGA GGG CGG CAT GGC GGG CAC A-3' (Fragment 131) (SEQ. ID NO:138)
5'-GGC CTG GAA AGC TGA GAT GGA GGG CGG CAT GGC GGG CAC-3' (Fragment 132) (SEQ. ID NO:139)
5'-GGC CTG GAA AGC TGA GAT GGA GGG CGG CAT GGC GGG CA-3' (Fragment 133) (SEQ. ID NO:140)
5'-GGC CTG GAA AGC TGA GAT GGA GGG CGG CAT GGC GGG C-3' (Fragment 134) (SEQ. ID NO:141)
5'-GGC CTG GAA AGC TGA GAT GGA GGG CGG CAT GGC GGG-3' (Fragment 135) (SEQ. ID NO:142)
5'-GGC CTG GAA AGC TGA GAT GGA GGG CGG CAT GGC GG-3' (Fragment 136) (SEQ. ID NO:143)
5'-GGC CTG GAA AGC TGA GAT GGA GGG CGG CAT GGC G-3' (Fragment 137) (SEQ. ID NO:144)
5'-GGC CTG GAA AGC TGA GAT GGA GGG CGG CAT GGC-3' (Fragment 138) (SEQ. ID NO:145)
5'-GGC CTG GAA AGC TGA GAT GGA GGG CGG CAT GG-3' (Fragment 139) (SEQ. ID NO:146)
5'-GGC CTG GAA AGC TGA GAT GGA GGG CGG CAT G-3' (Fragment 140) (SEQ. ID NO:147)
5'-GGC CTG GAA AGC TGA GAT GGA GGG CGG CAT-3' (Fragment 141) (SEQ. ID NO:148)
5'-GGC CTG GAA AGC TGA GAT GGA GGG CGG CA-3' (Fragment 142) (SEQ. ID NO:149)
5'-GGC CTG GAA AGC TGA GAT GGA GGG CGG C-3' (Fragment 143) (SEQ. ID NO:150)
5'-GGC CTG GAA AGC TGA GAT GGA GGG CGG-3' (Fragment 144) (SEQ. ID NO:151)
5'-GGC CTG GAA AGC TGA GAT GGA GGG CG-3' (Fragment 145) (SEQ. ID NO:152)
5'-GGC CTG GAA AGC TGA GAT GGA GGG C-3' (Fragment 146) (SEQ. ID NO:153)
5'-GGC CTG GAA AGC TGA GAT GGA GGG-3' (Fragment 147) (SEQ. ID NO:154)
5'-GGC CTG GAA AGC TGA GAT GGA GG-3' (Fragment 148) (SEQ. ID NO:155) (Fragment 88) (SEQ. ID NO:95)
5'-C GGC CTG GAA AGC TGA GAT GGA GGG CGG CAT GGC GGG CAC AGG-3' (Fragment 89) (SEQ. ID NO:96)
5'-C GGC CTG GAA AGC TGA GAT GGA GGG CGG CAT GGC GGG CAC AG-3' (Fragment 90) (SEQ. ID NO:97)
5'-C GGC CTG GAA AGC TGA GAT GGA GGG CGG CAT GGC GGG CAC A-3' (Fragment 91) (SEQ. ID NO:98)
5'-C GGC CTG GAA AGC TGA GAT GGA GGG CGG CAT GGC GGG CAC-3' (Fragment 92) (SEQ. ID NO:99)
5'-C GGC CTG GAA AGC TGA GAT GGA GGG CGG CAT GGC GGG CA-3' (Fragment 93) (SEQ. ID NO:100)
5'-C GGC CTG GAA AGC TGA GAT GGA GGG CGG CAT GGC GGG C-3' (Fragment 94) (SEQ. ID NO:101)
5'-C GGC CTG GAA AGC TGA GAT GGA GGG CGG CAT GGC GGG-3' (Fragment 95) (SEQ. ID NO:102)
5'-C GGC CTG GAA AGC TGA GAT GGA GGG CGG CAT GGC GG-3' (Fragment 96) (SEQ. ID NO:103)
5'-C GGC CTG GAA AGC TGA GAT GGA GGG CGG CAT GGC G-3' (Fragment 97) (SEQ. ID NO:104)
5'-C GGC CTG GAA AGC TGA GAT GGA GGG CGG CAT GGC-3' (Fragment 98) (SEQ. ID NO:105)
5'-C GGC CTG GAA AGC TGA GAT GGA GGG CGG CAT GG-3' (Fragment 99) (SEQ. ID NO:106)
5'-C GGC CTG GAA AGC TGA GAT GGA GGG CGG CAT G-3' (Fragment 100) (SEQ. ID NO:107)
5'-C GGC CTG GAA AGC TGA GAT GGA GGG CGG CAT-3' (Fragment 101) (SEQ. ID NO:108)
5'-C GGC CTG GAA AGC TGA GAT GGA GGG CGG CA-3' (Fragment 102) (SEQ. ID NO:109)
5'-C GGC CTG GAA AGC TGA GAT GGA GGG CGG C-3' (Fragment 103) (SEQ. ID NO:110)
5'-C GGC CTG GAA AGC TGA GAT GGA GGG CGG-3' (Fragment 104) (SEQ. ID NO:111)
5'-C GGC CTG GAA AGC TGA GAT GGA GGG CG-3' (Fragment 105) (SEQ. ID NO:112)
5'-C GGC CTG GAA AGC TGA GAT GGA GGG C-3' (Fragment 106) (SEQ. ID NO:113)
5'-C GGC CTG GAA AGC TGA GAT GGA GGG-3' (Fragment 107) (SEQ. ID NO:114)
5'-C GGC CTG GAA AGC TGA GAT GGA GG-3' (Fragment 108) (SEQ. ID NO:115)
5'-C GGC CTG GAA AGC TGA GAT GGA G-3' (Fragment 109) (SEQ. ID NO:116)
5'-C GGC CTG GAA AGC TGA GAT GGA-3' (Fragment 110) (SEQ. ID NO:117)
5'-C GGC CTG GAA AGC TGA GAT GG-3' (Fragment 111) (SEQ. ID NO:118)
5'-C GGC CTG GAA AGC TGA GAT G-3' (Fragment 112) (SEQ. ID NO:119)
5'-C GGC CTG GAA AGC TGA GAT-3' (Fragment 113) (SEQ. ID NO:120)
5'-C GGC CTG GAA AGC TGA GA-3' (Fragment 114) (SEQ. ID NO:121)
5'-C GGC CTG GAA AGC TGA G-3' (Fragment 115) (SEQ. ID NO:122)
5'-C GGC CTG GAA AGC TGA-3' (Fragment 116) (SEQ. ID NO:123)

5'-C GGC CTG GAA AGC TG-3' (Fragment 117) (SEQ. ID NO:124)
5'-C GGC CTG GAA AGC T-3' (Fragment 118) (SEQ. ID NO:125)
5'-C GGC CTG GAA AGC-3' (Fragment 119) (SEQ. ID NO:126)
5'-C GGC CTG GAA AG-3' (Fragment 120) (SEQ. ID NO:127)
5'-C GGC CTG GAA A-3' (Fragment 121) (SEQ. ID NO:128)
5'-C GGC CTG GAA-3' (Fragment 122) (SEQ. ID NO:129)
5'-GGC CTG GAA AGC TGA GAT GGA GGG CGG CAT GGC GGG CAC AGG CTG GGC-3' (Fragment 123) (SEQ. ID NO:130)
5'-GGC CTG GAA AGC TGA GAT GGA GGG CGG CAT GGC GGG CAC AGG CTG GG-3'
5'-GC CTG GAA AGC TGA GAT GGA GGG C-3' (Fragment 185) (SEQ. ID NO:192)
5'-GC CTG GAA AGC TGA GAT GGA GGG-3' (Fragment 186) (SEQ. ID NO:193)
5'-GC CTG GAA AGC TGA GAT GGA GG-3' (Fragment 187) (SEQ. ID NO:194)
5'-GC CTG GAA AGC TGA GAT GGA G-3' (Fragment 188) (SEQ. ID NO:195)
5'-GC CTG GAA AGC TGA GAT GGA-3' (Fragment 189) (SEQ. ID NO:196)
5'-GC CTG GAA AGC TGA GAT GG-3' (Fragment 190) (SEQ. ID NO:197)
5'-GC CTG GAA AGC TGA GAT G-3' (Fragment 191) (SEQ. ID NO:198)
5'-GC CTG GAA AGC TGA GAT-3' (Fragment 192) (SEQ. ID NO:199)
5'-GC CTG GAA AGC TGA GA-3' (Fragment 193) (SEQ. ID NO:200)
5'-GC CTG GAA AGC TGA G-3' (Fragment 194) (SEQ. ID NO:201)
5'-GC CTG GAA AGC TGA-3' (Fragment 195) (SEQ. ID NO:202)
5'-GC CTG GAA AGC TG-3' (Fragment 196) (SEQ. ID NO:203)
5'-GC CTG GAA AGC T-3' (Fragment 197) (SEQ. ID NO:204)
5'-GC CTG GAA AGC-3' (Fragment 198) (SEQ. ID NO:205)
5'-GC CTG GAA AG-3' (Fragment 199) (SEQ. ID NO:206)
5'-C CTG GAA AGC TGA GAT GGA GGG CGG CAT GGC GGG CAC AGG CTG GGC-3' (Fragment 200) (SEQ. ID NO:207)
5'-C CTG GAA AGC TGA GAT GGA GGG CGG CAT GGC GGG CAC AGG CTG GG-3' (Fragment 201) (SEQ. ID NO:208)
5'-C CTG GAA AGC TGA GAT GGA GGG CGG CAT GGC GGG CAC AGG CTG G-3' (Fragment 202) (SEQ. ID NO:209)
5'-C CTG GAA AGC TGA GAT GGA GGG CGG CAT GGC GGG CAC AGG CTG-3' (Fragment 203) (SEQ. ID NO:210)
5'-C CTG GAA AGC TGA GAT GGA GGG CGG CAT GGC GGG CAC AGG CT-3' (Fragment 204) (SEQ. ID NO:211)
5'-C CTG GAA AGC TGA GAT GGA GGG CGG CAT GGC GGG CAC AGG C-3' (Fragment 205) (SEQ. ID NO:212)
5'-C CTG GAA AGC TGA GAT GGA GGG CGG CAT GGC GGG CAC AGG-3' (Fragment 206) (SEQ. ID NO:213)
5'-C CTG GAA AGC TGA GAT GGA GGG CGG CAT GGC GGG CAC AG-3' (Fragment 207) (SEQ. ID NO:214)
5'-C CTG GAA AGC TGA GAT GGA GGG CGG CAT GGC GGG CAC A-3' (Fragment 208) (SEQ. ID NO:215)
5'-C CTG GAA AGC TGA GAT GGA GGG CGG CAT GGC GGG CAC-3' (Fragment 209) (SEQ. ID NO:216)
5'-C CTG GAA AGC TGA GAT GGA GGG CGG CAT GGC GGG CA-3' (Fragment 210) (SEQ. ID NO:217)
5'-C CTG GAA AGC TGA GAT GGA GGG CGG CAT GGC GGG C-3' (Fragment 211) (SEQ. ID NO:218)
5'-C CTG GAA AGC TGA GAT GGA GGG CGG CAT GGC GGG-3' (Fragment 212) (SEQ. ID NO:219)
5'-C CTG GAA AGC TGA GAT GGA GGG CGG CAT GGC GG-3' (Fragment 213) (SEQ. ID NO:220)
5'-C CTG GAA AGC TGA GAT GGA GGG CGG CAT GGC G-3' (Fragment 214) (SEQ. ID NO:221)
5'-C CTG GAA AGC TGA GAT GGA GGG CGG CAT GGC-3' (Fragment 215) (SEQ. ID NO:222)
5'-C CTG GAA AGC TGA GAT GGA GGG CGG CAT GG-3' (Fragment 216) (SEQ. ID NO:223)
5'-C CTG GAA AGC TGA GAT GGA GGG CGG CAT G-3' (Fragment 217) (SEQ. ID NO:224)
5'-C CTG GAA AGC TGA GAT GGA GGG CGG CAT-3' (Fragment 218) (SEQ. ID NO:225)
5'-C CTG GAA AGC TGA GAT GGA GGG CGG CA-3' (Fragment 219) (SEQ. ID NO:226)
5'-C CTG GAA AGC TGA GAT GGA GGG CGG C-3' (Fragment 220) (SEQ. ID NO:227)
5'-C CTG GAA AGC TGA GAT GGA GGG CGG-3' (Fragment 221) (SEQ. ID NO:228)
5'-C CTG GAA AGC TGA GAT GGA GGG CG-3' (Fragment 222) (SEQ. ID NO:229)
5'-C CTG GAA AGC TGA GAT GGA GGG C-3' (Fragment 223) (SEQ. ID NO:230)
5'-C CTG GAA AGC TGA GAT GGA GGG-3' (Fragment 224) (SEQ. ID NO:231)
5'-C CTG GAA AGC TGA GAT GGA GG-3' (Fragment 225) (SEQ. ID NO:232)
5'-C CTG GAA AGC TGA GAT GGA G-3' (Fragment 226) (SEQ. ID NO:233)
5'-C CTG GAA AGC TGA GAT GGA-3' (Fragment 227) (SEQ. ID NO:234)
5'-C CTG GAA AGC TGA GAT GG-3' (Fragment 228) (SEQ. ID NO:235)
5'-C CTG GAA AGC TGA GAT G-3' (Fragment 229) (SEQ. ID NO:236)
5'-C CTG GAA AGC TGA GAT-3' (Fragment 230) (SEQ. ID NO:237)
5'-C CTG GAA AGC TGA GA-3' (Fragment 231) (SEQ. ID NO:238)
5'-C CTG GAA AGC TGA G-3' (Fragment 232) (SEQ. ID NO:239)
5'-C CTG GAA AGC TGA-3' (Fragment 233) (SEQ. ID NO:240)
5'-C CTG GAA AGC TG-3' (Fragment 234) (SEQ. ID NO:241)
5'-C CTG GAA AGC T-3' (Fragment 235) (SEQ. ID NO:242)
5'-C CTG GAA AGC-3' (Fragment 236) (SEQ. ID NO:243)
5'-CTG GAA AGC TGA GAT GGA GGG CGG CAT GGC GGG CAC AGG CTG GGC-3' (Fragment 237) (SEQ. ID NO:244)
5'-CTG GAA AGC TGA GAT GGA GGG CGG CAT GGC GGG CAC AGG CTG GG-3' (Fragment 238) (SEQ. ID NO:245)
5'-CTG GAA AGC TGA GAT GGA GGG CGG CAT GGC GGG CAC AGG CTG G-3' (Fragment 239) (SEQ. ID NO:246)
5'-CTG GAA AGC TGA GAT GGA GGG CGG CAT GGC GGG CAC AGG CTG-3' (Fragment 240) (SEQ. ID NO:247)

5'-CTG AAA AGC TGA GAT GGA GGG CGG CAT GGC GGG CAC AGG CT-3' (Fragment 241) (SEQ. ID NO:248)
5'-CTG AAA AGC TGA GAT GGA GGG CGG CAT GGC GGG CAC AGG C-3' (Fragment 242) (SEQ. ID NO:249)
5'-CTG AAA AGC TGA GAT GGA GGG CGG CAT GGC GGG CAC AGG-3' (Fragment 243) (SEQ. ID NO:250)
5'-CTG AAA AGC TGA GAT GGA GGG CGG CAT GGC GGG CAC AG-3' (Fragment 244) (SEQ. ID NO:251)
5'-CTG AAA AGC TGA GAT GGA GGG CGG CAT GGC GGG CAC A-3' (Fragment 245) (SEQ. ID NO:252)
5'-CTG AAA AGC TGA GAT GGA GGG CGG CAT GGC GGG CAC-3' (Fragment 246) (SEQ. ID NO:253)
5'-CTG AAA AGC TGA GAT GGA GGG CGG CAT GGC GGG CA-3' (Fragment 247) (SEQ. ID NO:254)
5'-CTG AAA AGC TGA GAT GGA GGG CGG CAT GGC GGG C-3' (Fragment 248) (SEQ. ID NO:255)
5'-CTG AAA AGC TGA GAT GGA GGG CGG CAT GGC GGG-3' (Fragment 249) (SEQ. ID NO:256)
5'-CTG AAA AGC TGA GAT GGA GGG CGG CAT GGC GG-3' (Fragment 250) (SEQ. ID NO:257)
5'-CTG AAA AGC TGA GAT GGA GGG CGG CAT GGC G-3' (Fragment 251) (SEQ. ID NO:258)
5'-CTG AAA AGC TGA GAT GGA GGG CGG CAT GGC-3' (Fragment 252) (SEQ. ID NO:259)
5'-CTG AAA AGC TGA GAT GGA GGG CGG CAT GG-3' (Fragment 253) (SEQ. ID NO:260)
5'-CTG AAA AGC TGA GAT GGA GGG CGG CAT G-3' (Fragment 254) (SEQ. ID NO:261)
5'-CTG AAA AGC TGA GAT GGA GGG CGG CAT-3' (Fragment 255) (SEQ. ID NO:262)
5'-CTG AAA AGC TGA GAT GGA GGG CGG CA-3' (Fragment 256) (SEQ. ID NO:263)
5'-CTG AAA AGC TGA GAT GGA GGG CGG C-3' (Fragment 257) (SEQ. ID NO:264)
5'-CTG AAA AGC TGA GAT GGA GGG CGG-3' (Fragment 258) (SEQ. ID NO:265)
5'-CTG AAA AGC TGA GAT GGA GGG CG-3' (Fragment 259) (SEQ. ID NO:266)
5'-CTG AAA AGC TGA GAT GGA GGG C-3' (Fragment 260) (SEQ. ID NO:267)
5'-CTG AAA AGC TGA GAT GGA GGG-3' (Fragment 261) (SEQ. ID NO:268)
5'-CTG AAA AGC TGA GAT GGA GG-3' (Fragment 262) (SEQ. ID NO:269)
5'-CTG AAA AGC TGA GAT GGA G-3' (Fragment 263) (SEQ. ID NO:270)
5'-CTG AAA AGC TGA GAT GGA-3' (Fragment 264) (SEQ. ID NO:271)
5'-CTG AAA AGC TGA GAT GG-3' (Fragment 265) (SEQ. ID NO:272)
5'-CTG AAA AGC TGA GAT G-3' (Fragment 266) (SEQ. ID NO:273)
5'-CTG AAA AGC TGA GAT-3' (Fragment 267) (SEQ. ID NO:274)
5'-CTG AAA AGC TGA GA-3' (Fragment 268) (SEQ. ID NO:275)
5'-CTG AAA AGC TGA G-3' (Fragment 269) (SEQ. ID NO:276)
5'-CTG AAA AGC TGA-3' (Fragment 270) (SEQ. ID NO:277)
5'-CTG AAA AGC TG-3' (Fragment 271) (SEQ. ID NO:278)
5'-CTG AAA AGC T-3' (Fragment 272) (SEQ. ID NO:279)
5'-TG AAA AGC TGA GAT GGA GGG CGG CAT GGC GGG CAC AGG CTG GGC-3' (Fragment 273) (SEQ. ID NO:280)
5'-TG AAA AGC TGA GAT GGA GGG CGG CAT GGC GGG CAC AGG CTG GG-3' (Fragment 274) (SEQ. ID NO:281)
5'-TG AAA AGC TGA GAT GGA GGG CGG CAT GGC GGG CAC AGG CTG G-3' (Fragment 275) (SEQ. ID NO:282)
5'-TG AAA AGC TGA GAT GGA GGG CGG CAT GGC GGG CAC AGG CTG-3' (Fragment 276) (SEQ. ID NO:283)
5'-TG AAA AGC TGA GAT GGA GGG CGG CAT GGC GGG CAC AGG CT-3' (Fragment 277) (SEQ. ID NO:284)
5'-TG AAA AGC TGA GAT GGA GGG CGG CAT GGC GGG CAC AGG C-3' (Fragment 278) (SEQ. ID NO:285)
5'-TG AAA AGC TGA GAT GGA GGG CGG CAT GGC GGG CAC AGG-3' (Fragment 279) (SEQ. ID NO:286)
5'-TG AAA AGC TGA GAT GGA GGG CGG CAT GGC GGG CAC AG-3' (Fragment 280) (SEQ. ID NO:287)
5'-TG AAA AGC TGA GAT GGA GGG CGG CAT GGC GGG CAC A-3' (Fragment 281) (SEQ. ID NO:288)
5'-TG AAA AGC TGA GAT GGA GGG CGG CAT GGC GGG CAC-3' (Fragment 282) (SEQ. ID NO:289)
5'-TG AAA AGC TGA GAT GGA GGG CGG CAT GGC GGG CA-3' (Fragment 283) (SEQ. ID NO:290)
5'-TG AAA AGC TGA GAT GGA GGG CGG CAT GGC GGG-C3' (Fragment 284) (SEQ. ID NO:291)
5'-TG AAA AGC TGA GAT GGA GGG CGG CAT GGC GGG-3' (Fragment 285) (SEQ. ID NO:292)
5'-TG AAA AGC TGA GAT GGA GGG CGG CAT GGC GG-3' (Fragment 286) (SEQ. ID NO:293)
5'-TG AAA AGC TGA GAT GGA GGG CGG CAT GGC G-3' (Fragment 287) (SEQ. ID NO:294)
5'-TG AAA AGC TGA GAT GGA GGG CGG CAT GGC-3' (Fragment 288) (SEQ. ID NO:295)
5'-TG AAA AGC TGA GAT GGA GGG CGG CAT GG-3' (Fragment 289) (SEQ. ID NO:296)
5'-TG AAA AGC TGA GAT GGA GGG CGG CAT-G3' (Fragment 290) (SEQ. ID NO:297)
5'-TG AAA AGC TGA GAT GGA GGG CGG CAT-3' (Fragment 291) (SEQ. ID NO:298)
5'-TG AAA AGC TGA GAT GGA GGG CGG CA-3' (Fragment 292) (SEQ. ID NO:299)
5'-TG AAA AGC TGA GAT GGA GGG CGG-C3' (Fragment 293) (SEQ. ID NO:300)
5'-TG AAA AGC TGA GAT GGA GGG CGG-3' (Fragment 294) (SEQ. ID NO:301)
5'-TG AAA AGC TGA GAT GGA GGG CG-3' (Fragment 295) (SEQ. ID NO:302)
5'-TG AAA AGC TGA GAT GGA GGG-C3' (Fragment 296) (SEQ. ID NO:303)
5'-TG AAA AGC TGA GAT GGA GGG-3' (Fragment 297) (SEQ. ID NO:304)
5'-TG AAA AGC TGA GAT GGA GG-3' (Fragment 298) (SEQ. ID NO:305)
5'-TG AAA AGC TGA GAT GGA G-3' (Fragment 299) (SEQ. ID NO:306)
5'-TG AAA AGC TGA GAT GGA-3' (Fragment 300) (SEQ. ID NO:307)
5'-TG AAA AGC TGA GAT GG-3' (Fragment 301) (SEQ. ID NO:308)
5'-TG AAA AGC TGA GAT G-3' (Fragment 302) (SEQ. ID NO:309)
5'-TG AAA AGC TGA GAT-3' (Fragment 303) (SEQ. ID NO:310)
5'-TG AAA AGC TGA GA-3' (Fragment 304) (SEQ. ID NO:311)
5'-TG AAA AGC TGA G-3' (Fragment 305) (SEQ. ID NO:312)

5'-TG GAA AGC TGA-3' (Fragment 306) (SEQ. ID NO:313)

5'-TG GAA AGC TG-3' (Fragment 307) (SEQ. ID NO:314)

5'-G GAA AGC TGA GAT GGA GGG CGG CAT GGC GGG CAC AGG CTG GGC-3' (Fragment 308) (SEQ. ID NO:315)

5'-G GAA AGC TGA GAT GGA GGG CGG CAT GGC GGG CAC AGG CTG GG-3' (Fragment 309) (SEQ. ID NO:316)

5'-G GAA AGC TGA GAT GGA GGG CGG CAT GGC GGG CAC AGG CTG G-3' (Fragment 310) (SEQ. ID NO:317)

5'-G GAA AGC TGA GAT GGA GGG CGG CAT GGC GGG CAC AGG CTG-3' (Fragment 311) (SEQ. ID NO:318)

5'-G GAA AGC TGA GAT GGA GGG CGG CAT GGC GGG CAC AGG CT-3' (Fragment 312) (SEQ. ID NO:319)

5'-G GAA AGC TGA GAT GGA GGG CGG CAT GGC GGG CAC AGG C-3' (Fragment 313) (SEQ. ID NO:320)

5'-G GAA AGC TGA GAT GGA GGG CGG CAT GGC GGG CAC AGG-3' (Fragment 314) (SEQ. ID NO:321)

5'-G GAA AGC TGA GAT GGA GGG CGG CAT GGC GGG CAC AG-3' (Fragment 315) (SEQ. ID NO:322)

5'-G GAA AGC TGA GAT GGA GGG CGG CAT GGC GGG CAC A-3' (Fragment 316) (SEQ. ID NO:323)

5'-G GAA AGC TGA GAT GGA GGG CGG CAT GGC GGG CAC-3' (Fragment 317) (SEQ. ID NO:324)

5'-G GAA AGC TGA GAT GGA GGG CGG CAT GGC GGG CA-3' (Fragment 318) (SEQ. ID NO:325)

5'-G GAA AGC TGA GAT GGA GGG CGG CAT GGC GGG C-3' (Fragment 319) (SEQ. ID NO:326)

5'-G GAA AGC TGA GAT GGA GGG CGG CAT GGC GGG-3' (Fragment 320) (SEQ. ID NO:327)

5'-G GAA AGC TGA GAT GGA GGG CGG CAT GGC GG-3' (Fragment 321) (SEQ. ID NO:328)

5'-G GAA AGC TGA GAT GGA GGG CGG CAT GGC G-3' (Fragment 322) (SEQ. ID NO:329)

5'-G GAA AGC TGA GAT GGA GGG CGG CAT GGC-3' (Fragment 323) (SEQ. ID NO:330)

5'-G GAA AGC TGA GAT GGA GGG CGG CAT GG-3' (Fragment 324) (SEQ. ID NO:331)

5'-G GAA AGC TGA GAT GGA GGG CGG CAT G-3' (Fragment 325) (SEQ. ID NO:332)

5'-G GAA AGC TGA GAT GGA GGG CGG CAT-3' (Fragment 326) (SEQ. ID NO:333)

5'-G GAA AGC TGA GAT GGA GGG CGG CA-3' (Fragment 327) (SEQ. ID NO:334)

5'-G GAA AGC TGA GAT GGA GGG CGG C-3' (Fragment 328) (SEQ. ID NO:335)

5'-G GAA AGC TGA GAT GGA GGG CGG-3' (Fragment 329) (SEQ. ID NO:336)

5'-G GAA AGC TGA GAT GGA GGG CG-3' (Fragment 330) (SEQ. ID NO:337)

5'-G GAA AGC TGA GAT GGA GGG C-3' (Fragment 331) (SEQ. ID NO:338)

5'-G GAA AGC TGA GAT GGA GGG-3' (Fragment 332) (SEQ. ID NO:339)

5'-G GAA AGC TGA GAT GGA GG-3' (Fragment 333) (SEQ. ID NO:340)

5'-G GAA AGC TGA GAT GGA G-3' (Fragment 334) (SEQ. ID NO:341)

5'-G GAA AGC TGA GAT GGA-3' (Fragment 335) (SEQ. ID NO:342)

5'-G GAA AGC TGA GAT GG-3' (Fragment 336) (SEQ. ID NO:343)

5'-G GAA AGC TGA GAT G-3' (Fragment 337) (SEQ. ID NO:344)

5'-G GAA AGC TGA GAT-3' (Fragment 338) (SEQ. ID NO:345)

5'-G GAA AGC TGA GA-3' (Fragment 339) (SEQ. ID NO:346)

5'-G GAA AGC TGA G-3' (Fragment 340) (SEQ. ID NO:347)

5'-G GAA AGC TGA-3' (Fragment 341) (SEQ. ID NO:348)

5'-GAA AGC TGA GAT GGA GGG CGG CAT GGC GGG CAC AGG CTG GGC-3' (Fragment 342) (SEQ. ID NO:349)

5'-GAA AGC TGA GAT GGA GGG CGG CAT GGC GGG CAC AGG CTG GG-3' (Fragment 343) (SEQ. ID NO:350)

5'-GAA AGC TGA GAT GGA GGG CGG CAT GGC GGG CAC AGG CTG G-3' (Fragment 344) (SEQ. ID NO:351)

5'-GAA AGC TGA GAT GGA GGG CGG CAT GGC GGG CAC AGG CTG-3' (Fragment 345) (SEQ. ID NO:352)

5'-GAA AGC TGA GAT GGA GGG CGG CAT GGC GGG CAC AGG CT-3' (Fragment 346) (SEQ. ID NO:353)

5'-GAA AGC TGA GAT GGA GGG CGG CAT GGC GGG CAC AGG C-3' (Fragment 347) (SEQ. ID NO:354)

5'-GAA AGC TGA GAT GGA GGG CGG CAT GGC GGG CAC AGG-3' (Fragment 348) (SEQ. ID NO:355)

5'-GAA AGC TGA GAT GGA GGG CGG CAT GGC GGG CAC AG-3' (Fragment 349) (SEQ. ID NO:356)

5'-GAA AGC TGA GAT GGA GGG CGG CAT GGC GGG CAC A-3' (Fragment 350) (SEQ. ID NO:357)

5'-GAA AGC TGA GAT GGA GGG CGG CAT GGC GGG CAC-3' (Fragment 351) (SEQ. ID NO:358)

5'-GAA AGC TGA GAT GGA GGG CGG CAT GGC GGG CA-3' (Fragment 352) (SEQ. ID NO:359)

5'-GAA AGC TGA GAT GGA GGG CGG CAT GGC GGG C-3' (Fragment 353) (SEQ. ID NO:360)

5'-GAA AGC TGA GAT GGA GGG CGG CAT GGC GGG-3' (Fragment 354) (SEQ. ID NO:361)

5'-GAA AGC TGA GAT GGA GGG CGG CAT GGC GG-3' (Fragment 355) (SEQ. ID NO:362)

5'-GAA AGC TGA GAT GGA GGG CGG CAT GGC G-3' (Fragment 356) (SEQ. ID NO:363)

5'-GAA AGC TGA GAT GGA GGG CGG CAT GGC-3' (Fragment 357) (SEQ. ID NO:364)

5'-GAA AGC TGA GAT GGA GGG CGG CAT GG-3' (Fragment 358) (SEQ. ID NO:365)

5'-GAA AGC TGA GAT GGA GGG CGG CAT G-3' (Fragment 359) (SEQ. ID NO:366)

5'-GAA AGC TGA GAT GGA GGG CGG CAT-3' (Fragment 360) (SEQ. ID NO:367)

5'-GAA AGC TGA GAT GGA GGG CGG CA-3' (Fragment 361) (SEQ. ID NO:368)

5'-GAA AGC TGA GAT GGA GGG CGG C-3' (Fragment 362) (SEQ. ID NO:369)

5'-GAA AGC TGA GAT GGA GGG CGG-3' (Fragment 363) (SEQ. ID NO:370)

5'-GAA AGC TGA GAT GGA GGG CG-3' (Fragment 364) (SEQ. ID NO:371)

5'-GAA AGC TGA GAT GGA GGG C-3' (Fragment 365) (SEQ. ID NO:372)

5'-GAA AGC TGA GAT GGA GGG-3' (Fragment 366) (SEQ. ID NO:373)

5'-GAA AGC TGA GAT GGA GG-3' (Fragment 367) (SEQ. ID NO:374)

5'-GAA AGC TGA GAT GGA G-3' (Fragment 368) (SEQ. ID NO:375)

5'-GAA AGC TGA GAT GGA-3' (Fragment 369) (SEQ. ID NO:376)

5'-GAA AGC TGA GAT GG-3' (Fragment 370) (SEQ. ID NO:377)

5'-GAA AGC TGA GAT G-3' (Fragment 371) (SEQ. ID NO:378)
5'-GAA AGC TGA GAT-3' (Fragment 372) (SEQ. ID NO:379)
5'-GAA AGC TGA GA-3' (Fragment 373) (SEQ. ID NO:380)
5'-GAA AGC TGA G-3' (Fragment 374) (SEQ. ID NO:381)
5'-AA AGC TGA GAT GGA GGG CGG CAT GGC GGG CAC AGG CTG GGC-3' (Fragment 375) (SEQ. ID NO:382)
5'-AA AGC TGA GAT GGA GGG CGG CAT GGC GGG CAC AGG CTG GG-3' (Fragment 376) (SEQ. ID NO:383)
5'-AA AGC TGA GAT GGA GGG CGG CAT GGC GGG CAC AGG CTG G-3' (Fragment 377) (SEQ. ID NO:384)
5'-AA AGC TGA GAT GGA GGG CGG CAT GGC GGG CAC AGG CTG-3' (Fragment 378) (SEQ. ID NO:385)
5'-AA AGC TGA GAT GGA GGG CGG CAT GGC GGG CAC AGG CT-3' (Fragment 379) (SEQ. ID NO:386)
5'-AA AGC TGA GAT GGA GGG CGG CAT GGC GGG CAC AGG C-3' (Fragment 380) (SEQ. ID NO:387)
5'-AA AGC TGA GAT GGA GGG CGG CAT GGC GGG CAC AGG-3' (Fragment 381) (SEQ. ID NO:388)
5'-AA AGC TGA GAT GGA GGG CGG CAT GGC GGG CAC AG-3' (Fragment 382) (SEQ. ID NO:389)
5'-AA AGC TGA GAT GGA GGG CGG CAT GGC GGG CAC A-3' (Fragment 383) (SEQ. ID NO:390)
5'-AA AGC TGA GAT GGA GGG CGG CAT GGC GGG CAC-3' (Fragment 384) (SEQ. ID NO:391)
5'-AA AGC TGA GAT GGA GGG CGG CAT GGC GGG CA-3' (Fragment 385) (SEQ. ID NO:392)
5'-AA AGC TGA GAT GGA GGG CGG CAT GGC GGG C-3' (Fragment 386) (SEQ. ID NO:393)
5'-AA AGC TGA GAT GGA GGG CGG CAT GGC GGG-3' (Fragment 387) (SEQ. ID NO:394)
5'-AA AGC TGA GAT GGA GGG CGG CAT GGC GG-3' (Fragment 388) (SEQ. ID NO:395)
5'-AA AGC TGA GAT GGA GGG CGG CAT GGC G-3' (Fragment 389) (SEQ. ID NO:396)
5'-AA AGC TGA GAT GGA GGG CGG CAT GGC-3' (Fragment 390) (SEQ. ID NO:397)
5'-AA AGC TGA GAT GGA GGG CGG CAT GG-3' (Fragment 391) (SEQ. ID NO:398)
5'-AA AGC TGA GAT GGA GGG CGG CAT G-3' (Fragment 392) (SEQ. ID NO:399)
5'-AA AGC TGA GAT GGA GGG CGG CAT-3' (Fragment 393) (SEQ. ID NO:400)
5'-AA AGC TGA GAT GGA GGG CGG CA-3' (Fragment 394) (SEQ. ID NO:401)
5'-AA AGC TGA GAT GGA GGG CGG C-3' (Fragment 395) (SEQ. ID NO:402)
5'-AA AGC TGA GAT GGA GGG CGG-3' (Fragment 396) (SEQ. ID NO:403)
5'-AA AGC TGA GAT GGA GGG CG-3' (Fragment 397) (SEQ. ID NO:404)
5'-AA AGC TGA GAT GGA GGG C-3' (Fragment 398) (SEQ. ID NO:405)
5'-AA AGC TGA GAT GGA GGG-3' (Fragment 399) (SEQ. ID NO:406)
5'-AA AGC TGA GAT GGA GG-3' (Fragment 400) (SEQ. ID NO:407)
5'-AA AGC TGA GAT GGA G-3' (Fragment 401) (SEQ. ID NO:408)
5'-AA AGC TGA GAT GGA-3' (Fragment 402) (SEQ. ID NO:409)
5'-AA AGC TGA GAT GG-3' (Fragment 403) (SEQ. ID NO:410)
5'-AA AGC TGA GAT G-3' (Fragment 404) (SEQ. ID NO:411)
5'-AA AGC TGA GAT-3' (Fragment 405) (SEQ. ID NO:412)
5'-AA AGC TGA GA-3' (Fragment 406) (SEQ. ID NO:413)
5'-A AGC TGA GAT GGA GGG CGG CAT GGC GGG CAC AGG CTG GGC-3' (Fragment 407) (SEQ. ID NO:414)
5'-A AGC TGA GAT GGA GGG CGG CAT GGC GGG CAC AGG CTG GG-3' (Fragment 408) (SEQ. ID NO:415)
5'-A AGC TGA GAT GGA GGG CGG CAT GGC GGG CAC AGG CTG G-3' (Fragment 409) (SEQ. ID NO:416)
5'-A AGC TGA GAT GGA GGG CGG CAT GGC GGG CAC AGG CTG-3' (Fragment 410) (SEQ. ID NO:417)
5'-A AGC TGA GAT GGA GGG CGG CAT GGC GGG CAC AGG CT-3' (Fragment 411) (SEQ. ID NO:418)
5'-A AGC TGA GAT GGA GGG CGG CAT GGC GGG CAC AGG C-3' (Fragment 412) (SEQ. ID NO:419)
5'-A AGC TGA GAT GGA GGG CGG CAT GGC GGG CAC AGG-3' (Fragment 413) (SEQ. ID NO:420)
5'-A AGC TGA GAT GGA GGG CGG CAT GGC GGG CAC AG-3' (Fragment 414) (SEQ. ID NO:421)
5'-A AGC TGA GAT GGA GGG CGG CAT GGC GGG CAC A-3' (Fragment 415) (SEQ. ID NO:422)
5'-A AGC TGA GAT GGA GGG CGG CAT GGC GGG CAC-3' (Fragment 416) (SEQ. ID NO:423)
5'-A AGC TGA GAT GGA GGG CGG CAT GGC GGG CA-3' (Fragment 417) (SEQ. ID NO:424)
5'-A AGC TGA GAT GGA GGG CGG CAT GGC GGG C-3' (Fragment 418) (SEQ. ID NO:425)
5'-A AGC TGA GAT GGA GGG CGG CAT GGC GGG-3' (Fragment 419) (SEQ. ID NO:426)
5'-A AGC TGA GAT GGA GGG CGG CAT GGC GG-3' (Fragment 420) (SEQ. ID NO:427)
5'-A AGC TGA GAT GGA GGG CGG CAT GGC G-3' (Fragment 421) (SEQ. ID NO:428)
5'-A AGC TGA GAT GGA GGG CGG CAT GGC-3' (Fragment 422) (SEQ. ID NO:429)
5'-A AGC TGA GAT GGA GGG CGG CAT GG-3' (Fragment 423) (SEQ. ID NO:430)
5'-A AGC TGA GAT GGA GGG CGG CAT G-3' (Fragment 424) (SEQ. ID NO:431)
5'-A AGC TGA GAT GGA GGG CGG CAT-3' (Fragment 425) (SEQ. ID NO:432)
5'-A AGC TGA GAT GGA GGG CGG CA-3' (Fragment 426) (SEQ. ID NO:433)
5'-A AGC TGA GAT GGA GGG CGG C-3' (Fragment 427) (SEQ. ID NO:434)
5'-A AGC TGA GAT GGA GGG CGG-3' (Fragment 428) (SEQ. ID NO:435)
5'-A AGC TGA GAT GGA GGG CG-3' (Fragment 429) (SEQ. ID NO:436)
5'-A AGC TGA GAT GGA GGG C-3' (Fragment 430) (SEQ. ID NO:437)
5'-A AGC TGA GAT GGA GGG-3' (Fragment 431) (SEQ. ID NO:438)
5'-A AGC TGA GAT GGA GG-3' (Fragment 432) (SEQ. ID NO:439)
5'-A AGC TGA GAT GGA G-3' (Fragment 433) (SEQ. ID NO:440)
5'-A AGC TGA GAT GGA-3' (Fragment 434) (SEQ. ID NO:441)
5'-A AGC TGA GAT GG-3' (Fragment 435) (SEQ. ID NO:442)
5'-A AGC TGA GAT G-3' (Fragment 436) (SEQ. ID NO:443)
5'-A AGC TGA GAT-3' (Fragment 437) (SEQ. ID NO:444)

5'-AGC TGA GAT GGA GGG CGG CAT GGC GGG CAC AGG CTG GGC-3' (Fragment 438) (SEQ. ID NO:445)
5'-AGC TGA GAT GGA GGG CGC CAT GGC GGG CAC AGG CTG GG-3' (Fragment 439) (SEQ. ID NO:446)
5'-AGC TGA GAT GGA GGG CGG CAT GGC GGG CAC AGG CTG G-3' (Fragment 440) (SEQ. ID NO:447)
5'-AGC TGA GAT GGA GGG CGG CAT GGC GGG CAC AGG CTG-3' (Fragment 441) (SEQ. ID NO:448)
5'-AGC TGA GAT GGA GGG CGG CAT GGC GGG CAC AGG CT-3' (Fragment 442) (SEQ. ID NO:449)
5'-AGC TGA GAT GGA GGG CGG CAT GGC GGG CAC AGG C-3' (Fragment 443) (SEQ. ID NO:450)
5'-AGC TGA GAT GGA GGG CGG CAT GGC GGG CAC AGG-3' (Fragment 444) (SEQ. ID NO:451)
5'-AGC TGA GAT GGA GGG CGG CAT GGC GGG CAC AG-3' (Fragment 445) (SEQ. ID NO:452)
5'-AGC TGA GAT GGA GGG CGG CAT GGC GGG CAC A-3' (Fragment 446) (SEQ. ID NO:453)
5'-AGC TGA GAT GGA GGG CGG CAT GGC GGG CAC-3' (Fragment 447) (SEQ. ID NO:454)
5'-AGC TGA GAT GGA GGG CGG CAT GGC GGG CA-3' (Fragment 448) (SEQ. ID NO:455)
5'-AGC TGA GAT GGA GGG CGG CAT GGC GGG C-3' (Fragment 449) (SEQ. ID NO:456)
5'-AGC TGA GAT GGA GGG CGG CAT GGC GGG-3' (Fragment 450) (SEQ. ID NO:457)
5'-AGC TGA GAT GGA GGG CGG CAT GGC GG-3' (Fragment 451) (SEQ. ID NO:458)
5'-AGC TGA GAT GGA GGG CGG CAT GGC G-3' (Fragment 452) (SEQ. ID NO:459)
5'-AGC TGA GAT GGA GGG CGG CAT GGC-3' (Fragment 453) (SEQ. ID NO:460)
5'-AGC TGA GAT GGA GGG CGG CAT GG-3' (Fragment 454) (SEQ. ID NO:461)
5'-AGC TGA GAT GGA GGG CGG CAT G-3' (Fragment 455) (SEQ. ID NO:462)
5'-AGC TGA GAT GGA GGG CGG CAT-3' (Fragment 456) (SEQ. ID NO:463)
5'-AGC TGA GAT GGA GGG CGG CA-3' (Fragment 457) (SEQ. ID NO:464)
5'-AGC TGA GAT GGA GGG CGG C-3' (Fragment 458) (SEQ. ID NO:465)
5'-AGC TGA GAT GGA GGG CGG-3' (Fragment 459) (SEQ. ID NO:466)
5'-AGC TGA GAT GGA GGG CG-3' (Fragment 460) (SEQ. ID NO:467)
5'-AGC TGA GAT GGA GGG-C3' (Fragment 461) (SEQ. ID NO:468)
5'-AGC TGA GAT GGA GGG-3' (Fragment 462) (SEQ. ID NO:469)
5'-AGC TGA GAT GGA GG-3' (Fragment 463) (SEQ. ID NO:470)
5'-AGC TGA GAT GGA G-3' (Fragment 464) (SEQ. ID NO:471)
5'-AGC TGA GAT GGA-3' (Fragment 465) (SEQ. ID NO:472)
5'-AGC TGA GAT GG-3' (Fragment 466) (SEQ. ID NO:473)
5'-AGC TGA GAT G-3' (Fragment 467) (SEQ. ID NO:474)
5'-GC TGA GAT GGA GGG CGG CAT GGC GGG CAC AGG CTG GGG-3' (Fragment 468) (SEQ. ID NO:475)
5'-GC TGA GAT GGA GGG CGG CAT GGC GGG CAC AGG CTG GG-3' (Fragment 469) (SEQ. ID NO:476)
5'-GC TGA GAT GGA GGG CGG CAT GGC GGG CAC AGG CTG G-3' (Fragment 470) (SEQ. ID NO:477)
5'-GC TGA GAT GGA GGG CGG CAT GGC GGG CAC AGG CTG-3' (Fragment 471) (SEQ. ID NO:478)
5'-GC TGA GAT GGA GGG CGG CAT GGC GGG CAC AGG CT-3' (Fragment 472) (SEQ. ID NO:479)
5'-GC TGA GAT GGA GGG CGG CAT GGC GGG CAC AGG C-3' (Fragment 473) (SEQ. ID NO:480)
5'-GC TGA GAT GGA GGG CGG CAT GGC GGG CAC AGG-3' (Fragment 474) (SEQ. ID NO:481)
5'-GC TGA GAT GGA GGG CGG CAT GGC GGG CAC AG-3' (Fragment 475) (SEQ. ID NO:482)
5'-GC TGA GAT GGA GGG CGG CAT GGC GGG CAC A-3' (Fragment 476) (SEQ. ID NO:483)
5'-GC TGA GAT GGA GGG CGG CAT GGC GGG CAC-3' (Fragment 477) (SEQ. ID NO:484)
5'-GC TGA GAT GGA GGG CGG CAT GGC GGG CA-3' (Fragment 478) (SEQ. ID NO:485)
5'-GC TGA GAT GGA GGG CGG CAT GGC GGG C-3' (Fragment 479) (SEQ. ID NO:486)
5'-GC TGA GAT GGA GGG CGG CAT GGC GGG-3' (Fragment 480) (SEQ. ID NO:487)
5'-GC TGA GAT GGA GGG CGG CAT GGC GG-3' (Fragment 481) (SEQ. ID NO:488)
5'-GC TGA GAT GGA GGG CGG CAT GGC G-3' (Fragment 482) (SEQ. ID NO:489)
5'-GC TGA GAT GGA GGG CGG CAT GGC-3' (Fragment 483) (SEQ. ID NO:490)
5'-GC TGA GAT GGA GGG CGG CAT GG-3' (Fragment 484) (SEQ. ID NO:491)
5'-GC TGA GAT GGA GGG CGG CAT G-3' (Fragment 485) (SEQ. ID NO:492)
5'-GC TGA GAT GGA GGG CGG CAT-3' (Fragment 486) (SEQ. ID NO:493)
5'-GC TGA GAT GGA GGG CGG CA-3' (Fragment 487) (SEQ. ID NO:494)
5'-GC TGA GAT GGA GGG CGG C-3' (Fragment 488) (SEQ. ID NO:495)
5'-GC TGA GAT GGA GGG CGG-3' (Fragment 489) (SEQ. ID NO:496)
5'-GC TGA GAT GGA GGG CG-3' (Fragment 490) (SEQ. ID NO:497)
5'-GC TGA GAT GGA GGG C-3' (Fragment 491) (SEQ. ID NO:498)
5'-GC TGA GAT GGA GGG-3' (Fragment 492) (SEQ. ID NO:499)
5'-GC TGA GAT GGA GG-3' (Fragment 493) (SEQ. ID NO:500)
5'-GC TGA GAT GGA G-3' (Fragment 494) (SEQ. ID NO:501)
5'-GC TGA GAT GGA-3' (Fragment 495) (SEQ. ID NO:502)
5'-GC TGA GAT GG-3' (Fragment 496) (SEQ. ID NO:503)
5'-CTGA GAT GGA GGG CGG CAT GGC GGG CAC AGG CTG GGC-3' (Fragment 497) (SEQ. ID NO:504)
5'-CTGA GAT GGA GGG CGG CAT GGC GGG CAC AGG CTG GG-3' (Fragment 498) (SEQ. ID NO:505)
5'-CTGA GAT GGA GGG CGG CAT GGC GGG CAC AGG CTG G-3' (Fragment 499) (SEQ. ID NO:506)
5'-CTGA GAT GGA GGG CGG CAT GGC GGG CAC AGG CTG-3' (Fragment 500) (SEQ. ID NO:507)
5'-CTGA GAT GGA GGG CGG CAT GGC GGG CAC AGG CT-3' (Fragment 501) (SEQ. ID NO:508)
5'-CTGA GAT GGA GGG CGG CAT GGC GGG CAC AGG C-3' (Fragment 502) (SEQ. ID NO:509)
5'-CTGA GAT GGA GGG CGG CAT GGC GGG CAC AGG-3' (Fragment 503) (SEQ. ID NO:510)
5'-CTGA GAT GGA GGG CGG CAT GGC GGG CAC AG-3' (Fragment 504) (SEQ. ID NO:511)
5'-CTGA GAT GGA GGG CGG CAT GGC GGG CAC A-3' (Fragment 505) (SEQ. ID NO:512)

5'-CTGA GAT GGA GGG CGG CAT GGC GGG CAC-3' (Fragment 506) (SEQ. ID NO:513)
5'-CTGA GAT GGA GGG CGG CAT GGC GGG CA-3' (Fragment 507) (SEQ. ID NO:514)
5'-CTGA GAT GGA GGG CGG CAT GGC GGG C-3' (Fragment 508) (SEQ. ID NO:515)
5'-CTGA GAT GGA GGG CGG CAT GGC GGG-3' (Fragment 509) (SEQ. ID NO:516)
5'-CTGA GAT GGA GGG CGG CAT GGC GG-3' (Fragment 510) (SEQ. ID NO:517)
5'-CTGA GAT GGA GGG CGG CAT GGC G-3' (Fragment 511) (SEQ. ID NO:518)
5'-CTGA GAT GGA GGG CGG CAT GGC-3' (Fragment 512) (SEQ. ID NO:519)
5'-CTGA GAT GGA GGG CGG CAT GG-3' (Fragment 513) (SEQ. ID NO:520)
5'-CTGA GAT GGA GGG CGG CAT G-3' (Fragment 514) (SEQ. ID NO:521)
5'-CTGA GAT GGA GGG CGG CAT-3' (Fragment 515) (SEQ. ID NO:522)
5'-CTGA GAT GGA GGG CGG CA-3' (Fragment 516) (SEQ. ID NO:523)
5'-CTGA GAT GGA GGG CGG C-3' (Fragment 517) (SEQ. ID NO:524)
5'-CTGA GAT GGA GGG CGG-3' (Fragment 518) (SEQ. ID NO:525)
5'-CTGA GAT GGA GGG CG-3' (Fragment 519) (SEQ. ID NO:526)
5'-CTGA GAT GGA GGG C-3' (Fragment 520) (SEQ. ID NO:527)
5'-CTGA GAT GGA GGG-3' (Fragment 521) (SEQ. ID NO:528)
5'-CTGA GAT GGA GG-3' (Fragment 522) (SEQ. ID NO:529)
5'-CTGA GAT GGA G-3' (Fragment 523) (SEQ. ID NO:530)
5'-CTGA GAT GGA-3' (Fragment 524) (SEQ. ID NO:531)
5'-TGA GAT GGA GGG CGG CAT GGC GGG CAC AGG CTG GGC-3' (Fragment 525) (SEQ. ID NO:532)
5'-TGA GAT GGA GGG CGG CAT GGC GGG CAC AGG CTG GG-3' (Fragment 526) (SEQ. ID NO:533) 5'-TGA GAT GGA GGG CGG CAT GGC GGG CAC AGG CTG G-3' (Fragment 527) (SEQ. ID NO:534)
5'-TGA GAT GGA GGG CGG CAT GGC GGG CAC AGG CTG-3' (Fragment 528) (SEQ. ID NO:535)
5'-TGA GAT GGA GGG CGG CAT GGC GGG CAC AGG CT-3' (Fragment 529) (SEQ. ID NO:536)
5'-TGA GAT GGA GGG CGG CAT GGC GGG CAC AGG C-3' (Fragment 530) (SEQ. ID NO:537)
5'-TGA GAT GGA GGG CGG CAT GGC GGG CAC AGG-3' (Fragment 531) (SEQ. ID NO:538)
5'-TGA GAT GGA GGG CGG CAT GGC GGG CAC AG-3' (Fragment 532) (SEQ. ID NO:539)
5'-TGA GAT GGA GGG CGG CAT GGC GGG CAC A-3' (Fragment 533) (SEQ. ID NO:540)
5'-TGA GAT GGA GGG CGG CAT GGC GGG CAC-3' (Fragment 534) (SEQ. ID NO:541)
5'-TGA GAT GGA GGG CGG CAT GGC GGG CA-3' (Fragment 535) (SEQ. ID NO:542)
5'-TGA GAT GGA GGG CGG CAT GGC GGG C-3' (Fragment 536) (SEQ. ID NO:543)
5'-TGA GAT GGA GGG CGG CAT GGC GGG-3' (Fragment 537) (SEQ. ID NO:544)
5'-TGA GAT GGA GGG CGG CAT GGC GG-3' (Fragment 538) (SEQ. ID NO:545)
5'-TGA GAT GGA GGG CGG CAT GGC G-3' (Fragment 539) (SEQ. ID NO:546)
5'-TGA GAT GGA GGG CGG CAT GGC-3' (Fragment 540) (SEQ. ID NO:547)
5'-TGA GAT GGA GGG CGG CAT GG-3' (Fragment 541) (SEQ. ID NO:548)
5'-TGA GAT GGA GGG CGG CAT G-3' (Fragment 542) (SEQ. ID NO:549)
5'-TGA GAT GGA GGG CGG CAT-3' (Fragment 543) (SEQ. ID NO:550)
5'-TGA GAT GGA GGG CGG CA-3' (Fragment 544) (SEQ. ID NO:551)
5'-TGA GAT GGA GGG CGG C-3' (Fragment 545) (SEQ. ID NO:552)
5'-TGA GAT GGA GGG CGG-3' (Fragment 546) (SEQ. ID NO:553)
5'-TGA GAT GGA GGG CG-3' (Fragment 547) (SEQ. ID NO:554)
5'-TGA GAT GGA GGG C-3' (Fragment 548) (SEQ. ID NO:555)
5'-TGA GAT GGA GGG-3' (Fragment 549) (SEQ. ID NO:556)
5'-TGA GAT GGA GG-3' (Fragment 550) (SEQ. ID NO:557)
5'-TGA GAT GGA G-3' (Fragment 551) (SEQ. ID NO:558)
5'-GA GAT GGA GGG CGG CAT GGC GGG CAC AGG CTG GGC-3' (Fragment 552) (SEQ ID NO:559) 5'-GA GAT GGA GGG CGG CAT GGC GGG CAC AGG CTG GG-3' (Fragment 553) (SEQ ID NO:560)
5'-GA GAT GGA GGG CGG CAT GGC GGG CAC AGG CTG G-3' (Fragment 554) (SEQ ID NO:561)
5'-GA GAT GGA GGG CGG CAT GGC GGG CAC AGG CTG-3' (Fragment 555) (SEQ ID NO:562)
5'-GA GAT GGA GGG CGG CAT GGC GGG CAC AGG CT-3' (Fragment 556) (SEQ ID NO:563)
5'-GA GAT GGA GGG CGG CAT GGC GGG CAC AGG C-3' (Fragment 557) (SEQ ID NO:564)
5'-GA GAT GGA GGG CGG CAT GGC GGG CAC AGG-3' (Fragment 558) (SEQ ID NO:565)
5'-GA GAT GGA GGG CGG CAT GGC GGG CAC AG-3' (Fragment 559) (SEQ ID NO:566)
5'-GA GAT GGA GGG CGG CAT GGC GGG CAC A-3' (Fragment 560) (SEQ ID NO:567)
5'-GA GAT GGA GGG CGG CAT GGC GGG CAC-3' (Fragment 561) (SEQ ID NO:568)
5'-GA GAT GGA GGG CGG CAT GGC GGG CA-3' (Fragment 562) (SEQ ID NO:569)
5'-GA GAT GGA GGG CGG CAT GGC GGG C-3' (Fragment 563) (SEQ ID NO:570)
5'-GA GAT GGA GGG CGG CAT GGC GGG-3' (Fragment 564) (SEQ ID NO:571)
5'-GA GAT GGA GGG CGG CAT GGC GG-3' (Fragment 565) (SEQ ID NO:572)
5'-GA GAT GGA GGG CGG CAT GGC G-3' (Fragment 566) (SEQ ID NO:573)
5'-GA GAT GGA GGG CGG CAT GGC-3' (Fragment 567) (SEQ ID NO:574)
5'-GA GAT GGA GGG CGG CAT GG-3' (Fragment 568) (SEQ ID NO:575)
5'-GA GAT GGA GGG CGG CAT G-3' (Fragment 569) (SEQ ID NO:576)
5'-GA GAT GGA GGG CGG CAT-3' (Fragment 570) (SEQ ID NO:577)
5'-GA GAT GGA GGG CGG CA-3' (Fragment 571) (SEQ ID NO:578)
5'-GA GAT GGA GGG CGG C-3' (Fragment 572) (SEQ ID NO:579)
5'-GA GAT GGA GGG CGG-3' (Fragment 573) (SEQ ID NO:580)

5'-GA GAT GGA GGG CG-3' (Fragment 574) (SEQ ID NO:581)
5'-GA GAT GGA GGG C-3' (Fragment 575) (SEQ ID NO:582)
5'-GA GAT GGA GGG-3' (Fragment 576) (SEQ ID NO:583)
5'-GA GAT GGA GG-3' (Fragment 577) (SEQ ID NO:584)
5'-A GAT GGA GGG CGG CAT GGC GGG CAC AGG CTG GGC-3' (Fragment 578) (SEQ. ID NO:585)
5'-A GAT GGA GGG CGG CAT GGC GGG CAC AGG CTG GG-3' (Fragment 579) (SEQ. ID NO:586)
5'-A GAT GGA GGG CGG CAT GGC GGG CAC AGG CTG G-3' (Fragment 580) (SEQ. ID NO:587)
5'-A GAT GGA GGG CGG CAT GGC GGG CAC AGG CTG-3' (Fragment 581) (SEQ. ID NO:588)
5'-A GAT GGA GGG CGG CAT GGC GGG CAC AGG CT-3' (Fragment 582) (SEQ. ID NO:589)
5'-A GAT GGA GGG CGG CAT GGC GGG CAC AGG C-3' (Fragment 583) (SEQ. ID NO:590)
5'-A GAT GGA GGG CGG CAT GGC GGG CAC AGG-3' (Fragment 584) (SEQ. ID NO:591)
5'-A GAT GGA GGG CGG CAT GGC GGG CAC AG-3' (Fragment 585) (SEQ. ID NO:592)
5'-A GAT GGA GGG CGG CAT GGC GGG CAC A-3' (Fragment 586) (SEQ. ID NO:593)
5'-A GAT GGA GGG CGG CAT GGC GGG CAC-3' (Fragment 587) (SEQ. ID NO:594)
5'-A GAT GGA GGG CGG CAT GGC GGG CA-3' (Fragment 588) (SEQ. ID NO:595)
5'-A GAT GGA GGG CGG CAT GGC GGG C-3' (Fragment 589) (SEQ. ID NO:596)
5'-A GAT GGA GGG CGG CAT GGC GGG-3' (Fragment 590) (SEQ. ID NO:597)
5'-A GAT GGA GGG CGG CAT GGC GG-3' (Fragment 591) (SEQ. ID NO:598)
5'-A GAT GGA GGG CGG CAT GGC G-3' (Fragment 592) (SEQ. ID NO:599)
5'-A GAT GGA GGG CGG CAT GGC-3' (Fragment 593) (SEQ. ID NO:600)
5'-A GAT GGA GGG CGG CAT GG-3' (Fragment 594) (SEQ. ID NO:601)
5'-A GAT GGA GGG CGG CAT G-3' (Fragment 595) (SEQ. ID NO:602)
5'-A GAT GGA GGG CGG CAT-3' (Fragment 596) (SEQ. ID NO:603)
5'-A GAT GGA GGG CGG CA-3' (Fragment 597) (SEQ. ID NO:604)
5'-A GAT GGA GGG CGG C-3' (Fragment 598) (SEQ. ID NO:605)
5'-A GAT GGA GGG CGG-3' (Fragment 599) (SEQ. ID NO:606)
5'-A GAT GGA GGG CG-3' (Fragment 600) (SEQ. ID NO:607)
5'-A GAT GGA GGG C-3' (Fragment 601) (SEQ. ID NO:608)
5'-A GAT GGA GGG-3' (Fragment 602) (SEQ. ID NO:609)
5'-GAT GGA GGG CGG CAT GGC GGG CAC AGG CTG GGC-3' (Fragment 603) (SEQ. ID NO:610)
5'-GAT GGA GGG CGG CAT GGC GGG CAC AGG CTG GG-3' (Fragment 604) (SEQ. ID NO:611)
5'-GAT GGA GGG CGG CAT GGC GGG CAC AGG CTG G-3' (Fragment 605) (SEQ. ID NO:612)
5'-GAT GGA GGG CGG CAT GGC GGG CAC AGG CTG-3' (Fragment 606) (SEQ. ID NO:613)
5'-GAT GGA GGG CGG CAT GGC GGG CAC AGG CT-3' (Fragment 607) (SEQ. ID NO:614)
5'-GAT GGA GGG CGG CAT GGC GGG CAC AGG C-3' (Fragment 608) (SEQ. ID NO:615)
5'-GAT GGA GGG CGG CAT GGC GGG CAC AGG-3' (Fragment 609) (SEQ. ID NO:616)
5'-GAT GGA GGG CGG CAT GGC GGG CAC AG-3' (Fragment 610) (SEQ. ID NO:617)
5'-GAT GGA GGG CGG CAT GGC GGG CAC A-3' (Fragment 611) (SEQ. ID NO:618)
5'-GAT GGA GGG CGG CAT GGC GGG CAC-3' (Fragment 612) (SEQ. ID NO:619)
5'-GAT GGA GGG CGG CAT GGC GGG CA-3' (Fragment 613) (SEQ. ID NO:620)
5'-GAT GGA GGG CGG CAT GGC GGG C-3' (Fragment 614) (SEQ. ID NO:621)
5'-GAT GGA GGG CGG CAT GGC GGG-3' (Fragment 615) (SEQ. ID NO:622)
5'-GAT GGA GGG CGG CAT GGC GG-3' (Fragment 616) (SEQ. ID NO:623)
5'-GAT GGA GGG CGG CAT GGC G-3' (Fragment 617) (SEQ. ID NO:624)
5'-GAT GGA GGG CGG CAT GGC-3' (Fragment 618) (SEQ. ID NO:625)
5'-GAT GGA GGG CGG CAT GG-3' (Fragment 619) (SEQ. ID NO:626)
5'-GAT GGA GGG CGG CAT G-3' (Fragment 620) (SEQ. ID NO:627)
5'-GAT GGA GGG CGG CAT-3' (Fragment 621) (SEQ. ID NO:628)
5'-GAT GGA GGG CGG CA-3' (Fragment 622) (SEQ. ID NO:629)
5'-GAT GGA GGG CGG C-3' (Fragment 623) (SEQ. ID NO:630)
5'-GAT GGA GGG CGG-3' (Fragment 624) (SEQ. ID NO:631)
5'-GAT GGA GGG CG-3' (Fragment 625) (SEQ. ID NO:632)
5'-GAT GGA GGG C-3' (Fragment 626) (SEQ. ID NO:633)
5'-AT GGA GGG CGG CAT GGC GGG CAC AGG CTG GGC-3' (Fragment 627) (SEQ. ID NO:634)
5'-AT GGA GGG CGG CAT GGC GGG CAC AGG CTG GG-3' (Fragment 628) (SEQ. ID NO:635)
5'-AT GGA GGG CGG CAT GGC GGG CAC AGG CTG G-3' (Fragment 629) (SEQ. ID NO:636)
5'-AT GGA GGG CGG CAT GGC GGG CAC AGG CTG-3' (Fragment 630) (SEQ. ID NO:637)
5'-AT GGA GGG CGG CAT GGC GGG CAC AGG CT-3' (Fragment 631) (SEQ. ID NO:638)
5'-AT GGA GGG CGG CAT GGC GGG CAC AGG C-3' (Fragment 632) (SEQ. ID NO:639)
5'-AT GGA GGG CGG CAT GGC GGG CAC AGG-3' (Fragment 633) (SEQ. ID NO:640)
5'-AT GGA GGG CGG CAT GGC GGG CAC AG-3' (Fragment 634) (SEQ. ID NO:641)
5'-AT GGA GGG CGG CAT GGC GGG CAC A-3' (Fragment 635) (SEQ. ID NO:642)
5'-AT GGA GGG CGG CAT GGC GGG CAC-3' (Fragment 636) (SEQ. ID NO:643)
5'-AT GGA GGG CGG CAT GGC GGG CA-3' (Fragment 637) (SEQ. ID NO:644)
5'-AT GGA GGG CGG CAT GGC GGG C-3' (Fragment 638) (SEQ. ID NO:645)
5'-AT GGA GGG CGG CAT GGC GGG-3' (Fragment 639) (SEQ. ID NO:646)
5'-AT GGA GGG CGG CAT GGC GG-3' (Fragment 640) (SEQ. ID NO:647)
5'-AT GGA GGG CGG CAT GGC G-3' (Fragment 641) (SEQ. ID NO:648)
5'-AT GGA GGG CGG CAT GGC-3' (Fragment 642) (SEQ. ID NO:649)

5'-AT GGA GGG CGG CAT GG-3' (Fragment 643) (SEQ. ID NO:650)
5'-AT GGA GGG CGG CAT G-3' (Fragment 644) (SEQ. ID NO:651)
5'-AT GGA GGG CGG CAT-3' (Fragment 645) (SEQ. ID NO:652)
5'-AT GGA GGG CGG CA-3' (Fragment 646) (SEQ. ID NO:653)
5'-AT GGA GGG CGG C-3' (Fragment 647) (SEQ. ID NO:654)
5'-AT GGA GGG CGG-3' (Fragment 648) (SEQ. ID NO:655)
5'-AT GGA GGG CG-3' (Fragment 649) (SEQ. ID NO:656)
5'-TGGA GGG CGG CAT GGC GGG CAC AGG CTG GGC-3' (Fragment 650) (SEQ. ID NO:657)
5'-TGGA GGG CGG CAT GGC GGG CAC AGG CTG GG-3' (Fragment 651) (SEQ. ID NO:658)
5'-TGGA GGG CGG CAT GGC GGG CAC AGG CTG G-3' (Fragment 652) (SEQ. ID NO:659)
5'-TGGA GGG CGG CAT GGC GGG CAC AGG CTG-3' (Fragment 653) (SEQ. ID NO:660)
5'-TGGA GGG CGG CAT GGC GGG CAC AGG CT-3' (Fragment 654) (SEQ. ID NO:661)
5'-TGGA GGG CGG CAT GGC GGG CAC AGG C-3' (Fragment 655) (SEQ. ID NO:662)
5'-TGGA GGG CGG CAT GGC GGG CAC AGG-3' (Fragment 656) (SEQ. ID NO:663)
5'-TGGA GGG CGG CAT GGC GGG CAC AG-3' (Fragment 657) (SEQ. ID NO:664)
5'-TGGA GGG CGG CAT GGC GGG CAC A-3' (Fragment 658) (SEQ. ID NO:665)
5'-TGGA GGG CGG CAT GGC GGG CAC-3' (Fragment 659) (SEQ. ID NO:666)
5'-TGGA GGG CGG CAT GGC GGG CA-3' (Fragment 660) (SEQ. ID NO:667)
5'-TGGA GGG CGG CAT GGC GGG C-3' (Fragment 661) (SEQ. ID NO:668)
5'-TGGA GGG CGG CAT GGC GGG-3' (Fragment 662) (SEQ. ID NO:669)
5'-TGGA GGG CGG CAT GGC GG-3' (Fragment 663) (SEQ. ID NO:670)
5'-TGGA GGG CGG CAT GGC G-3' (Fragment 664) (SEQ. ID NO:671)
5'-TGGA GGG CGG CAT GGC-3' (Fragment 665) (SEQ. ID NO:672)
5'-TGGA GGG CGG CAT GG-3' (Fragment 666) (SEQ. ID NO:673)
5'-TGGA GGG CGG CAT G-3' (Fragment 667) (SEQ. ID NO:674)
5'-TGGA GGG CGG CAT-3' (Fragment 668) (SEQ. ID NO:675)
5'-TGGA GGG CGG CA-3' (Fragment 669) (SEQ. ID NO:676)
5'-TGGA GGG CGG C-3' (Fragment 670) (SEQ. ID NO:677)
5'-TGGA GGG CGG-3' (Fragment 671) (SEQ. ID NO:678)
5'-GGA GGG CGG CAT GGC GGG CAC AGG CTG GGC-3' (Fragment 672) (SEQ. ID NO:679)
5'-GGA GGG CGG CAT GGC GGG CAC AGG CTG GG-3' (Fragment 673) (SEQ. ID NO:680)
5'-GGA GGG CGG CAT GGC GGG CAC AGG CTG G-3' (Fragment 674) (SEQ. ID NO:681)
5'-GGA GGG CGG CAT GGC GGG CAC AGG CTG-3' (Fragment 675) (SEQ. ID NO:682)
5'-GGA GGG CGG CAT GGC GGG CAC AGG CT-3' (Fragment 676) (SEQ. ID NO:683)
5'-GGA GGG CGG CAT GGC GGG CAC AGG C-3' (Fragment 677) (SEQ. ID NO:684)
5'-GGA GGG CGG CAT GGC GGG CAC AGG-3' (Fragment 678) (SEQ. ID NO:685)
5'-GGA GGG CGG CAT GGC GGG CAC AG-3' (Fragment 679) (SEQ. ID NO:686)
5'-GGA GGG CGG CAT GGC GGG CAC A-3' (Fragment 680) (SEQ. ID NO:687)
5'-GGA GGG CGG CAT GGC GGG CAC-3' (Fragment 681) (SEQ. ID NO:688)
5'-GGA GGG CGG CAT GGC GGG CA-3' (Fragment 682) (SEQ. ID NO:689)
5'-GGA GGG CGG CAT GGC GGG C-3' (Fragment 683) (SEQ. ID NO:690)
5'-GGA GGG CGG CAT GGC GGG-3' (Fragment 684) (SEQ. ID NO:691)
5'-GGA GGG CGG CAT GGC GG-3' (Fragment 685) (SEQ. ID NO:692)
5'-GGA GGG CGG CAT GGC G-3' (Fragment 686) (SEQ. ID NO:693)
5'-GGA GGG CGG CAT GGC-3' (Fragment 687) (SEQ. ID NO:694)
5'-GGA GGG CGG CAT GG-3' (Fragment 688) (SEQ. ID NO:695)
5'-GGA GGG CGG CAT G-3' (Fragment 689) (SEQ. ID NO:696)
5'-GGA GGG CGG CAT-3' (Fragment 690) (SEQ. ID NO:697)
5'-GGA GGG CGG CA-3' (Fragment 691) (SEQ. ID NO:698)
5'-GGA GGG CGG C-3' (Fragment 692) (SEQ. ID NO:699)
5'-GA GGG CGG CAT GGC GGG CAC AGG CTG GGC-3' (Fragment 693) (SEQ. ID NO:700)
5'-GA GGG CGG CAT GGC GGG CAC AGG CTG GG-3' (Fragment 694) (SEQ. ID NO:701)
5'-GA GGG CGG CAT GGC GGG CAC AGG CTG G-3' (Fragment 695) (SEQ. ID NO:702)
5'-GA GGG CGG CAT GGC GGG CAC AGG CTG-3' (Fragment 696) (SEQ. ID NO:703)
5'-GA GGG CGG CAT GGC GGG CAC AGG CT-3' (Fragment 697) (SEQ. ID NO:704)
5'-GA GGG CGG CAT GGC GGG CAC AGG C-3' (Fragment 698) (SEQ. ID NO:705)
5'-GA GGG CGG CAT GGC GGG CAC AGG-3' (Fragment 699) (SEQ. ID NO:706)
5'-GA GGG CGG CAT GGC GGG CAC AG-3' (Fragment 700) (SEQ. ID NO:707)
5'-GA GGG CGG CAT GGC GGG CAC A-3' (Fragment 701) (SEQ. ID NO:708)
5'-GA GGG CGG CAT GGC GGG CAC-3' (Fragment 702) (SEQ. ID NO:709)
5'-GA GGG CGG CAT GGC GGG CA-3' (Fragment 703) (SEQ. ID NO:710)
5'-GA GGG CGG CAT GGC GGG C-3' (Fragment 704) (SEQ. ID NO:711)
5'-GA GGG CGG CAT GGC GGG-3' (Fragment 705) (SEQ. ID NO:712)
5'-GA GGG CGG CAT GGC GG-3' (Fragment 706) (SEQ. ID NO:713)
5'-GA GGG CGG CAT GGC G-3' (Fragment 707) (SEQ. ID NO:714)
5'-GA GGG CGG CAT GGC-3' (Fragment 708) (SEQ. ID NO:715)
5'-GA GGG CGG CAT GG-3' (Fragment 709) (SEQ. ID NO:716)
5'-GA GGG CGG CAT G-3' (Fragment 710) (SEQ. ID NO:717)
5'-GA GGG CGG CAT-3' (Fragment 711) (SEQ. ID NO:718)

5'-GA GGG CGG CA-3' (Fragment 712) (SEQ. ID NO:719)
5'-A GGG CGG CAT GGC GGG CAC AGG CTG GGC-3' (Fragment 713) (SEQ. ID NO:720)
5'-A GGG CGG CAT GGC GGG CAC AGG CTG GG-3' (Fragment 714) (SEQ. ID NO:721)
5'-A GGG CGG CAT GGC GGG CAC AGG CTG G-3' (Fragment 715) (SEQ. ID NO:722)
5'-A GGG CGG CAT GGC GGG CAC AGG CTG-3' (Fragment 716) (SEQ. ID NO:723)
5'-A GGG CGG CAT GGC GGG CAC AGG CT-3' (Fragment 717) (SEQ. ID NO:724)
5'-A GGG CGG CAT GGC GGG CAC AGG C-3' (Fragment 718) (SEQ. ID NO:725)
5'-A GGG CGG CAT GGC GGG CAC AGG-3' (Fragment 719) (SEQ. ID NO:726)
5'-A GGG CGG CAT GGC GGG CAC AG-3' (Fragment 720) (SEQ. ID NO:727)
5'-A GGG CGG CAT GGC GGG CAC A-3' (Fragment 721) (SEQ. ID NO:728)
5'-A GGG CGG CAT GGC GGG CAC-3' (Fragment 722) (SEQ. ID NO:729)
5'-A GGG CGG CAT GGC GGG CA-3' (Fragment 723) (SEQ. ID NO:730)
5'-A GGG CGG CAT GGC GGG C-3' (Fragment 724) (SEQ. ID NO:731)
5'-A GGG CGG CAT GGC GGG-3' (Fragment 725) (SEQ. ID NO:732)
5'-A GGG CGG CAT GGC GG-3' (Fragment 726) (SEQ. ID NO:733)
5'-A GGG CGG CAT GGC G-3' (Fragment 727) (SEQ. ID NO:734)
5'-A GGG CGG CAT GGC-3' (Fragment 728) (SEQ. ID NO:735)
5'-A GGG CGG CAT GG-3' (Fragment 729) (SEQ. ID NO:736)
5'-A GGG CGG CAT G-3' (Fragment 730) (SEQ. ID NO:737)
5'-A GGG CGG CAT-3' (Fragment 731) (SEQ. ID NO:738)
5'-GGG CGG CAT GGC GGG CAC AGG CTG GGC-3' (Fragment 732) (SEQ. ID NO:739)
5'-GGG CGG CAT GGC GGG CAC AGG CTG GG-3' (Fragment 733) (SEQ. ID NO:740)
5'-GGG CGG CAT GGC GGG CAC AGG CTG G-3' (Fragment 734) (SEQ. ID NO:741)
5'-GGG CGG CAT GGC GGG CAC AGG CTG-3' (Fragment 735) (SEQ. ID NO:742)
5'-GGG CGG CAT GGC GGG CAC AGG CT-3' (Fragment 736) (SEQ. ID NO:743)
5'-GGG CGG CAT GGC GGG CAC AGG C-3' (Fragment 737) (SEQ. ID NO:744)
5'-GGG CGG CAT GGC GGG CAC AGG-3' (Fragment 738) (SEQ. ID NO:745)
5'-GGG CGG CAT GGC GGG CAC AG-3' (Fragment 739) (SEQ. ID NO:746)
5'-GGG CGG CAT GGC GGG CAC A-3' (Fragment 740) (SEQ. ID NO:747)
5'-GGG CGG CAT GGC GGG CAC-3' (Fragment 741) (SEQ. ID NO:748)
5'-GGG CGG CAT GGC GGG CA-3' (Fragment 742) (SEQ. ID NO:749)
5'-GGG CGG CAT GGC GGG C-3' (Fragment 743) (SEQ. ID NO:750)
5'-GGG CGG CAT GGC GGG-3' (Fragment 744) (SEQ. ID NO:751)
5'-GGG CGG CAT GGC GG-3' (Fragment 745) (SEQ. ID NO:752)
5'-GGG CGG CAT GGC G-3' (Fragment 746) (SEQ. ID NO:753)
5'-GGG CGG CAT GGC-3' (Fragment 747) (SEQ. ID NO:754)
5'-GGG CGG CAT GG-3' (Fragment 748) (SEQ. ID NO:755)
5'-GGG CGG CAT G-3' (Fragment 749) (SEQ. ID NO:756)
5'-GG CGG CAT GGC GGG CAC AGG CTG GGC-3' (Fragment 750) (SEQ. ID NO:757)
5'-GG CGG CAT GGC GGG CAC AGG CTG GG-3' (Fragment 751) (SEQ. ID NO:758)
5'-GG CGG CAT GGC GGG CAC AGG CTG G-3' (Fragment 752) (SEQ. ID NO:759)
5'-GG CGG CAT GGC GGG CAC AGG CTG-3' (Fragment 753) (SEQ. ID NO:760)
5'-GG CGG CAT GGC GGG CAC AGG CT-3' (Fragment 754) (SEQ. ID NO:761)
5'-GG CGG CAT GGC GGG CAC AGG C-3' (Fragment 755) (SEQ. ID NO:762)
5'-GG CGG CAT GGC GGG CAC AGG-3' (Fragment 756) (SEQ. ID NO:763)
5'-GG CGG CAT GGC GGG CAC AG-3' (Fragment 757) (SEQ. ID NO:764)
5'-GG CGG CAT GGC GGG CAC A-3' (Fragment 758) (SEQ. ID NO:765)
5'-GG CGG CAT GGC GGG CAC-3' (Fragment 759) (SEQ. ID NO:766)
5'-GG CGG CAT GGC GGG CA-3' (Fragment 760) (SEQ. ID NO:767)
5'-GG CGG CAT GGC GGG C-3' (Fragment 761) (SEQ. ID NO:768)
5'-GG CGG CAT GGC GGG-3' (Fragment 762) (SEQ. ID NO:769)
5'-GG CGG CAT GGC GG-3' (Fragment 763) (SEQ. ID NO:770)
5'-GG CGG CAT GGC G-3' (Fragment 764) (SEQ. ID NO:771)
5'-GG CGG CAT GGC-3' (Fragment 765) (SEQ. ID NO:772)
5'-GG CGG CAT GG-3' (Fragment 766) (SEQ. ID NO:773)
5'-G CGG CAT GGC GGG CAC AGG CTG GGC-3' (Fragment 767) (SEQ. ID NO:774)
5'-G CGG CAT GGC GGG CAC AGG CTG GG-3' (Fragment 768) (SEQ. ID NO:775)
5'-G CGG CAT GGC GGG CAC AGG CTG G-3' (Fragment 769) (SEQ. ID NO:776)
5'-G CGG CAT GGC GGG CAC AGG CTG-3' (Fragment 770) (SEQ. ID NO:777)
5'-G CGG CAT GGC GGG CAC AGG CT-3' (Fragment 771) (SEQ. ID NO:778)
5'-G CGG CAT GGC GGG CAC AGG C-3' (Fragment 772) (SEQ. ID NO:779)
5'-G CGG CAT GGC GGG CAC AGG-3' (Fragment 773) (SEQ. ID NO:780)
5'-G CGG CAT GGC GGG CAC AG-3' (Fragment 774) (SEQ. ID NO:781)
5'-G CGG CAT GGC GGG CAC A-3' (Fragment 775) (SEQ. ID NO:782)
5'-G CGG CAT GGC GGG CAC-3' (Fragment 776) (SEQ. ID NO:783)
5'-G CGG CAT GGC GGG CA-3' (Fragment 777) (SEQ. ID NO:784)
5'-G CGG CAT GGC GGG C-3' (Fragment 778) (SEQ. ID NO:785)
5'-G CGG CAT GGC GGG-3' (Fragment 779) (SEQ. ID NO:786)
5'-G CGG CAT GGC GG-3' (Fragment 780) (SEQ. ID NO:787)
5'-G CGG CAT GGC G-3' (Fragment 781) (SEQ. ID NO:788)

5'-G CGG CAT GGC-3' (Fragment 782) (SEQ. ID NO:789)
5'-CGG CAT GGC GGG CAC AGG CTG GGC-3' (Fragment 783) (SEQ. ID NO:790)
5'-CGG CAT GGC GGG CAC AGG CTG GG-3' (Fragment 784) (SEQ. ID NO:791)
5'-CGG CAT GGC GGG CAC AGG CTG G-3' (Fragment 785) (SEQ. ID NO:792)
5'-CGG CAT GGC GGG CAC AGG CTG-3' (Fragment 786) (SEQ. ID NO:793)
5'-CGG CAT GGC GGG CAC AGG CT-3' (Fragment 787) (SEQ. ID NO:794)
5'-CGG CAT GGC GGG CAC AGG C-3' (Fragment 788) (SEQ. ID NO:795)
5'-CGG CAT GGC GGG CAC AGG-3' (Fragment 789) (SEQ. ID NO:796)
5'-CGG CAT GGC GGG CAC AG-3' (Fragment 790) (SEQ. ID NO:797)
5'-CGG CAT GGC GGG CAC A-3' (Fragment 791) (SEQ. ID NO:798)
5'-CGG CAT GGC GGG CAC-3' (Fragment 792) (SEQ. ID NO:799)
5'-CGG CAT GGC GGG CA-3' (Fragment 793) (SEQ. ID NO:800)
5'-CGG CAT GGC GGG C-3' (Fragment 794) (SEQ. ID NO:801)
5'-CGG CAT GGC GGG-3' (Fragment 795) (SEQ. ID NO:802)
5'-CGG CAT GGC GG-3' (Fragment 796) (SEQ. ID NO:803)
5'-CGG CAT GGC G-3' (Fragment 797) (SEQ. ID NO:804)
5'-GG CAT GGC GGG CAC AGG CTG GGC-3' (Fragment 798) (SEQ. ID NO:805)
5'-GG CAT GGC GGG CAC AGG CTG GG-3' (Fragment 799) (SEQ. ID NO:806)
5'-GG CAT GGC GGG CAC AGG CTG G-3' (Fragment 800) (SEQ. ID NO:807)
5'-GG CAT GGC GGG CAC AGG CTG-3' (Fragment 801) (SEQ. ID NO:808)
5'-GG CAT GGC GGG CAC AGG CT-3' (Fragment 802) (SEQ. ID NO:809)
5'-GG CAT GGC GGG CAC AGG C-3' (Fragment 803) (SEQ. ID NO:810)
5'-GG CAT GGC GGG CAC AGG-3' (Fragment 804) (SEQ. ID NO:811)
5'-GG CAT GGC GGG CAC AG-3' (Fragment 805) (SEQ. ID NO:812)
5'-GG CAT GGC GGG CAC A-3' (Fragment 806) (SEQ. ID NO:813)
5'-GG CAT GGC GGG CAC-3' (Fragment 807) (SEQ. ID NO:814)
5'-GG CAT GGC GGG CA-3' (Fragment 808) (SEQ. ID NO:815)
5'-GG CAT GGC GGG C-3' (Fragment 809) (SEQ. ID NO:816)
5'-GG CAT GGC GGG-3' (Fragment 810) (SEQ. ID NO:817)
5'-GG CAT GGC GG-3' (Fragment 811) (SEQ. ID NO:818)
5'-G CAT GGC GGG CAC AGG CTG GGC-3' (Fragment 812) (SEQ. ID NO:819)
5'-G CAT GGC GGG CAC AGG CTG GG-3' (Fragment 813) (SEQ. ID NO:820)
5'-G CAT GGC GGG CAC AGG CTG G-3' (Fragment 814) (SEQ. ID NO:821)
5'-G CAT GGC GGG CAC AGG CTG-3' (Fragment 815) (SEQ. ID NO:822)
5'-G CAT GGC GGG CAC AGG CT-3' (Fragment 816) (SEQ. ID NO:823)
5'-G CAT GGC GGG CAC AGG C-3' (Fragment 817) (SEQ. ID NO:824)
5'-G CAT GGC GGG CAC AGG-3' (Fragment 818) (SEQ. ID NO:825)
5'-G CAT GGC GGG CAC AG-3' (Fragment 819) (SEQ. ID NO:826)
5'-G CAT GGC GGG CAC A-3' (Fragment 820) (SEQ. ID NO:827)
5'-G CAT GGC GGG CAC-3' (Fragment 821) (SEQ. ID NO:828)
5'-G CAT GGC GGG CA-3' (Fragment 822) (SEQ. ID NO:829)
5'-G CAT GGC GGG C-3' (Fragment 823) (SEQ. ID NO:830)
5'-G CAT GGC GGG-3' (Fragment 824) (SEQ. ID NO:831)
5'-CAT GGC GGG CAC AGG CTG GGC-3' (Fragment 825) (SEQ. ID NO:832)
5'-CAT GGC GGG CAC AGG CTG GG-3' (Fragment 826) (SEQ. ID NO:833)
5'-CAT GGC GGG CAC AGG CTG G-3' (Fragment 827) (SEQ. ID NO:834)
5'-CAT GGC GGG CAC AGG CTG-3' (Fragment 828) (SEQ. ID NO:835)
5'-CAT GGC GGG CAC AGG CT-3' (Fragment 829) (SEQ. ID NO:836)
5'-CAT GGC GGG CAC AGG C-3' (Fragment 830) (SEQ. ID NO:837)
5'-CAT GGC GGG CAC AGG-3' (Fragment 831) (SEQ. ID NO:838)
5'-CAT GGC GGG CAC AG-3' (Fragment 832) (SEQ. ID NO:839)
5'-CAT GGC GGG CAC A-3' (Fragment 833) (SEQ. ID NO:840)
5'-CAT GGC GGG CAC-3' (Fragment 834) (SEQ. ID NO:841)
5'-CAT GGC GGG CA-3' (Fragment 835) (SEQ. ID NO:842)
5'-CAT GGC GGG C-3' (Fragment 836) (SEQ. ID NO:843)
5'-AT GGC GGG CAC AGG CTG GGC-3' (Fragment 837) (SEQ. ID NO:844)
5'-AT GGC GGG CAC AGG CTG GG-3' (Fragment 838) (SEQ. ID NO:845)
5'-AT GGC GGG CAC AGG CTG G-3' (Fragment 839) (SEQ. ID NO:846)
5'-AT GGC GGG CAC AGG CTG-3' (Fragment 840) (SEQ. ID NO:847)
5'-AT GGC GGG CAC AGG CT-3' (Fragment 841) (SEQ. ID NO:848)
5'-AT GGC GGG CAC AGG C-3' (Fragment 842) (SEQ. ID NO:849)
5'-AT GGC GGG CAC AGG-3' (Fragment 843) (SEQ. ID NO:850)
5'-AT GGC GGG CAC AG-3' (Fragment 844) (SEQ. ID NO:851)
5'-AT GGC GGG CAC A-3' (Fragment 845) (SEQ. ID NO:852)
5'-AT GGC GGG CAC-3' (Fragment 846) (SEQ. ID NO:853)
5'-AT GGC GGG CA-3' (Fragment 847) (SEQ. ID NO:854)
5'-T GGC GGG CAC AGG CTG GGC-3' (Fragment 848) (SEQ. ID NO:855)
5'-T GGC GGG CAC AGG CTG GG-3' (Fragment 849) (SEQ. ID NO:856)
5'-T GGC GGG CAC AGG CTG G-3' (Fragment 850) (SEQ. ID NO:857)
5'-T GGC GGG CAC AGG CTG-3' (Fragment 851) (SEQ. ID NO:858)

5'-T GGC GGG CAC AGG CT-3' (Fragment 852) (SEQ. ID NO:859)
5'-T GGC GGG CAC AGG C-3' (Fragment 853) (SEQ. ID NO:860)
5'-T GGC GGG CAC AGG-3' (Fragment 854) (SEQ. ID NO:861)
5'-T GGC GGG CAC AG-3' (Fragment 855) (SEQ. ID NO:862)
5'-T GGC GGG CAC A-3' (Fragment 856) (SEQ. ID NO:863)
5'-T GGC GGG CAC-3' (Fragment 857) (SEQ. ID NO:864)
5'-GGC GGG CAC AGG CTG GGC-3' (Fragment 858) (SEQ. ID NO:865)
5'-GGC GGG CAC AGG CTG GG-3' (Fragment 859) (SEQ. ID NO:866)
5'-GGC GGG CAC AGG CTG G-3' (Fragment 860) (SEQ. ID NO:867)
5'-GGC GGG CAC AGG CTG-3' (Fragment 861) (SEQ. ID NO:868)
5'-GGC GGG CAC AGG CT-3' (Fragment 862) (SEQ. ID NO:869)
5'-GGC GGG CAC AGG C-3' (Fragment 863) (SEQ. ID NO:870)
5'-GGC GGG CAC AGG-3' (Fragment 864) (SEQ. ID NO:871)
5'-GGC GGG CAC AG-3' (Fragment 865) (SEQ. ID NO:872)
5'-GGC GGG CAC A-3' (Fragment 866) (SEQ. ID NO:873)
5'-GC GGG CAC AGG CTG GGC-3' (Fragment 867) (SEQ. ID NO:874)
5'-GC GGG CAC AGG CTG GG-3' (Fragment 868) (SEQ. ID NO:875)
5'-GC GGG CAC AGG CTG G-3' (Fragment 869) (SEQ. ID NO:876)
5'-GC GGG CAC AGG CTG-3' (Fragment 870) (SEQ. ID NO:877)
5'-GC GGG CAC AGG CT-3' (Fragment 871) (SEQ. ID NO:878)
5'-GC GGG CAC AGG C-3' (Fragment 872) (SEQ. ID NO:879)
5'-GC GGG CAC AGG-3' (Fragment 873) (SEQ. ID NO:880)
5'-GC GGG CAC AG-3' (Fragment 874) (SEQ. ID NO:881)
5'-C GGG CAC AGG CTG GGC-3' (Fragment 875) (SEQ. ID NO:882)
5'-C GGG CAC AGG CTG GG-3' (Fragment 876) (SEQ. ID NO:883)
5'-C GGG CAC AGG CTG G-3' (Fragment 877) (SEQ. ID NO:884)
5'-C GGG CAC AGG CTG-3' (Fragment 878) (SEQ. ID NO:885)
5'-C GGG CAC AGG CT-3' (Fragment 879) (SEQ. ID NO:886)
5'-C GGG CAC AGG C-3' (Fragment 880) (SEQ. ID NO:887)
5'-C GGG CAC AGG-3' (Fragment 881) (SEQ. ID NO:888)
5'-GGG CAC AGG CTG GGC-3' (Fragment 882) (SEQ. ID NO:889)
5'-GGG CAC AGG CTG GG-3' (Fragment 883) (SEQ. ID NO:890)
5'-GGG CAC AGG CTG G-3' (Fragment 884) (SEQ. ID NO:891)
5'-GGG CAC AGG CTG-3' (Fragment 885) (SEQ. ID NO:892)
5'-GGG CAC AGG CT-3' (Fragment 886) (SEQ. ID NO:893)
5'-GGG CAC AGG C-3' (Fragment 887) (SEQ. ID NO:894)
5'-GG CAC AGG CTG GGC-3' (Fragment 888) (SEQ. ID NO:895)
5'-GG CAC AGG CTG GG-3' (Fragment 889) (SEQ. ID NO:896)
5'-GG CAC AGG CTG G-3' (Fragment 890) (SEQ. ID NO:897)
5'-GG CAC AGG CTG-3' (Fragment 891) (SEQ. ID NO:898)
5'-GG CAC AGG CT-3' (Fragment 892) (SEQ. ID NO:899)
5'-G CAC AGG CTG GGC-3' (Fragment 893) (SEQ. ID NO:900)
5'-G CAC AGG CTG GG-3' (Fragment 894) (SEQ. ID NO:901)
5'-G CAC AGG CTG G-3' (Fragment 895) (SEQ. ID NO:902)
5'-G CAC AGG CTG-3' (Fragment 896) (SEQ. ID NO:903)
5'-CAC AGG CTG GGC-3' (Fragment 897) (SEQ. ID NO:904)
5'-CAC AGG CTG GG-3' (Fragment 898) (SEQ. ID NO:905)
5'-CAC AGG CTG G-3' (Fragment 899) (SEQ. ID NO:906)
5'-AC AGG CTG GGC-3' (Fragment 900) (SEQ. ID NO:907)
5'-AC AGG CTG GG-3' (Fragment 901) (SEQ. ID NO:908)
5'-C AGG CTG GGC-3' (Fragment 902) (SEQ. ID NO:909)
5'-GGC GGC CTG GAA AGC TGA GAT GGA GGG CGG CAT GGC GGG CAC AGG CTG GGC-3' (Fragment 903) (SEQ. ID NO:910)
5'-GC GGC CTG GAA AGC TGA GAT GGA GGG CGG CAT GGC GGG CAC AGG CTG GGC-3' (Fragment 904) (SEQ. ID NO:911)
5'-C GGC CTG GAA AGC TGA GAT GGA GGG CGG CAT GGC GGG CAC AGG CTG GGC-3' (Fragment 905) (SEQ. ID NO:912)
5'-GGC CTG GAA AGC TGA GAT GGA GGG CGG CAT GGC GGG CAC AGG CTG GGC-3' (Fragment 906) (SEQ. ID NO:913)
5'-GC CTG GAA AGC TGA GAT GGA GGG CGG CAT GGC GGG CAC AGG CTG GGC-3' (Fragment 907) (SEQ. ID NO:914)
5'-C CTG GAA AGC TGA GAT GGA GGG CGG CAT GGC GGG CAC AGG CTG GGC-3' (Fragment 908) (SEQ. ID NO:915)
5'-CTG GAA AGC TGA GAT GGA GGG CGG CAT GGC GGG CAC AGG CTG GGC-3' (Fragment 909) (SEQ. ID NO:916)
5'-TG GAA AGC TGA GAT GGA GGG CGG CAT GGC GGG CAC AGG CTG GGC-3' (Fragment 910) (SEQ. ID NO:917)
5'-G GAA AGC TGA GAT GGA GGG CGG CAT GGC GGG CAC AGG CTG GGC-3' (Fragment 911) (SEQ. ID NO:918)
5'-GAA AGC TGA GAT GGA GGG CGG CAT GGC GGG CAC AGG CTG GGC-3' (Fragment 912) (SEQ. ID NO:919)
5'-AA AGC TGA GAT GGA GGG CGG CAT GGC GGG CAC AGG CTG GGC-3' (Fragment 913) (SEQ. ID NO:920)
5'-A AGC TGA GAT GGA GGG CGG CAT GGC GGG CAC AGG CTG GGC-3' (Fragment 914) (SEQ. ID NO:921)
5'-AGC TGA GAT GGA GGG CGG CAT GGC GGG CAC AGG CTG GGC-3' (Fragment 915) (SEQ. ID NO:922)
5'-GC TGA GAT GGA GGG CGG CAT GGC GGG CAC AGG CTG GGC-3' (Fragment 916) (SEQ. ID NO:923)
5'-C TGA GAT GGA GGG CGG CAT GGC GGG CAC AGG CTG GGC-3' (Fragment 917) (SEQ. ID NO:924)

5'-TGA GAT GGA GGG CGG CAT GGC GGG CAC AGG CTG GGC-3' (Fragment 918) (SEQ. ID NO:925)
5'-GA GAT GGA GGG CGG CAT GGC GGG CAC AGG CTG GGC-3' (Fragment 919) (SEQ. ID NO:926)
5'-GAT GGA GGG CGG CAT GGC GGG CAC AGG CTG GGC-3' (Fragment 920) (SEQ. ID NO:927)
5'-GAT GGA GGG CGG CAT GGC GGG CAC AGG CTG GGC-3' (Fragment 921) (SEQ. ID NO:928)
5'-AT GGA GGG CGG CAT GGC CGG CAC AGG CTG GGC-3' (Fragment 922) (SEQ. ID NO:929)
5'-T GGA GGG CGG CAT GGC GGG CAC AGG CTG GGC-3' (Fragment 923) (SEQ. ID NO:930)
5'-GGA GGG CGG CAT GGC GGG CAC AGG CTG GGC-3' (Fragment 924) (SEQ. ID NO:931)
5'-GA GGG CGG CAT GGC GGG CAC AGG CTG GGC-3' (Fragment 925) (SEQ. ID NO:932)
5'-A GGG CGG CAT GGC GGG CAC AGG CTG GGC-3' (Fragment 926) (SEQ. ID NO:933)
5'-GGG CGG CAT GGC GGG CAC AGG CTG GGC-3' (Fragment 927) (SEQ. ID NO:934)
5'-GG CGG CAT GGC GGG CAC AGG CTG GGC-3' (Fragment 928) (SEQ. ID NO:935)
5'-G CGG CAT GGC GGG CAC AGG CTG GGC-3' (Fragment 929) (SEQ. ID NO:936)
5'-CGG CAT GGC GGG CAC AGG CTG GGC-3' (Fragment 930) (SEQ. ID NO:937)
5'-GG CAT GGC GGG CAC AGG CTG GGC-3' (Fragment 931) (SEQ. ID NO:938)
5'-G CAT GGC GGG CAC AGG CTG GGC-3' (Fragment 932) (SEQ. ID NO:939)
5'-CAT GGC GGG CAC AGG CTG GGC-3' (Fragment 933) (SEQ. ID NO:940)
5'-AT GGC GGG CAC AGG CTG GGC-3' (Fragment 934) (SEQ. ID NO:941)
5'-T GGC GGG CAC AGG CTG GGC-3' (Fragment 935) (SEQ. ID NO:942)
5'-GGC GGG CAC AGG CTG GGC-3' (Fragment 936) (SEQ. ID NO:943)
5'-GC GGG CAC AGG CTG GGC-3' (Fragment 937) (SEQ. ID NO:944)
5'-C GGG CAC AGG CTG GGC-3' (Fragment 938) (SEQ. ID NO:945)
5'-GGG CAC AGG CTG GGC-3' (Fragment 939) (SEQ. ID NO:946)
5'-GG CAC AGG CTG GGC-3' (Fragment 940) (SEQ. ID NO:947)
5'-G CAC AGG CTG GGC-3' (Fragment 941) (SEQ. ID NO:948)
5'-CAC AGG CTG GGC-3' (Fragment 942) (SEQ. ID NO:949)
5'-AC AGG CTG GGC-3' (Fragment 943) (SEQ. ID NO:950)
5'-C AGG CTG GGC-3' (Fragment 944) (SEQ. ID NO:951)
5'-AGG CTG GGC-3' (Fragment 945) (SEQ. ID NO:952)

Other adenosine fragments, for example those with low adenosine content or lacking adenosine altogether, are also suitable and in some cases even preferred, for use with the invention. The following sequences, their fragments and combinations, are one particularly preferred group of anti-sense oligos.

TTT TCC TTC CTT TGT CTC TCT TC (FRAG 946) (SEQ ID NO: 953)
GCT CCC GGC TGC CTG (FRAG 947) (SEQ. ID NO: 954)
CTC GGC CGT GCG GCT CTG TCG CTC CCG GT (FRAG 948) (SEQ. ID NO: 955)
CCG CCG CCC TCC GGG GGG TC (FRAG 949) (SEQ. ID NO: 956)
TGC TGC CGT TGG CTG CCC (FRAG 950) (SEQ. ID NO: 957)
CTT CTG CGG GTC GCC GG (FRAG 951) (SEQ. ID NO: 958)
TGC TGG GCT TGT GGC (FRAG 952) (SEQ. ID NO: 959)
GGC CTC TCT TCT GGG (FRAG 953) (SEQ. ID NO: 960)
CCT GGT CCC TCC GT (FRAG 954) (SEQ. ID NO: 961)
GGT GGC TCC TCT GC (FRAG 955) (SEQ. ID NO: 962)
GCT TGG TCC TGG GGC TGC (FRAG 956) (SEQ. ID NO: 963)
TGC TCT CCT CTC CTT (FRAG 957) (SEQ. ID NO: 964)

In another embodiment of this invention, the oligos are anti-sense to an adenosine $A_{2a}$ receptor, and must either be "up-regulated", or if they have some adenosine $A_1$ activity they are treated as the other anti-sense oligos. The following sequences are preferred examples of anti-sense oligos associated with the human adenosine $A_{2a}$ receptor. Another preferred group is composed of fragments of these sequences and combinations thereof as well as mixtures. Also preferred are these sequences, fragments and their combinations where one or more adenosines are substituted by a universal base or an adenosine analogue which either is not an agonist or a ligand for the adenosine $A_1$ receptor, or which acts as an antagonist of the $A_1$ receptor, such as, for example, theophylline or enprophylline.

5'-TGC TTT TCT TTT CTG GGC CTC-3' (FRAG 958) (SEQ. ID NO: 965)
5'-TGT GGT CTG TTT TTT TCT G-3' (FRAG 959) (SEQ. ID NO: 966)
5'-GCC CTG CTG GGG CGC TCT CC-3' (FRAG 960) (SEQ. ID NO: 967)
5'-GCC GCC CGC CTG GCT CCC-3' (FRAG 961) (SEQ. ID NO: 968)
5'-GGB GCC CBT GBT GGG CBT GCC-3' (FRAG 962) (SEQ. ID NO: 969)
5'-GTG GTT CTT GCC CTC CTT TGG CTG-3' (FRAG 963) (SEQ. ID NO: 970)
5'-CCG TGC CCG CTC CCC GGC-3' (FRAG 964) (SEQ. ID NO: 971)
5'-CTC CTG GCG GGT GGC CGT TG-3' (FRAG 965) (SEQ. ID NO: 972)
5'-GGC CCG TGT TCC CCT GGG-3' (FRAG 966) (SEQ. ID NO: 973)
5'-GCC TGG GGC TCC CTT CTC TC-3' (FRAG 967) (SEQ. ID NO: 974)
5'-GCC CTT CTT GCT GGG CCT C-3' (FRAG 968) (SEQ. ID NO: 975)
5'-TGC TGC TGC TGG TGC TGT GGC CCC C-3' (FRAG 969) (SEQ. ID NO: 976)
GTACACCGAGGAGCCCATGATGGGCAT-GCCACAGACGACAGGC (FRAG 970) (SEQ. ID NO: 977)
GTBCBCCGBGGBGCCCBTGBTGGGCBT-GCCBCBGBCGBCBGGC (FRAG 971) (SEQ. ID NO: 978)

In another embodiment, the anti-sense oligo of the invention may be a sequence which is anti-sense to the adenosine $A_{2b}$ receptor. By means of example, the following sequences associated with the human receptor are provided. These sequences as well as their fragments and combinations, desadenosine fragments and those where one or more A are substituted with a universal base or adenosine analogue as described above are preferred.

5'-GGC GCC GTG CCG CGT CTT GGT GGC GGC GG-3' (FRAG 972) (SEQ. ID NO: 979)
5'-GTT CGC GCC CGC GCG GGG CCC CTC CGG TCC-3' (FRAG 973) (SEQ. ID NO: 980)

5'-TTG GCC CGC GCG CCC GCC CGT CTC GGG CTG GGC GG-3 (FRAG 974) (SEQ. ID NO: 981)
5'-CGG GTC GGG GCC CCC CGC GGC C-3' (FRAG 975) (SEQ. ID NO: 982)
5'-GCC TCG GGG CTG GGG CGC TGG TGG CCG GG-3' (FRAG 976) (SEQ. ID NO: 983)
5'-CCG CGC CTC CGC CTG CCG CTT CTG-3' (FRAG 977) (SEQ. ID NO: 984)
5'-GCT GGG CCC CGG GCG CCC CCT-3' (FRAG 978) (SEQ. ID NO: 985)
5'-CCC CTC TTG CTC GGG TCC CCG TG-3' (FRAG 979) (SEQ. ID NO: 986)
ACAGCGCGTCCTGTGTCTCCAGCAG-CATGGCCGGGCCAGCTGGGCCCC (FRAG 980) (SEQ. ID NO: 987)
BCBGCGCGTCCTGTGTCTCCBGCB-GCBTGGCCGGGCCBGCTGGGCCCC (FRAG 981) (SEQ. ID NO: 988)

In still another embodiment, the oligo of this invention may be anti-sense to any fragment of the adenosine $A_3$ receptor gene or mRNA, including overlapping regions with the flanking regions or introns. The following are examples of these fragments associated with the human receptor. These are preferred sequences. Also preferred are their fragments and combinations, as well as desadenosine fragments and those where one or more A are substituted by a universal base or A analogue as described above.

ACA GAG CA TGC TGT TGT TGG GCA TCT TGC CTT CCC AGG G (FRAG 982) (SEQ. ID NO: 989)
BCB GBG CB TGC TGT TGT TGG GCB TCT TGC CTT CCC BGG G (FRAG 983) (SEQ. ID NO: 990)
CCC TTT TCT GGT GGG GTG (FRAG 984) (SEQ. ID NO: 991)
GTG CTG TTG TTG GGC (FRAG 985) (SEQ. ID NO: 992)
TTT CTT CTG TTC CC (FRAG 986) (SEQ. ID NO: 993)
CCC TTT TCT GGT GGG GTG (FRAG 987) (SEQ. ID NO: 994)
GTG CTG TTG TTG GGC (FRAG 988) (SEQ. ID NO: 995)
TTT CTT CTG TTC CC (FRAG 989) (SEQ. ID NO: 996)

In the anti-sense oligonucleotides of the present invention, exemplified by the preceding sequences, a number of adenosine bases may be replaced with an appropriate "spacer" or universal base (e.g., 1-[β-D-2'-deoxyribofuranosyl]-5-nitroindole, or with an adenosine agonist or antagonist that does not stimulate adenosine $A_1$, $A_{2b}$ or $A_3$ receptors, but which may stimulate adenosine $A_{2a}$ receptors. In this manner, a specific adenosine receptor gene may be targeted to obtain one or more anti-sense oligonucleotide(s) (oligos) that selectively bind(s) to the corresponding mRNA, and then, if necessary, their content of adenosine may be reduced by substituting one or more universal bases or adenosine analogues incapable of activating adenosine $A_1$, $A_{2b}$ or $A_3$ receptors or which activate the adenosine $A_{2a}$ receptor. Thus, in addition to "down-regulating" specific adenosine receptor genes, the present oligos have an increased effect when administered by either selection of genes, RNA and flanking regions that are devoid, or have a low A content, or alternatively one or more of the adenosine(s) present in the oligonucleotide(s) are substituted with other nucleotide bases, so called universal bases, which bind to thymidine (T) but lack the ability to activate adenosine receptors and otherwise may not activate adenosine receptors. Given that adenosine (A) is a nucleotide base complementary to thymidine (T), when a T appears in the RNA, the anti-sense oligo will have an A at the same position.

The method of the present invention may be used to treat ailments associated with or causing bronchoconstriction allegy(ies) and/or inflammation association with a ny of the diseases and conditions described above in a subject, regardless of its cause. The anti-sense agent(s) of the invention have preferably a low (or reduced) A content to prevent its liberation upon in vivo degradation of the agent(s), preferably up to about 15%, more preferably up to about 10%, still more preferably up to about 5%, and even more preferred being devoid of A ("desadenosine oligos").

The oligos of this invention may be obtained by first selecting fragments of a target nucleic acid having at least 4 contiguous nucleic acids selected from the group consisting of G and C, and then obtaining a first oligonucleotide 4 to 60 nucleotide long which comprises the selected fragment and has a C and G nucleic acid content of up to and including about 15%. The latter step may be conducted by obtaining a second oligonucleotide 4 to 60 nucleotide long comprising a sequence which is anti-sense to the selected fragment, the second oligonucleotide having an adenosine base content of up to and including about 15%. This method may also comprise, when the selected fragment comprises at least one thymidine base, substituting an adenosine base in the corresponding nucleotide of the anti-sense fragment with a universal base selected from the group consisting of heteroaromatic bases which bind to a thymidine base but have antagonist activity and less than about 0.3 of the adenosine base agonist activity at the adenosine $A_1$, $A_{2b}$ and $A_3$ receptors, and heteroaromatic bases which have no activity or have an agonist activity at the adenosine $A_{2a}$ receptor. The analogue heteroaromatic bases may be selected from all pyrimidines and purines, which may be substituted by O, halo, $NH_2$, SH, SO, $SO_2$, $SO_3$, COOH and branched and fused primary and secondary amino, alkyl, alkenyl, alkynyl, cycloalkyl, heterocycloalkyl, aryl, heteroaryl, alkoxy, alkenoxy, acyl, cycloacyl, arylacyl, alkynoxy, cycloalkoxy, aroyl, arylthio, arylsulfoxyl, halocycloalkyl, alkylcycloalkyl, alkenylcycloalkyl, alkynylcycloalkyl, haloaryl, alkylaryl, alkenylaryl, alkynylaryl, arylalkyl, arylalkenyl, arylalkynyl, arylcycloalkyl, which may be further substituted by O, halo, $NH_2$, primary, secondary and tertiary amine, SH, SO, $SO_2$, $SO_3$, cycloalkyl, heterocycloalkyl and heteroaryl. The pyrimidines and purines may be substituted at all positions as is known in the art, but preferred are those which are substituted at positions 1, 2, 3, 4, 7 and/or 8. More preferred are pyrimidines and purines such as theophylline, caffeine, dyphylline, etophylline, acephylline piperazine, bamifylline, emprofylline and xantine having the chemical formula

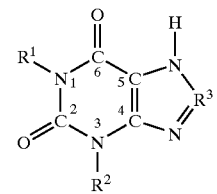

wherein $R^1$ and $R^2$ are independently H, alkyl, alkenyl or alkynyl and $R^3$ is H, aryl, dicycloalkyl, dicycloalkenyl, dicycloalkynyl, cycloalkyl, cycloalkenyl, cycloalkynyl, O-cycloalkyl, O-cycloalkenyl, O-cycloalkynyl, $NH_2$-alkylamino ketoxyalkyloxy-aryl, mono and dialkylaminoalkyl-N-alkylamino-$SO_2$ aryl, among others. However, other methods may also be employed. The inventor reduced the adenosine content of the anti-sense oligos corresponding to the thymidines (T) present in the target gene, RNA, flanking regions, and bridging sections to less than about 15%, or fully eliminated A from the oligonucleotide sequence as a means for preventing their breakdown products from freeing adenosine into the lung tissue environment and, thereby, aggravating the subject's ailment and/or countering the beneficial effect of the administered.

Also part of this invention are chemical analogues of the nucleic acids in which, for example, the phosphodiester bonds have been modified, e.g., to a methylphosphonate, a phosphotriester, a phosphorothioate, a phosphorodithioate, or a phosphoramidate, so as to render the nucleic acids more stable in vivo. The naturally occurring phosphodiester linkages in nucleic acids are susceptible to degradation by endogenously occurring cellular nucleases, while many analogues linkages are highly resistant to nuclease degradation. See Milligan et al., and Coben, J. S., supra. The use of a "3'-end cap" strategy by which nuclease-resistant linkages are substituted for phosphodiester linkages at the 3' end of the oligonucleotide protects oligonucleotides from degradation. See, Tidd, D. M. and Warenius, H. M., Br. J. Cancer 60. 343–350 (1989); Shaw, J. P. et al., Nucleic Acids Res. 19, 747–750 (1991). Phosphoramidate, phosphorothioate, and methylphosphonate linkages are suitable for use in this invention. In addition, extensive modification of the phosphodiester backbone has been shown to impart stability and may allow for enhanced affinity and increased cellular permeation of oligonucleotides. See Milligan, et al., supra. Many different chemical strategies have been employed to replace the entire phosphodiester backbone with novel linkages. Id. The analogues of the oligonucleotides of the invention include phosphorothioate, phosphorodithioate, phosphorotrithioate, methylphosphonate, phosphoramidate, boranophosphate, phosphotriester, formacetal, 2'-O-methyl, Thioformacetal such as 3'-thioformacetal and 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene (methylimino) (MMI) and methyleneoxy (methylimino) (MOMI) linkages among others. The oligonucleotides of the invention may also be modified by addition of a terminal 1,3-propanediol or a terminal dodecanol, among others, or they may be conjugated to a polyethylene glycol, cholesterol, cholesteryl, dehydroepiandrosterone, dehydroepiandrosterone sulfate, dehydroepiandrosterone sulfatide, ubiquinone, dolichol, poly L-lysine, sulfatidic acid and fatty acid, among others. The oligos of the invention may also be modified by 2'-O-methoxyethyl, C-5-propynyl pyrimidine, C-5 methyl cytidine, C-5 ethynyl pyrimidine, 2'-propoxy, C-18 amine, N3'-P5' phosphoramidates, 3'-alkylamino, 2'-fluoro; 5-fluoro pyrimidine, 5-iodo pyrimidine, 5-bromo pyrimidine, 2'-borano, C-5 hexynyl pyrimidine, 2'-O-(2-methoxy)ethyl, 2'-O-aminopropyl, 5-(phenylethyl) and peptide nucleic acid interbase linkages. Phosphorothioate and methylphosphonate-modified oligonucleotides are particularly preferred because of their availability and suitability for automated oligonucleotide synthesis. Id. Anti-sense oligonucleotides containing modifications to the nucleotide base itself, e.g. a C-5 propyne, or to the sugar, e.g. a carbohydrate modification, are also aspects of the present invention.

Where appropriate, the antisense nucleotide may be administered in the form of their pharmaceutically acceptable salts or as a mixture.

Anti-sense oligonucleotides may be of any suitable length, e.g., from about 7 to 60 nucleotide in length, depending on the particular target being bound and their mode of delivery. Preferably the antisense oligonucleotide is directed to a gene or mRNA region containing a junction between intron and exon. Where the anti-sense oligonucleotide is directed to an intron/exon junction, it may either entirely overlie the junction or may be sufficiently close to the junction to inhibit the splicing out of the intervening exon during processing of precursor mRNA to mature mRNA, e.g., with the 3' or 5' terminus of the antisense oligonucleotide being positioned within about, for example, 10, 5, 3, or 2 nucleotide of the intron/exon junction. Also preferred are anti-sense oligonucleotides which overlap the initiation codon.

When practicing the present invention, the anti-sense oligonucleotides administered may be related in origin to the species to which it is administered. When treating humans, the anti-sense may be derived from human sequences. However, sequences obtained from one species are also suitable for administering to a second species.

The pharmaceutical compositions provided herein comprise nucleic acid(s) comprising the anti-sense oligonucleotide(s) described above and one or more surfactants. Suitable surfactants or surfactant components for enhancing the uptake of the anti-sense oligonucleotides of the invention include synthetic and natural as well as full and truncated forms of surfactant protein A, surfactant protein B, surfactant protein C, surfactant protein D and surfactant Protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phsophatidic acid, ubiquinones, lysophosphatidylethanolamine, lysophosphatidylcholine, palmitoyl-lysophosphatidylcholine, dehydroepiandrosterone, dilichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamelar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly (vinyl amine) with dextran and/or alkanoyl side chains, polyoxy ethylene 23 lauryl ether (Brij 35®), t-octyl phenoxy polyethoxy ethanol (Triton X-100®), dipalmitoyl phosphatidyl choline (DPPC) and phosphatidyl glycerol (PG) (ALEC®), tyloxapol (Exosurf®), phospholipids, fatty acids and surfactant-associated proteins (Survanta®) and $C_{22}H_{19}C_{10}$ (Atovaquone®), among others. These surfactants may be useed either as single or part of a multiple component surfactant in a formulation, or as covalently bound additions to the 5' and/or 3' ends of the anti-sense oligonucleotides (oligos).

These compositions are administered in amounts effective to reduce the expression of an adenosine receptor, such as the adenosine $A_1$, $A_{2b}$, or $A_3$ receptor by passing through a cell membrane and binding specifically with mRNA encoding an adenosine $A_1$, $A_{2b}$, or $A_3$ receptor in the cell and prevent its translation. In addition, the present oligos may be targeted to the adenosine $A_{2a}$ receptor, as long as they have some anti-$A_1$, $A_{2b}$, or $A_3$ receptor activity. Such compositions may contain a suitable pharmaceutically acceptable carrier, e.g., sterile pyrogen-free saline solution, and the like. The present pharmaceutical compositions may be formulated as topical and systemic formulations, in a variety of types, including oral, buccal, nasal, otical, rectal, inhalable, slow release, enteric coated, dermal, intradermal, injectable, and many more as is known in the art. The formulation of the invention may also comprise a hydrophobic carrier capable of passing through a cell membrane, e.g., in a liposome, with the liposomes carried in a pharmaceutically acceptable aqueous carrier. The oligonucleotides may also be coupled to a substance which inactivates mRNA, such as a ribozyme. The present compositions may be administered to a subject afflicted with a disease or condition associated with the stimulation of lung adenosine $A_1$, $A_{2a}$, $A_{2b}$ or $A_3$ receptors, such as any of the ones described above, in order to inhibit the activation of the adenosine receptors. The pharmaceutical formulation may also contain chimeric molecules comprising antisense oligonucleotides attached to molecules which are known to be internalized by cells either in a non-specific or in a tissue-specific manner. These oligonucleotide conjugates utilize cellular uptake pathways to increase the cellular concentrations of oligonucleotides. Examples of macromolecules used in this manner include transferrin, asialoglycoprotein, e.g. bound to oligonucleotides via polylysine, streptavidin, or other chemical linkages.

The anti-sense compound may be contained in the pharmaceutical formulation within a lipid particle or vesicle, such as a liposome or microcrystal. The lipid particles may be of any suitable structure, such as unilamellar or plurilamellar, so long as the antisense oligonucleotide is contained therein. Positively charged lipids such as N-[1-(2,3-dioleoyloxi)propyl]-N,N,N-trimethyl-ammoniumethylsulfate, or "DOTAP," are particularly preferred for such particles and vesicles. The preparation of such lipid particles is well known. See, e.g., U.S. Pat. No. 4,880,635 to Janoff et al.; U.S. Pat. No. 4,906,477 to Kurono et al.; U.S. Pat. No. 4,911,928 to Wallach; U.S. Pat. No. 4,917,951 to Wallach; U.S. Pat. No. 4,920,016 to Allen et al.; U.S. Pat. No. 4,921,757 to Wheatley et al.; etc.

The composition of the invention may be administered by any means which transports the anti-sense nucleotide and the surfactant composition to the lung. The antisense compounds disclosed herein may be administered to the lungs of a patient by any suitable means, but are preferably administered by inhalation of an aerosol comprised of respirable particles which comprise the anti-sense compound. The respirable particles may be liquid or solid, and they may optionally contain other therapeutic or diagnostic ingredients as well as other typical ingredients for a particular formulation. Examples of other agents are analgesics such as acetominophen, anilerdine, aspirin, buprenorphine, butabital, butorpphanol, Choline Salicylate, Codeine, Dezocine, Diclofenac, Diflunisal, Dihydrocodeine, Eleatoninin, Etodolac, Fenoprofen, Hydrocodone, Hydromorphone, Ibuprofen, Ketoprofen, Ketorolac, Levorphanol, Magnesium Salicylate, Meclofenamate, Mefenamic Acid, Meperidine, Methadone, Methotrimeprazine, Morphine, Nalbuphine, Naproxen, Opium, Oxycodone, Oxymorphone, Pentazocine, Phenobarbital, Propoxyphene, Salsalate, Sodium Salicylate, Tramadol and Narcotic analgesics in addition to those listed above. See, Mosby's Physician's GenRx. Anti-anxiety agents are also useful including Alprazolam, Bromazepam, Buspirone, Chlordiazepoxide, Chlormezanone, Clorazepate, Diazepam, Halazepam, Hydroxyzine, Ketaszolam, Lorazepam, Meprobamate, Oxazepam and Prazepam, among others. Anti-anxiety agents associated with mental depression, such as Chlordiazepoxide, Amitriptyline, Loxapine Maprotiline and Perphenazine, among others. Anti-inflammatory agents such as non-rheumatic Aspirin, Choline Salicylate, Diclofenac, Diflunisal, Etodolac, Fenoprofen, Floctafenine, Flurbiprofen, Ibuprofen, Indomethacin, Ketoprofen, Magnesium Salicylate, Meclofenamate, Mefenamic Acid, Naburnetone, Naproxen, Oxaprozin, Phenylbutazone, Piroxicam, Salsalate, Sodium Salicylate, Sulindac, Tenoxicam, Tiaprofenic Acid, Tolmetin, anti-inflammatories for ocular treatment such as Diclofenac, Flurbiprofen, Indomethacin, Ketorolac, Rimexolone (generally for post-operative treatment), anti-inflammatories for, non-infectious nasal applications such as Beclomethaxone, Budesonide, Dexamethasone, Flunisolide, Triamcinoline, and the like. Soporifics (anti-insomnia/sleep inducing agents) such as those utilized for treatment of insomnia, including Alprazolam, Bromazepam, Diazepam, Diphenhydramine, Doxylamine, Estazolam, Elurazepam, Halazepam, Ketazolam, Lorazepam, Nitrazepam, Prazepam Quazepam, Temazepam, Triazolam, Zolpidem and Sopiclone, among others. Sedatives including Diphenhydramine, Hydroxyzine, Methotrimeprazine, Promethazine, Propofol, Melatonin, Trimeprazine, and the like. Sedatives and agents used for treatment of petit mal and tremors, among other conditions, such as Amitriptyline HCl; Chlordiazepoxide, Amobarbital; Secobarbital, Aprobarbital, Butabarbital, Ethchiovynol, Glutethimide, L-Tryptophan, Mephobarbital, MethoHexital Na, Midazolam Hcl, Oxazepam, Pentobarbital Na, Phenobarbital, Secobarbital Na, Thiamylal Na, and many others. Agents used in the treatment of head trauma (Brain Injury/Ischemia), such as Enadoline HCl (e.g. for treatment of severe head injury; orphan status, Warner Lambert), cytoprotective agents, and agents for the treatment of menopause, menopausal symptoms (treatment), e.g. Ergotamine, Belladonna Alkaloids and Phenobarbital, for the treatment of menopausal vasomotor symptoms, e.g. Clonidine, Conjugated Estrogens and Medroxyprogesterone, Estradiol, Estradiol Cypionate, Estradiol Valerate, Estrogens, conjugated Estrogens, esterified Estrone, Estropipate, and Ethinyl Estradiol. Examples of agents for treatment of pre menstrual syndrome (PMS) are Progesterone, Progestin, Gonadotrophic Releasing Hormone, Oral contraceptives, Danazol, Luprolide Acetate. Vitamin B6. Examples of agents for treatment of emotional/psychiatric treatments such as Tricyclic Antidepressants, including Amitriptyline HCl (Elavil), Amitriptyline HCl, Perphenazine (Triavil) and Doxepin HCl (Sinequan). Examples of tranquilizers, anti-depressants and anti-anxiety agents are Diazepam (Valium), Lorazepam (Ativan), Alprazolam (Xanax), SSRI's (selective Serotonin reuptake inhibitors), Fluoxetine HCl (Prozac), Sertaline HCl (Zoloft), Paroxetine HCl (Paxil), Fluvoxamine Maleate (Luvox), Venlafaxine HCl (Effexor), Serotonin, Sertonin Agonists (Fenfluramine), and other over the counter (OTC) medications.

The composition of the present invention may be administered into the respiratory system as a formulation including particles of respirable size, e.g. particles of a size sufficiently small to pass through the nose, mouth and larynx upon inhalation and through the bronchi and alveoli of the lungs. In general, respirable particles range from about 0.5 to 10 microns in size. Particles of non-respirable size which are included in the aerosol tend to deposit in the throat and be swallowed, and the quantity of non-respirable particles in the aerosol is thus minimized. For nasal administration, a particle size in the range of 10–500 $\mu$m is preferred to ensure retention in the nasal cavity.

Liquid pharmaceutical compositions of active compound for producing an aerosol may be prepared by combining the antisense compound with a suitable vehicle, such as sterile pyrogen free water. Other therapeutic compounds may optionally be included.

Solid particulate compositions containing respirable dry particles of micronized antisense compound may be prepared by grinding dry antisense compound with a mortar and pestle, and then passing the micronized composition through a 400 mesh screen to break up or separate out large agglomerates. A solid particulate composition comprising of the antisense compound may optionally contain a dispersant which serves to facilitate the formation of an aerosol as well as other therapeutic compounds. A suitable dispersant is lactose, which may be blended with the antisense compound in any suitable ratio, e.g., a 1 to 1 ratio by weight.

The anti-sense compound may be administered in an anti-brochoconstriction, anti-allergy(ies) and/or anti-inflammatory effective amount, which amount depends upon the degree of disease being treated, the condition of the subject, the particular formulation, the route of administration, the timing of administration to a subject, etc. In general, intracellular concentrations of the oligonucleotide of from 0.05 to 50 $\mu$M, or more particularly 0.2 to 5 $\mu$M, are desirable. For administration to a subject such as a human, a dosage of about 0.01, 0.1, or 1 mg/Kg up to about 50, 100, or 150 mg/Kg or more is typically employed. However, other doses are also contemplated in this patent. Depending on the solubility of the active compound in any particular formulation, the daily dose may be divided among one or several unit dose administrations.

The aerosols of liquid particles comprising the antisense compound may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers comprise the active ingredient in a liquid carrier in an amount of up to 40% w/w preferably less than 20% w/w of the formulation. The carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, anti-oxidants, flavorings, volatile oils, buffering agents and emulsifiers and other formulation surfactants.

The aerosols of solid particles comprising the active compound and surfactant may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 $\mu$l, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, emulsifiers and other formulation surfactants, such as oleic acid or sorbitan trioleate, anti-oxidants and suitable flavoring agents.

The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly.

The following examples are provided to illustrate the present invention, and should not be construed as limiting thereon. In these examples, $\mu$M means micromolar, mL means milliliters, $\mu$m means micrometers, mm means millimeters, cm means centimeters, oC means degrees Celsius, $\mu$g means micrograms, mg means milligrams, g means grams, kg means kilograms, M means molar, and h means hours.

EXAMPLES

Example 1

Design and Synthesis of Anti-sense Oligonucleotides & Controls

The design of anti-sense oligonucleotides against the adenosine receptors is based on the primary and secondary structure of the target receptor mRNA. The anti-sense oligonucleotides are selected, and optimally modified, to target regions of mRNA which confer functional activity or stability to the mRNA and which preferably may overlap the initiation codon. For instance, regions that afford particularly strong binding, such as CG strings are preferred, i.e. runs of G and/or C, preferably at the 5'-end of the target region within the target gene or mRNA. However, other target sites within the molecule are suitable as well, particularly those which have low sequence overlapping with other gene sequences, thus increasing the specificity of the treatment.

Other oligonucleotides not totally complementary to the target mRNA, but containing identical nucleotide compositions on a w/w basis (controls), are included as controls in anti-sense experiments to demonstrate the specificity of the activity of the agents of this invention.

The primary and secondary structure of the human adenosine $A_1$ receptor mRNA was analyzed and used as described above to design anti-sense oligonucleotides, including the ones, whose sequences are provided. One anti-sense oligonucleotide (Oligo 1) was synthesized as a phosphorothioate, designated HAdA1AS, and has the following sequence:

5'-GAT GGA GGG CGG CAT GGC GGG-3' (SEQ ID NO:1)

As a control, a mis-matched phosphorothioate anti-sense nucleotide designated HAdA1MM was synthesized with the following sequence.

5'-GTA GCA GGC GGG GAT GGG GGC-3' (SEQ ID NO:2)

The oligonucleotides of SEQ. ID NOS: 1 and 2 shown above have identical base contents and general sequence structures. Homology searches in GENBANK (release 85.0) and EMBL (release 40.0) indicated that the anti-sense oligonucleotide was specific for the human and rabbit adenosine $A_1$ receptor genes, and that the mis-matched control was not a candidate for hybridization with any known gene sequence.

In the same manner, the primary and secondary structure of the human adenosine $A_3$ receptor mRNA was analyzed and various oligos selected, and the following two synthesized as phosphorothioate anti-sense oligonucleotides. The first anti-sense oligonucleotide (HAdA3AS1) synthesized has the following sequence.

5'-GTT GTT GGG CAT CTT GCC-3' (SEQ ID NO:3)

As a control, a mis-matched phosphorothioate anti-sense oligonucleotide (HAdA3MM1) was synthesized, which has the following sequence.

5'-GTA CTT GCG GAT CTA GGC-3' (SEQ ID NO:4)

The second phosphorothioate anti-sense oligonucleotide (HadA3AS2) has the following sequence.

5'-GTG GGC CTA GCT CTC GCC-3' (SEQ ID NO: 5)

As a control, its mis-matched oligonucleotide (HAdA3MM2) has the following sequence.

5'-GTC GGG GTA CCT GTC GGC-3' (SEQ ID NO:6)

All phosphorothioate oligonucleotides were synthesized on an Applied Biosystems Model 396 Oligonucleotide Synthesizer, and purified using NENSORB chromatography (DuPont, Md.).

Example 2

In Vitro Testing of $A_1$-Adenosine Receptor Antisense Oligonucleotides

The anti-sense oligonucleotide against the human $A_1$ receptor (SEQ ID NO:1) described above was tested for efficacy in an in vitro model utilizing lung adenocarcinoma cells HTB-54. HTB-54 lung adenocarcinoma cells were demonstrated to express the $A_1$ adenosine receptor using standard northern blotting procedures and receptor probes designed and synthesized in the laboratory.

HTB-54 human lung adenocarcinoma cells ($10^6$/100 mm tissue culture dish) were exposed to 5.0 µM HAdA1AS or HAdA1MM for 24 hours, with a fresh change of media and oligonucleotides after 12 hours of incubation. Following 24 hour exposure to the oligonucleotides, cells were harvested and their RNA extracted by standard procedures. A 21-mer probe corresponding to the region of mRNA targeted by the anti-sense (and therefore having the same sequence as the anti-sense, but not phosphorothioated) was synthesized and used to probe northern blots of RNA prepared from HAdA1AS-treated, HAdA1MM-treated and non-treated HTB-54 cells. These blots showed clearly that HAdA1AS but not HAdA1MM effectively reduced human adenosine receptor mRNA by >50%. This result showed that HAdA1AS is a good candidate for an anti-asthma drug since it depletes intracellular mRNA for the adenosine $A_1$ receptor, which is involved in asthma.

Example 3

In Vivo Efficacy of $A_1$ Adenosine Receptor Antisense Oligonucleotides

A fortuitous homology between the rabbit and human DNA sequences within the adenosine $A_1$ gene overlapping the initiation codon permitted the use of the phosphorothioate anti-sense oligonucleotides initially designed for use against the human adenosine $A_1$ receptor in a rabbit model.

Neonatal New Zealand white Pasteurella-free rabbits were immunized intraperitoneally within 24 hours of birth with 312 antigen units/mL house dust mite (*D. farinae*) extract (Berkeley Biologicals, Berkeley, Calif.), mixed with 10% kaolin. Immunizations were repeated weekly for the first month and then biweekly for the next 2 months. At 3–4 months of age, eight sensitized rabbits were anesthetized and relaxed with a mixture of ketamine hydrochloride (44 mg/kg) and acepromazine maleate (0.4 mg/kg) administered intramuscularly.

The rabbits were then laid supine in a comfortable position on a small molded, padded animal board and intubated with a 4.0-mm intratracheal tube (Mallinkrodt, Inc., Glens Falls, N.Y.). A polyethylene catheter of external diameter 2.4 mm with an attached latex balloon was passed into the esophagus and maintained at the same distance (approximately 16 cm) for the mouth throughout the experiments. The intratracheal tube was attached to a heated Fleisch pneumotachograph (size 00; DOM Medical, Richmond, Va.), and flow was measured using a Validyne differential pressure transducer (Model DP-45161927; Validyne Engineering Corp., Northridge, Calif.) driven by a Gould carrier amplifier (Model 11-4113; Gould Electronic, Cleveland, Ohio). The esophageal balloon was attached to one side of the differential pressure transducer, and the outflow of the intratracheal tube was connected to the opposite side of the pressure transducer to allow recording of transpulmonary pressure. Flow was integrated to give a continuous tidal volume, and measurements of total lung resistance (RL) and dynamic compliance (Cdyn) were calculated at isovolumetric and flow zero points, respectively, using an automated respiratory analyzer (Model 6; Buxco, Sharon, Conn.).

Animals were randomized and on Day 1 pretreatment values for PC50 were obtained for aerosolized adenosine. Anti-sense (HAdA1AS) or mismatched control (HAdA1MM) oligonucleotides were dissolved in sterile physiological saline at a concentration of 5000 µg (5 mg) per 1.0 ml. Animals were subsequently administered the aerosolized anti-sense or mismatch oligonucleotide via the intratracheal tube (approximately 5000 µg in a volume of 1.0 ml), twice daily for two days. Aerosols of either saline, adenosine, or anti-sense or mismatch oligonucleotides were generated by an ultrasonic nebulizer (DeVilbiss, Somerset, Pa.), producing aerosol droplets 80% of which were smaller than 5 µm in diameter.

In the first arm of the experiment, four randomly selected allergic rabbits were administered anti-sense oligonucleotide and four the mismatched control oligonucleotide. On the morning of the third day, PC50 values (the concentration of aerosolized adenosine in mg/ml required to reduce the dynamic compliance of the bronchial airway 50% from the baseline value) were obtained and compared to PC50 values obtained for these animals prior to exposure to oligonucleotide.

Following a 1 week interval, animals were crossed over, with those previously administered mismatch control oligonucleotide now administered anti-sense oligonucleotide, and those previously treated with anti-sense oligonucleotide now administered mismatch control oligonucleotide. Treatment methods and measurements were identical to those employed in the first arm of the experiment. It should be noted that in six of the eight animals treated with anti-sense oligonucleotide, adenosine-mediated bronchoconstriction could not be obtained up to the limit of solubility of adenosine, 20 mg/ml. For the purpose of calculation, PC50 values for these animals were set at 20 mg/ml. The values given therefore represent a minimum figure for anti-sense effectiveness. Actual effectiveness was higher. The results of this experiment are illustrated in both FIG. 1 and Table 1.

TABLE 1

Adenosine $A_1$ Receptor Anti-sense Oligonucleotide Effect upon PC50 Values in Asthmatic Rabbits

| Mismatch Control | | $A_1$ Receptor Anti-sense Oligonucleotide | |
|---|---|---|---|
| Pre oligonucleotide | Post oligonucleotide | Pre oligonucleotide | Post oligonucleotide |
| 3.56 ± 1.02 | 5.16 ± 1.93 | 2.36 ± 0.68 | >19.5 ± 0.34** |

Results are presented as the mean (n = 8)XSEM. Significance was determined by repeated-measures analysis of variance (ANOVA), and Tukey's protected t test. **Significantly different from all other groups, p < 0.01.

In both arms of the experiment, animals receiving the anti-sense oligonucleotide showed an order of magnitude increase in the dose of aerosolized adenosine required to reduce dynamic compliance of the lung by 50%. No effect of the mismatched control oligonucleotide upon PC50 values were observed. No toxicity was observed in any animal receiving either anti-sense or control inhaled oligonucleotide.

These results show clearly that the lung has exceptional potential as a target for anti-sense oligonucleotide-based therapeutic intervention in lung disease. They further show, in a model system which closely resembles human asthma, that down regulation of the adenosine $A_1$ receptor largely eliminates adenosine-mediated bronchoconstriction in asthmatic airways. Bronchial hyper-responsiveness in the allergic rabbit model of human asthma is an excellent endpoint for anti-sense intervention since the tissues involved in this response lie near to the point of contact with aerosolized oligonucleotides, and the model closely simulates an important human disease.

Example 4

Specificity of $A_1$-adenosine Receptor Anti-sense Oligonucleotide

At the conclusion of the crossover experiment of Example 3, airway smooth muscle from all rabbits was quantitatively analyzed for adenosine $A_1$ receptor number. As a control for the specificity of the anti-sense oligonucleotide, adenosine $A_2$ receptors, which should not have been affected, were also quantified.

Airway smooth muscle tissue was dissected from each rabbit and a membrane fraction prepared according to described methods (Kleinstein, J., and Glossman, H., Naunyn-Schmiedeberg's Arch. Pharmacol. 305, 191–200 (1978), with slight modifications. Crude plasma membrane preparations were stored at 70 oC. until the time of assay. Protein content was determined by the method of Bradford (M. Bradford, Anal. Biochem. 72, 240–254 (1976)). Frozen plasma membranes were thawed at room temperature and were incubated with 0.2 U/ml adenosine deaminase for 30 minutes at 37° C. to remove endogenous adenosine. The binding of [$^3$H] DPCPX ($A_1$ receptor-specific) or [$^3$H] CGS-21680 ($A_2$ receptor-specific) was measured as previously described. See, Ali, S., et al., J. Pharmacol. Exp. Ther. 268, 1328–1334 (1994); S. Ali et al., Am. J. Physiol. 266, L271–277 (1994).

Figure 2:
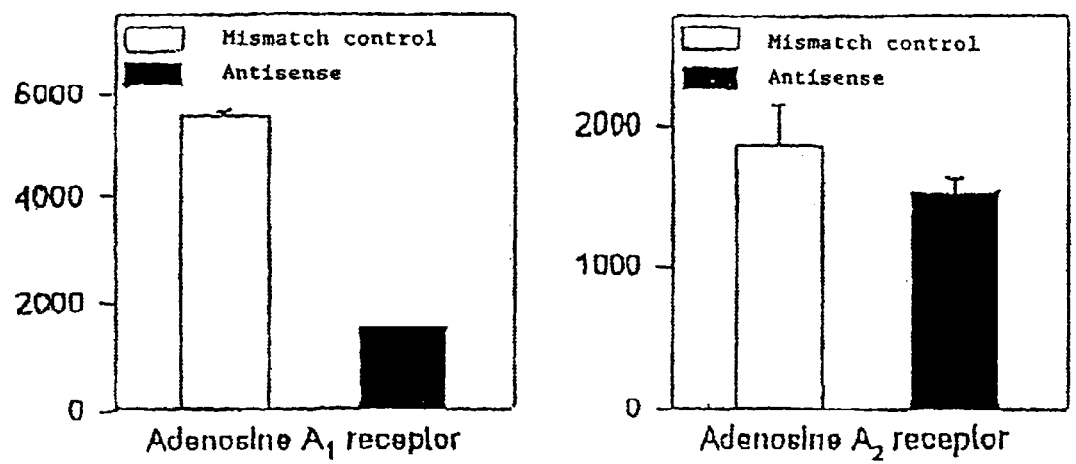
FIG. 2 illustrates the specificity of $A_1$ adenosine receptor anti-sense oligonucleotides as indicated by the $A_1$ and $A_2$ adenosine receptor number present in airway tissue treated with $A_1$ adenosine receptor anti-sensor oligonucleotides.

As illustrated in both FIG. 2 and Table 2, animals treated with adenosine $A_1$ anti-sense oligonucleotide in the crossover experiment had a nearly 75% decrease in $A_1$ receptor number compared to controls, as assayed by specific binding of the $A_1$-specific antagonist DPCPX. There was no change in adenosine $A_2$ receptor number, as assayed by specific binding of the $A_2$ receptor-specific agonist 2-[p-(2-carboxyethyl)-phenethylamino]-5'-(N-ethylcarboxamide) adenosine (CGS-21680).

TABLE 2

Specificity or Action of Adenosine $A_1$ Receptor Anti-sense Oligonucleotide

| | Mismatch Control Oligonucleotide (Mean ± SD) n = 8 | $A_1$-Anti-sense Oligonucleotide (Mean ± SD) n = 8 |
|---|---|---|
| $A_1$-Specific Binding | 1,105 ± 48** | 293 ± 18 |
| $A_2$-Specific Binding | 302 ± 22** | 442 ± 171 |

Significance was determined by repeated-measures analysis of variance (ANOVA), and Tukey's protected t test. **Significantly different from mismatch control, p < 0.01.

Example 5

In Vivo Response to Adenosine Challenge with & without Oligo I Pretreatment

Two hyper responsive monkeys (ascaris sensitive) were challenged with inhaled adenosine, with and without pretreatment with anti-sense oligo I (SEQ. ID NO: 1). The $PC_{40}$ adenosine was calculated from the data collected as being equivalent to that amount of adenosine in mg that causes a 40% decrease in dynamic compliance in hyper-responsive airways.

Figure 3B:
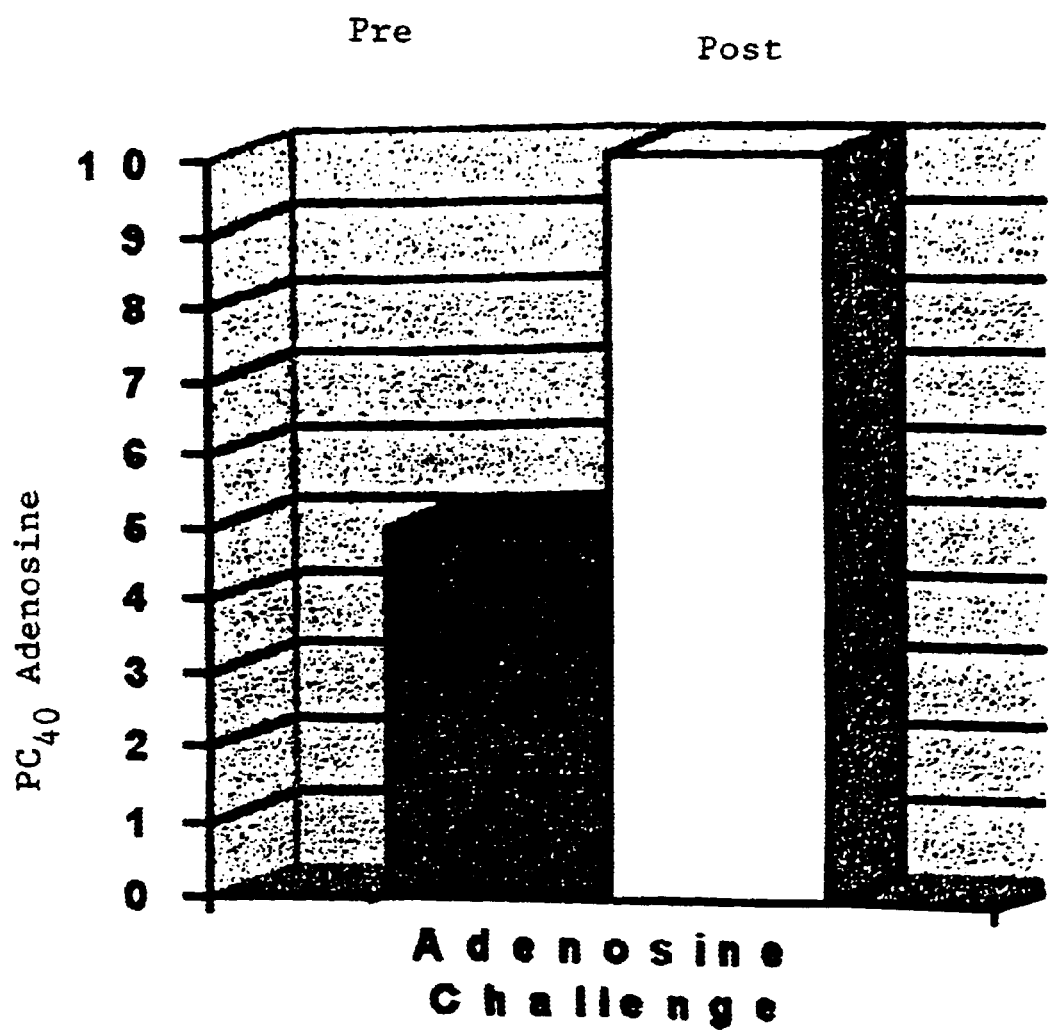

The Oligo I (SEQ. ID NO:1; EPI 2010) was subsequently administered at 10 mg/day for 2 days by inhalation. On the third day, PC adenosine was again measured. The results are shown in FIG. 3 accompanying this patent. The left bar shows the $PC_{40}$ adenosine value prior to treatment with Oligo I whereas the right bar shows the $PC_{40}$ adenosine taken after administration of Oligo I. As can be seen in FIG. 3, any sensitivity to adenosine was completely eliminated by the administration of the oligo of this invention in one animal, and substantially reduced in the second.

The foregoing examples are illustrative of the present invention, but are not to be constructed as limiting thereof. The invention is further defined by the following claims, with equivalents of the claims to be included therein.

---

What is claimed as being novel & unobvious in United States Letters Patent is:

1. An in vivo method of delivering a pharmaceutical composition to a target polynucleotide comprising administering to the airways of a subject said pharmaceutical composition of a respirable or inhalable particle size of about 0.5 μm to 500 μm in size comprising at least one oligonucleotide effective to alleviate hyper-responsiveness to adenosine or increased levels of adenosine, or to alleviate bronchoconstriction, asthma, or lung allergy, wherein the oligonucleotide is 4 to 60 nucleotides long and comprises 15% or less adenosine, wherein said oligonucleotide is antisense to a gene encoding an adenosine receptor associated with bronchoconstriction, and selected from the group consisting of genes encoding an adenosine $A_1$ receptor, adenosine$_{2b}$ receptor or adenosine $A_3$ receptor.

2. The method of claim 1, wherein the oligonucleotide comprises 10% or less adenosine.

3. The method of claim 2, wherein the oligonucleotide comprises 3% or less adenosine.

4. The method of claim 3, wherein the oligonucleotide is adenosine-free.

5. The method of claim 1, wherein the oligonucleotide is 9 to 51 nucleotides long.

6. The method of claim 5, wherein the oligonucleotide is 18 or 21 nucleotides long.

7. The method of claim 1, wherein the pharmaceutical composition is administered by inhalation directly to the airway or lung of the subject.

8. The method of claim 1, wherein the oligonucleotide is antisense to the initiation codon, the coding region or the 5' or 3' intron-exon junction of a gene encoding a an adenosine receptor associated with bronchoconstriction, and selected from the group consisting of genes encoding an adenosine $A_1$ receptor, adenosine$_{2b}$ receptor or adenosine $A_3$ receptor and it is associated with hyper-responsiveness to adenosine, hyper-responsiveness to increased levels of adenosine, hyper-responsiveness to increased levels of an adenosine receptor, bronchoconstriction, asthma, lung allergy, or lung inflammation, or is antisense to the corresponding mRNA thereof.

9. The method of claim 1, wherein the particle size is about 0.5 μm to about 10 μm in size.

10. The method of claim 1, wherein the particle size is 10 μm to 500 μm in size.

11. The method of claim 1, wherein the pharmaceutical composition further comprises a surfactant.

12. The method of claim 1, wherein the hyper-responsiveness to adenosine, hyper-responsiveness to increased levels of adenosine, hyper-responsiveness to increased levels of an adenosine receptor, bronchoconstriction, asthma, lung allergy, or lung inflammation is associated with allergy, chronic obstructive pulmonary disease, asthma, acute respiratory distress syndrome, respiratory distress syndrome, or a side effect of adenosine administration.

13. The method of claim 1, wherein the nucleic acid is administered in an amount of about 0.005 to about 150 mg/kg body weight.

14. The method of claim 1, wherein said method is a prophylactic or therapeutic method.

15. The method of claim 1, wherein the oligonucleotide is antisense to the initiation codon, the coding region or the 5' or 3' intron-exon junctions of a gene encoding an adenosine $A_1$ receptor, adenosine $A_{2b}$ receptor or adenosine $A_3$ receptor.

16. An in vivo method of delivering a pharmaceutical composition to a target polynucleotide comprising administering to the airways of a subject said pharmaceutical composition of a respirable or inhalable particle size of about 0.5 μm to 500 μm in size comprising at least one oligonucleotide, wherein the oligonucleotide comprises the sequence of SEQ ID NO: 1, SEQ ID NO: 3, SEQ ID NO: 5 or SEQ ID NO: 7 to SEQ ID NO: 966, or SEQ ID NO: 1, SEQ ID NO: 3, SEQ ID NO: 5 or SEQ ID NO: 7 to SEQ ID NO: 966, wherein at least one mononucleotide is linked or modified by one or more of phosphorothioate, phosphorodithioate, methylphosphonate, phosphoramidate, boranophosphate, phosphotriester, formacetal, 2'-O-methyl, thioformacetal, 5'-thioether, carbonate, 5'-N-carbamate, sulfate, sulfonate, sulfamate, sulfonamide, sulfone, sulfite, sulfoxide, sulfide, hydroxylamine, methylene (methylimino) and methyleneoxy (methylimino), terminal 1,3-propanediol, terminal dodecanol, 2-0-methoxyethyl,C-5-propynyl pyrimidine, C-5 methyl cytidine, C-5 ethynyl pyrimidine, 2' propoxy, C-18 amine, N3'-P5 phosphoramidates, 3'-alkylamino, 2'-fluoro pyrimidine, 5-fluoro pyrimidine, 5-iodo pyrimidine, 5-bromo pyrimidine, 2'-borano, C-5 hexynyl pyrimidine, 2'-O-(2-methoxy)ethyl, 2'-O-aminopropyl, 5-(phenylethyl) or a peptide nucleic acid inter-base linkages or conjugated to a polyethylene glycol, cholesterol, cholesteryl, dehydroepiandrosterone, dehydroepiandrosterone sulfate, dehydroepiandrosterone sulfatide, ubiquinone, dolichol, poly L-lysine, sulfatidic acid or a fatty acid.

\* \* \* \* \*

SEQUENCE LISTING (1) GENERAL INFORMATION:

(iii) NUMBER OF SEQUENCES: 996

(2) INFORMATION FOR SEQ ID NO: 1:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 1:

GATGGAGGGC GGCATGGCGG G                                 21

(2) INFORMATION FOR SEQ ID NO: 2:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 2:

GTAGCAGGCG GGGATGGGGG C                                 21

(2) INFORMATION FOR SEQ ID NO: 3:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 3:

GTTGTTGGGC ATCTTGCC                                    18

(2) INFORMATION FOR SEQ ID NO: 4:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 4:

GTACTTGCGG ATCTAGGC                                    18

(2) INFORMATION FOR SEQ ID NO: 5:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 5:

```
GTGGGCCTAG CTCTCGCC                                                   18

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GTCGGGGTAC CTGTCGGC                                                   18

(2) INFORMATION FOR SEQ ID NO: 7:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GGCGGCCTGG AAAGCTGAGA TGGAGGGCGG CATGGCGGGC ACAGGCTGGG C              51

(2) INFORMATION FOR SEQ ID NO: 8:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

GGCGGCCTGG AAAGCTGAGA TGGAGGGCGG CATGGCGGGC ACAGGCTGGG                50

(2) INFORMATION FOR SEQ ID NO: 9:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

GGCGGCCTGG AAAGCTGAGA TGGAGGGCGG CATGGCGGGC ACAGGCTGG                 49

(2) INFORMATION FOR SEQ ID NO: 10:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GGCGGCCTGG AAAGCTGAGA TGGAGGGCGG CATGGCGGGC ACAGGCTG                  48
```

(2) INFORMATION FOR SEQ ID NO: 11:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GGCGGCCTGG AAAGCTGAGA TGGAGGGCGG CATGGCGGGC ACAGGCT                47

(2) INFORMATION FOR SEQ ID NO: 12:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

GGCGGCCTGG AAAGCTGAGA TGGAGGGCGG CATGGCGGGC ACAGGC                 46

(2) INFORMATION FOR SEQ ID NO: 13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GGCGGCCTGG AAAGCTGAGA TGGAGGGCGG CATGGCGGGC ACAGG                  45

(2) INFORMATION FOR SEQ ID NO: 14:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

GGCGGCCTGG AAAGCTGAGA TGGAGGGCGG CATGGCGGGC ACAG                   44

(2) INFORMATION FOR SEQ ID NO: 15:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

GGCGGCCTGG AAAGCTGAGA TGGAGGGCGG CATGGCGGGC ACA                    43

(2) INFORMATION FOR SEQ ID NO: 16:

(i) SEQUENCE CHARACTERISTICS:
        (A) LENGTH: 42 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

GGCGGCCTGG AAAGCTGAGA TGGAGGGCGG CATGGCGGGC AC          42

(2) INFORMATION FOR SEQ ID NO: 17:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GGCGGCCTGG AAAGCTGAGA TGGAGGGCGG CATGGCGGGC A           41

(2) INFORMATION FOR SEQ ID NO: 18:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

GGCGGCCTGG AAAGCTGAGA TGGAGGGCGG CATGGCGGGC             40

(2) INFORMATION FOR SEQ ID NO: 19:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

GGCGGCCTGG AAAGCTGAGA TGGAGGGCGG CATGGCGGG              39

(2) INFORMATION FOR SEQ ID NO: 20:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

GGCGGCCTGG AAAGCTGAGA TGGAGGGCGG CATGGCGG               38

(2) INFORMATION FOR SEQ ID NO: 21:

(i) SEQUENCE CHARACTERISTICS:
        (A) LENGTH: 37 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO: 21:

GGCGGCCTGG AAAGCTGAGA TGGAGGGCGG CATGGCG                37

(2) INFORMATION FOR SEQ ID NO: 22:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

GGCGGCCTGG AAAGCTGAGA TGGAGGGCGG CATGGC                 36

(2) INFORMATION FOR SEQ ID NO: 23:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

GGCGGCCTGG AAAGCTGAGA TGGAGGGCGG CATGG                  35

(2) INFORMATION FOR SEQ ID NO: 24:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

GGCGGCCTGG AAAGCTGAGA TGGAGGGCGG CATG                   34

(2) INFORMATION FOR SEQ ID NO: 25:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

GGCGGCCTGG AAAGCTGAGA TGGAGGGCGG CAT                    33

(2) INFORMATION FOR SEQ ID NO: 26:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

```
GGCGGCCTGG AAAGCTGAGA TGGAGGGCGG CA                                32

(2) INFORMATION FOR SEQ ID NO: 27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

GGCGGCCTGG AAAGCTGAGA TGGAGGGCGG C                                 31

(2) INFORMATION FOR SEQ ID NO: 28:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

GGCGGCCTGG AAAGCTGAGA TGGAGGGCGG                                   30

(2) INFORMATION FOR SEQ ID NO: 29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 29:

GGCGGCCTGG AAAGCTGAGA TGGAGGGCG                                    29

(2) INFORMATION FOR SEQ ID NO: 30:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

GGCGGCCTGG AAAGCTGAGA TGGAGGGC                                     28

(2) INFORMATION FOR SEQ ID NO: 31:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

GGCGGCCTGG AAAGCTGAGA TGGAGGG                                      27

(2) INFORMATION FOR SEQ ID NO: 32:
```

```
    (i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

GGCGGCCTGG AAAGCTGAGA TGGAGG                                              26

(2) INFORMATION FOR SEQ ID NO: 33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

GGCGGCCTGG AAAGCTGAGA TGGAG                                               25

(2) INFORMATION FOR SEQ ID NO: 34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

GGCGGCCTGG AAAGCTGAGA TGGA                                                24

(2) INFORMATION FOR SEQ ID NO: 35:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

GGCGGCCTGG AAAGCTGAGA TGG                                                 23

(2) INFORMATION FOR SEQ ID NO: 36:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

GGCGGCCTGG AAAGCTGAGA TG                                                  22

(2) INFORMATION FOR SEQ ID NO: 37:

(i) SEQUENCE CHARACTERISTICS:
        (A) LENGTH: 21 base pairs
        (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO: 37:

GGCGGCCTGG AAAGCTGAGA T                                          21

(2) INFORMATION FOR SEQ ID NO: 38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

GGCGGCCTGG AAAGCTGAGA                                            20

(2) INFORMATION FOR SEQ ID NO: 39:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

GGCGGCCTGG AAAGCTGAG                                             19

(2) INFORMATION FOR SEQ ID NO: 40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

GGCGGCCTGG AAAGCTGA                                              18

(2) INFORMATION FOR SEQ ID NO: 41:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

GGCGGCCTGG AAAGCTG                                               17

(2) INFORMATION FOR SEQ ID NO: 42:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 42:

GGCGGCCTGG AAAGCT                                                    16

(2) INFORMATION FOR SEQ ID NO: 43:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

GGCGGCCTGG AAAGC                                                 15

(2) INFORMATION FOR SEQ ID NO: 44:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

GGCGGCCTGG AAAG                                                      14

(2) INFORMATION FOR SEQ ID NO: 45:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 45:

GGCGGCCTGG AAA                                                       13

(2) INFORMATION FOR SEQ ID NO: 46:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 46:

GGCGGCCTGG AA                                                    12

(2) INFORMATION FOR SEQ ID NO: 47:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

GGCGGCCTGG A                                                         11

(2) INFORMATION FOR SEQ ID NO: 48:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 48:

GGCGGCCTGG                                                              10

(2) INFORMATION FOR SEQ ID NO: 49:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 49:

GCGGCCTGGA AAGCTGAGAT GGAGGGCGGC ATGGCGGGCA CAGGCTGGGC          50

(2) INFORMATION FOR SEQ ID NO: 50:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 50:

GCGGCCTGGA AAGCTGAGAT GGAGGGCGGC ATGGCGGGCA CAGGCTGGG           49

(2) INFORMATION FOR SEQ ID NO: 51:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 51:

GCGGCCTGGA AAGCTGAGAT GGAGGGCGGC ATGGCGGGCA CAGGCTGG            48

(2) INFORMATION FOR SEQ ID NO: 52:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

GCGGCCTGGA AAGCTGAGAT GGAGGGCGGC ATGGCGGGCA CAGGCTG             47

(2) INFORMATION FOR SEQ ID NO: 53:

```
    (i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 53:

GCGGCCTGGA AAGCTGAGAT GGAGGGCGGC ATGGCGGGCA CAGGCT              46

(2) INFORMATION FOR SEQ ID NO: 54:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 54:

GCGGCCTGGA AAGCTGAGAT GGAGGGCGGC ATGGCGGGCA CAGGC               45

(2) INFORMATION FOR SEQ ID NO: 55:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 55:

GCGGCCTGGA AAGCTGAGAT GGAGGGCGGC ATGGCGGGCA CAGG                44

(2) INFORMATION FOR SEQ ID NO: 56:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

GCGGCCTGGA AAGCTGAGAT GGAGGGCGGC ATGGCGGGCA CAG                 43

(2) INFORMATION FOR SEQ ID NO: 57:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 57:

GCGGCCTGGA AAGCTGAGAT GGAGGGCGGC ATGGCGGGCA CA                  42

(2) INFORMATION FOR SEQ ID NO: 58:

(i) SEQUENCE CHARACTERISTICS:
        (A) LENGTH: 41 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO: 58:

GCGGCCTGGA AAGCTGAGAT GGAGGGCGGC ATGGCGGGCA C                              41

(2) INFORMATION FOR SEQ ID NO: 59:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 59:

GCGGCCTGGA AAGCTGAGAT GGAGGGCGGC ATGGCGGGCA                                40

(2) INFORMATION FOR SEQ ID NO: 60:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

GCGGCCTGGA AAGCTGAGAT GGAGGGCGGC ATGGCGGGC                                 39

(2) INFORMATION FOR SEQ ID NO: 61:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 61:

GCGGCCTGGA AAGCTGAGAT GGAGGGCGGC ATGGCGGG                                  38

(2) INFORMATION FOR SEQ ID NO: 62:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 62:

GCGGCCTGGA AAGCTGAGAT GGAGGGCGGC ATGGCGG                                   37

(2) INFORMATION FOR SEQ ID NO: 63:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 63:

GCGGCCTGGA AAGCTGAGAT GGAGGGCGGC ATGGCG                                          36

(2) INFORMATION FOR SEQ ID NO: 64:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 64:

GCGGCCTGGA AAGCTGAGAT GGAGGGCGGC ATGGC                                           35

(2) INFORMATION FOR SEQ ID NO: 65:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 65:

GCGGCCTGGA AAGCTGAGAT GGAGGGCGGC ATGG                                            34

(2) INFORMATION FOR SEQ ID NO: 66:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 66:

GCGGCCTGGA AAGCTGAGAT GGAGGGCGGC ATG                                             33

(2) INFORMATION FOR SEQ ID NO: 67:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 67:

GCGGCCTGGA AAGCTGAGAT GGAGGGCGGC AT                                              32

(2) INFORMATION FOR SEQ ID NO: 68:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 68:

GCGGCCTGGA AAGCTGAGAT GGAGGGCGGC A                                               31

(2) INFORMATION FOR SEQ ID NO: 69:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 69:

GCGGCCTGGA AAGCTGAGAT GGAGGGCGGC                                         30

(2) INFORMATION FOR SEQ ID NO: 70:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 70:

GCGGCCTGGA AAGCTGAGAT GGAGGGCGG                                          29

(2) INFORMATION FOR SEQ ID NO: 71:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 71:

GCGGCCTGGA AAGCTGAGAT GGAGGGCG                                           28

(2) INFORMATION FOR SEQ ID NO: 72:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 72:

GCGGCCTGGA AAGCTGAGAT GGAGGGC                                            27

(2) INFORMATION FOR SEQ ID NO: 73:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 73:

GCGGCCTGGA AAGCTGAGAT GGAGGG                                             26

(2) INFORMATION FOR SEQ ID NO: 74:

(i) SEQUENCE CHARACTERISTICS:

-continued (A) LENGTH: 25 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 74:

GCGGCCTGGA AAGCTGAGAT GGAGG                                            25

(2) INFORMATION FOR SEQ ID NO: 75:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 75:

GCGGCCTGGA AAGCTGAGAT GGAG                                             24

(2) INFORMATION FOR SEQ ID NO: 76:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 76:

GCGGCCTGGA AAGCTGAGAT GGA                                              23

(2) INFORMATION FOR SEQ ID NO: 77:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 77:

GCGGCCTGGA AAGCTGAGAT GG                                               22

(2) INFORMATION FOR SEQ ID NO: 78:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 78:

GCGGCCTGGA AAGCTGAGAT G                                                21

(2) INFORMATION FOR SEQ ID NO: 79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 79:

GCGGCCTGGA AAGCTGAGAT                                                      20

(2) INFORMATION FOR SEQ ID NO: 80:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 80:

GCGGCCTGGA AAGCTGAGA                                                       19

(2) INFORMATION FOR SEQ ID NO: 81:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 81:

GCGGCCTGGA AAGCTGAG                                                        18

(2) INFORMATION FOR SEQ ID NO: 82:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 82:

GCGGCCTGGA AAGCTGA                                                         17

(2) INFORMATION FOR SEQ ID NO: 83:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 83:

GCGGCCTGGA AAGCTG                                                          16

(2) INFORMATION FOR SEQ ID NO: 84:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 84:

-continued

```
GCGGCCTGGA AAGCT                                                        15

(2) INFORMATION FOR SEQ ID NO: 85:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 85:

GCGGCCTGGA AAGC                                                         14

(2) INFORMATION FOR SEQ ID NO: 86:

(i) SEQUENCE CHARACTERISTICS:
         (A) LENGTH: 13 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 86:

GCGGCCTGGA AAG                                                          13

(2) INFORMATION FOR SEQ ID NO: 87:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 87:

GCGGCCTGGA AA                                                           12

(2) INFORMATION FOR SEQ ID NO: 88:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 88:

GCGGCCTGGA A                                                            11

(2) INFORMATION FOR SEQ ID NO: 89:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 89:

GCGGCCTGGA                                                              10
```

(2) INFORMATION FOR SEQ ID NO: 90:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 90:

CGGCCTGGAA AGCTGAGATG GAGGGCGGCA TGGCGGGCAC AGGCTGGGC                49

(2) INFORMATION FOR SEQ ID NO: 91:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 91:

CGGCCTGGAA AGCTGAGATG GAGGGCGGCA TGGCGGGCAC AGGCTGGG                 48

(2) INFORMATION FOR SEQ ID NO: 92:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 92:

CGGCCTGGAA AGCTGAGATG GAGGGCGGCA TGGCGGGCAC AGGCTGG                  47

(2) INFORMATION FOR SEQ ID NO: 93:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 93:

CGGCCTGGAA AGCTGAGATG GAGGGCGGCA TGGCGGGCAC AGGCTG                   46

(2) INFORMATION FOR SEQ ID NO: 94:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 94:

CGGCCTGGAA AGCTGAGATG GAGGGCGGCA TGGCGGGCAC AGGCT                    45

(2) INFORMATION FOR SEQ ID NO: 95:

(i) SEQUENCE CHARACTERISTICS:
        (A) LENGTH: 44 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 95:

CGGCCTGGAA AGCTGAGATG GAGGGCGGCA TGGCGGGCAC AGGC             44

(2) INFORMATION FOR SEQ ID NO: 96:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 96:

CGGCCTGGAA AGCTGAGATG GAGGGCGGCA TGGCGGGCAC AGG              43

(2) INFORMATION FOR SEQ ID NO: 97:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 97:

CGGCCTGGAA AGCTGAGATG GAGGGCGGCA TGGCGGGCAC AG               42

(2) INFORMATION FOR SEQ ID NO: 98:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 98:

CGGCCTGGAA AGCTGAGATG GAGGGCGGCA TGGCGGGCAC A                41

(2) INFORMATION FOR SEQ ID NO: 99:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 99:

CGGCCTGGAA AGCTGAGATG GAGGGCGGCA TGGCGGGCAC                  40

(2) INFORMATION FOR SEQ ID NO: 100:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 100:

CGGCCTGGAA AGCTGAGATG GAGGGCGGCA TGGCGGGCA                              39

(2) INFORMATION FOR SEQ ID NO: 101:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 101:

CGGCCTGGAA AGCTGAGATG GAGGGCGGCA TGGCGGGC                               38

(2) INFORMATION FOR SEQ ID NO: 102:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 102:

CGGCCTGGAA AGCTGAGATG GAGGGCGGCA TGGCGGG                                37

(2) INFORMATION FOR SEQ ID NO: 103:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 103:

CGGCCTGGAA AGCTGAGATG GAGGGCGGCA TGGCGG                                 36

(2) INFORMATION FOR SEQ ID NO: 104:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 104:

CGGCCTGGAA AGCTGAGATG GAGGGCGGCA TGGCG                                  35

(2) INFORMATION FOR SEQ ID NO: 105:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 105:

```
CGGCCTGGAA AGCTGAGATG GAGGGCGGCA TGGC                              34
```

(2) INFORMATION FOR SEQ ID NO: 106:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 106:

```
CGGCCTGGAA AGCTGAGATG GAGGGCGGCA TGG                               33
```

(2) INFORMATION FOR SEQ ID NO: 107:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 107:

```
CGGCCTGGAA AGCTGAGATG GAGGGCGGCA TG                                32
```

(2) INFORMATION FOR SEQ ID NO: 108:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 108:

```
CGGCCTGGAA AGCTGAGATG GAGGGCGGCA T                                 31
```

(2) INFORMATION FOR SEQ ID NO: 109:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 109:

```
CGGCCTGGAA AGCTGAGATG GAGGGCGGCA                                   30
```

(2) INFORMATION FOR SEQ ID NO: 110:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 110:

```
CGGCCTGGAA AGCTGAGATG GAGGGCGGC                                    29
```

(2) INFORMATION FOR SEQ ID NO: 111:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 111:

CGGCCTGGAA AGCTGAGATG GAGGGCGG                                              28

(2) INFORMATION FOR SEQ ID NO: 112:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 112:

CGGCCTGGAA AGCTGAGATG GAGGGCG                                               27

(2) INFORMATION FOR SEQ ID NO: 113:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 113:

CGGCCTGGAA AGCTGAGATG GAGGGC                                                26

(2) INFORMATION FOR SEQ ID NO: 114:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 114:

CGGCCTGGAA AGCTGAGATG GAGGG                                                 25

(2) INFORMATION FOR SEQ ID NO: 115:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 115:

CGGCCTGGAA AGCTGAGATG GAGG                                                  24

(2) INFORMATION FOR SEQ ID NO: 116:

(i) SEQUENCE CHARACTERISTICS:
            (A) LENGTH: 23 base pairs
            (B) TYPE: nucleic acid

```
          (C) STRANDEDNESS: single
          (D) TOPOLOGY: linear (ii) MOLECULE TYPE: DNA (genomic)

(xi) SEQUENCE DESCRIPTION: SEQ ID NO: 116:

CGGCCTGGAA AGCTGAGATG GAG                                              23

(2) INFORMATION FOR SEQ ID NO: 117:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 117:

CGGCCTGGAA AGCTGAGATG GA                                               22

(2) INFORMATION FOR SEQ ID NO: 118:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 118:

CGGCCTGGAA AGCTGAGATG G                                                21

(2) INFORMATION FOR SEQ ID NO: 119:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 119:

CGGCCTGGAA AGCTGAGATG                                                  20

(2) INFORMATION FOR SEQ ID NO: 120:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 120:

CGGCCTGGAA AGCTGAGAT                                                   19

(2) INFORMATION FOR SEQ ID NO: 121:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)
```

(xi) SEQUENCE DESCRIPTION: SEQ ID NO: 121:

CGGCCTGGAA AGCTGAGA                                                18

(2) INFORMATION FOR SEQ ID NO: 122:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 122:

CGGCCTGGAA AGCTGAG                                                 17

(2) INFORMATION FOR SEQ ID NO: 123:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 123:

CGGCCTGGAA AGCTGA                                                  16

(2) INFORMATION FOR SEQ ID NO: 124:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 124:

CGGCCTGGAA AGCTG                                                   15

(2) INFORMATION FOR SEQ ID NO: 125:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 125:

CGGCCTGGAA AGCT                                                    14

(2) INFORMATION FOR SEQ ID NO: 126:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 126:

CGGCCTGGAA AGC                                                     13

(2) INFORMATION FOR SEQ ID NO: 127:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 127:

CGGCCTGGAA AG                                                12

(2) INFORMATION FOR SEQ ID NO: 128:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 128:

CGGCCTGGAA A                                                 11

(2) INFORMATION FOR SEQ ID NO: 129:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 129:

CGGCCTGGAA                                                   10

(2) INFORMATION FOR SEQ ID NO: 130:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 130:

GGCCTGGAAA GCTGAGATGG AGGGCGGCAT GGCGGGCACA GGCTGGGC        48

(2) INFORMATION FOR SEQ ID NO: 131:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 131:

GGCCTGGAAA GCTGAGATGG AGGGCGGCAT GGCGGGCACA GGCTGGG         47

(2) INFORMATION FOR SEQ ID NO: 132:

(i) SEQUENCE CHARACTERISTICS:
    (A) LENGTH: 46 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 132:

GGCCTGGAAA GCTGAGATGG AGGGCGGCAT GGCGGGCACA GGCTGG                46

(2) INFORMATION FOR SEQ ID NO: 133:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 133:

GGCCTGGAAA GCTGAGATGG AGGGCGGCAT GGCGGGCACA GGCTG                 45

(2) INFORMATION FOR SEQ ID NO: 134:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 134:

GGCCTGGAAA GCTGAGATGG AGGGCGGCAT GGCGGGCACA GGCT                  44

(2) INFORMATION FOR SEQ ID NO: 135:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 135:

GGCCTGGAAA GCTGAGATGG AGGGCGGCAT GGCGGGCACA GGC                   43

(2) INFORMATION FOR SEQ ID NO: 136:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 136:

GGCCTGGAAA GCTGAGATGG AGGGCGGCAT GGCGGGCACA GG                    42

(2) INFORMATION FOR SEQ ID NO: 137:

(i) SEQUENCE CHARACTERISTICS:
        (A) LENGTH: 41 base pairs
        (B) TYPE: nucleic acid
        (C) STRANDEDNESS: single -continued (D) TOPOLOGY: linear (ii) MOLECULE TYPE: DNA (genomic)

(xi) SEQUENCE DESCRIPTION: SEQ ID NO: 137:

GGCCTGGAAA GCTGAGATGG AGGGCGGCAT GGCGGGCACA G              41

(2) INFORMATION FOR SEQ ID NO: 138:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 138:

GGCCTGGAAA GCTGAGATGG AGGGCGGCAT GGCGGGCACA              40

(2) INFORMATION FOR SEQ ID NO: 139:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 139:

GGCCTGGAAA GCTGAGATGG AGGGCGGCAT GGCGGGCAC              39

(2) INFORMATION FOR SEQ ID NO: 140:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 140:

GGCCTGGAAA GCTGAGATGG AGGGCGGCAT GGCGGGCA              38

(2) INFORMATION FOR SEQ ID NO: 141:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 141:

GGCCTGGAAA GCTGAGATGG AGGGCGGCAT GGCGGGC              37

(2) INFORMATION FOR SEQ ID NO: 142:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO: 142:

GGCCTGGAAA GCTGAGATGG AGGGCGGCAT GGCGGG                                    36

(2) INFORMATION FOR SEQ ID NO: 143:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 143:

GGCCTGGAAA GCTGAGATGG AGGGCGGCAT GGCGG                                     35

(2) INFORMATION FOR SEQ ID NO: 144:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 144:

GGCCTGGAAA GCTGAGATGG AGGGCGGCAT GGCG                                      34

(2) INFORMATION FOR SEQ ID NO: 145:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 145:

GGCCTGGAAA GCTGAGATGG AGGGCGGCAT GGC                                       33

(2) INFORMATION FOR SEQ ID NO: 146:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 146:

GGCCTGGAAA GCTGAGATGG AGGGCGGCAT GG                                        32

(2) INFORMATION FOR SEQ ID NO: 147:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 147:

GGCCTGGAAA GCTGAGATGG AGGGCGGCAT G                                         31

(2) INFORMATION FOR SEQ ID NO: 148:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 148:

GGCCTGGAAA GCTGAGATGG AGGGCGGCAT                                       30

(2) INFORMATION FOR SEQ ID NO: 149:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 149:

GGCCTGGAAA GCTGAGATGG AGGGCGGCA                                        29

(2) INFORMATION FOR SEQ ID NO: 150:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 150:

GGCCTGGAAA GCTGAGATGG AGGGCGGC                                         28

(2) INFORMATION FOR SEQ ID NO: 151:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 151:

GGCCTGGAAA GCTGAGATGG AGGGCGG                                          27

(2) INFORMATION FOR SEQ ID NO: 152:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 152:

GGCCTGGAAA GCTGAGATGG AGGGCG                                           26

(2) INFORMATION FOR SEQ ID NO: 153:

(i) SEQUENCE CHARACTERISTICS:

(A) LENGTH: 25 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 153:

GGCCTGGAAA GCTGAGATGG AGGGC                                              25

(2) INFORMATION FOR SEQ ID NO: 154:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 154:

GGCCTGGAAA GCTGAGATGG AGGG                                               24

(2) INFORMATION FOR SEQ ID NO: 155:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 155:

GGCCTGGAAA GCTGAGATGG AGG                                                23

(2) INFORMATION FOR SEQ ID NO: 156:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 156:

GGCCTGGAAA GCTGAGATGG AG                                                 22

(2) INFORMATION FOR SEQ ID NO: 157:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 157:

GGCCTGGAAA GCTGAGATGG A                                                  21

(2) INFORMATION FOR SEQ ID NO: 158:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 158:

GGCCTGGAAA GCTGAGATGG                                                    20

(2) INFORMATION FOR SEQ ID NO: 159:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 159:

GGCCTGGAAA GCTGAGATG                                                     19

(2) INFORMATION FOR SEQ ID NO: 160:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 160:

GGCCTGGAAA GCTGAGAT                                                      18

(2) INFORMATION FOR SEQ ID NO: 161:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 161:

GGCCTGGAAA GCTGAGA                                                       17

(2) INFORMATION FOR SEQ ID NO: 162:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 162:

GGCCTGGAAA GCTGAG                                                        16

(2) INFORMATION FOR SEQ ID NO: 163:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 163:

-continued

GGCCTGGAAA GCTGA                                                    15

(2) INFORMATION FOR SEQ ID NO: 164:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 164:

GGCCTGGAAA GCTG                                                     14

(2) INFORMATION FOR SEQ ID NO: 165:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 165:

GGCCTGGAAA GCT                                                      13

(2) INFORMATION FOR SEQ ID NO: 166:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 166:

GGCCTGGAAA GC                                                       12

(2) INFORMATION FOR SEQ ID NO: 167:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 167:

GGCCTGGAAA G                                                        11

(2) INFORMATION FOR SEQ ID NO: 168:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 168:

GGCCTGGAAA                                                          10

-continued (2) INFORMATION FOR SEQ ID NO: 169:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 169:

GCCTGGAAAG CTGAGATGGA GGGCGGCATG GCGGGCACAG GCTGGGC           47

(2) INFORMATION FOR SEQ ID NO: 170:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 170:

GCCTGGAAAG CTGAGATGGA GGGCGGCATG GCGGGCACAG GCTGGG            46

(2) INFORMATION FOR SEQ ID NO: 171:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 171:

GCCTGGAAAG CTGAGATGGA GGGCGGCATG GCGGGCACAG GCTGG             45

(2) INFORMATION FOR SEQ ID NO: 172:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 172:

GCCTGGAAAG CTGAGATGGA GGGCGGCATG GCGGGCACAG GCTG              44

(2) INFORMATION FOR SEQ ID NO: 173:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 173:

GCCTGGAAAG CTGAGATGGA GGGCGGCATG GCGGGCACAG GCT               43

(2) INFORMATION FOR SEQ ID NO: 174:

(i) SEQUENCE CHARACTERISTICS:
        (A) LENGTH: 42 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 174:

GCCTGGAAAG CTGAGATGGA GGGCGGCATG GCGGGCACAG GC            42

(2) INFORMATION FOR SEQ ID NO: 175:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 175:

GCCTGGAAAG CTGAGATGGA GGGCGGCATG GCGGGCACAG G             41

(2) INFORMATION FOR SEQ ID NO: 176:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 176:

GCCTGGAAAG CTGAGATGGA GGGCGGCATG GCGGGCACAG               40

(2) INFORMATION FOR SEQ ID NO: 177:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 177:

GCCTGGAAAG CTGAGATGGA GGGCGGCATG GCGGGCACA                39

(2) INFORMATION FOR SEQ ID NO: 178:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 178:

GCCTGGAAAG CTGAGATGGA GGGCGGCATG GCGGGCAC                 38

(2) INFORMATION FOR SEQ ID NO: 179:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 179:

GCCTGGAAAG CTGAGATGGA GGGCGGCATG GCGGGCA                                    37

(2) INFORMATION FOR SEQ ID NO: 180:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 180:

GCCTGGAAAG CTGAGATGGA GGGCGGCATG GCGGGC                                     36

(2) INFORMATION FOR SEQ ID NO: 181:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 181:

GCCTGGAAAG CTGAGATGGA GGGCGGCATG GCGGG                                      35

(2) INFORMATION FOR SEQ ID NO: 182:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 182:

GCCTGGAAAG CTGAGATGGA GGGCGGCATG GCGG                                       34

(2) INFORMATION FOR SEQ ID NO: 183:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 183:

GCCTGGAAAG CTGAGATGGA GGGCGGCATG GCG                                        33

(2) INFORMATION FOR SEQ ID NO: 184:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 184:

-continued

GCCTGGAAAG CTGAGATGGA GGGCGGCATG GC                32

(2) INFORMATION FOR SEQ ID NO: 185:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 185:

GCCTGGAAAG CTGAGATGGA GGGCGGCATG G                 31

(2) INFORMATION FOR SEQ ID NO: 186:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 186:

GCCTGGAAAG CTGAGATGGA GGGCGGCATG                   30

(2) INFORMATION FOR SEQ ID NO: 187:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 187:

GCCTGGAAAG CTGAGATGGA GGGCGGCAT                    29

(2) INFORMATION FOR SEQ ID NO: 188:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 188:

GCCTGGAAAG CTGAGATGGA GGGCGGCA                     28

(2) INFORMATION FOR SEQ ID NO: 189:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 189:

GCCTGGAAAG CTGAGATGGA GGGCGGC                      27

(2) INFORMATION FOR SEQ ID NO: 190:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 190:

GCCTGGAAAG CTGAGATGGA GGGCGG                                            26

(2) INFORMATION FOR SEQ ID NO: 191:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 191:

GCCTGGAAAG CTGAGATGGA GGGCG                                             25

(2) INFORMATION FOR SEQ ID NO: 192:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 192:

GCCTGGAAAG CTGAGATGGA GGGC                                              24

(2) INFORMATION FOR SEQ ID NO: 193:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 193:

GCCTGGAAAG CTGAGATGGA GGG                                               23

(2) INFORMATION FOR SEQ ID NO: 194:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 194:

GCCTGGAAAG CTGAGATGGA GG                                                22

(2) INFORMATION FOR SEQ ID NO: 195:

(i) SEQUENCE CHARACTERISTICS:
        (A) LENGTH: 21 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO: 195:

GCCTGGAAAG CTGAGATGGA G                                              21

(2) INFORMATION FOR SEQ ID NO: 196:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 196:

GCCTGGAAAG CTGAGATGGA                                                20

(2) INFORMATION FOR SEQ ID NO: 197:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 197:

GCCTGGAAAG CTGAGATGG                                                 19

(2) INFORMATION FOR SEQ ID NO: 198:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 198:

GCCTGGAAAG CTGAGATG                                                  18

(2) INFORMATION FOR SEQ ID NO: 199:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 199:

GCCTGGAAAG CTGAGAT                                                   17

(2) INFORMATION FOR SEQ ID NO: 200:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 200:

GCCTGGAAAG CTGAGA                                                    16

(2) INFORMATION FOR SEQ ID NO: 201:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 201:

GCCTGGAAAG CTGAG                                                     15

(2) INFORMATION FOR SEQ ID NO: 202:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 202:

GCCTGGAAAG CTGA                                                      14

(2) INFORMATION FOR SEQ ID NO: 203:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 203:

GCCTGGAAAG CTG                                                       13

(2) INFORMATION FOR SEQ ID NO: 204:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 204:

GCCTGGAAAG CT                                                        12

(2) INFORMATION FOR SEQ ID NO: 205:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 205:

GCCTGGAAAG C                                                         11

(2) INFORMATION FOR SEQ ID NO: 206:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 206:

```
GCCTGGAAAG                                                          10
```

(2) INFORMATION FOR SEQ ID NO: 207:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 207:

```
CCTGGAAAGC TGAGATGGAG GGCGGCATGG CGGGCACAGG CTGGGC                  46
```

(2) INFORMATION FOR SEQ ID NO: 208:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 208:

```
CCTGGAAAGC TGAGATGGAG GGCGGCATGG CGGGCACAGG CTGGG                   45
```

(2) INFORMATION FOR SEQ ID NO: 209:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 209:

```
CCTGGAAAGC TGAGATGGAG GGCGGCATGG CGGGCACAGG CTGG                    44
```

(2) INFORMATION FOR SEQ ID NO: 210:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 210:

```
CCTGGAAAGC TGAGATGGAG GGCGGCATGG CGGGCACAGG CTG                     43
```

(2) INFORMATION FOR SEQ ID NO: 211:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 211:

CCTGGAAAGC TGAGATGGAG GGCGGCATGG CGGGCACAGG CT                              42

(2) INFORMATION FOR SEQ ID NO: 212:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 212:

CCTGGAAAGC TGAGATGGAG GGCGGCATGG CGGGCACAGG C                               41

(2) INFORMATION FOR SEQ ID NO: 213:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 213:

CCTGGAAAGC TGAGATGGAG GGCGGCATGG CGGGCACAGG                                 40

(2) INFORMATION FOR SEQ ID NO: 214:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 214:

CCTGGAAAGC TGAGATGGAG GGCGGCATGG CGGGCACAG                                  39

(2) INFORMATION FOR SEQ ID NO: 215:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 215:

CCTGGAAAGC TGAGATGGAG GGCGGCATGG CGGGCACA                                   38

(2) INFORMATION FOR SEQ ID NO: 216:

(i) SEQUENCE CHARACTERISTICS:
         (A) LENGTH: 37 base pairs
         (B) TYPE: nucleic acid
         (C) STRANDEDNESS: single -continued (D) TOPOLOGY: linear (ii) MOLECULE TYPE: DNA (genomic)

(xi) SEQUENCE DESCRIPTION: SEQ ID NO: 216:

CCTGGAAAGC TGAGATGGAG GGCGGCATGG CGGGCAC                                37

(2) INFORMATION FOR SEQ ID NO: 217:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 217:

CCTGGAAAGC TGAGATGGAG GGCGGCATGG CGGGCA                                 36

(2) INFORMATION FOR SEQ ID NO: 218:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 218:

CCTGGAAAGC TGAGATGGAG GGCGGCATGG CGGGC                                  35

(2) INFORMATION FOR SEQ ID NO: 219:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 219:

CCTGGAAAGC TGAGATGGAG GGCGGCATGG CGGG                                   34

(2) INFORMATION FOR SEQ ID NO: 220:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 220:

CCTGGAAAGC TGAGATGGAG GGCGGCATGG CGG                                    33

(2) INFORMATION FOR SEQ ID NO: 221:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 221:

CCTGGAAAGC TGAGATGGAG GGCGGCATGG CG                                         32

(2) INFORMATION FOR SEQ ID NO: 222:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 222:

CCTGGAAAGC TGAGATGGAG GGCGGCATGG C                                          31

(2) INFORMATION FOR SEQ ID NO: 223:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 223:

CCTGGAAAGC TGAGATGGAG GGCGGCATGG                                            30

(2) INFORMATION FOR SEQ ID NO: 224:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 224:

CCTGGAAAGC TGAGATGGAG GGCGGCATG                                             29

(2) INFORMATION FOR SEQ ID NO: 225:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 225:

CCTGGAAAGC TGAGATGGAG GGCGGCAT                                              28

(2) INFORMATION FOR SEQ ID NO: 226:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 226:

CCTGGAAAGC TGAGATGGAG GGCGGCA                                               27

-continued (2) INFORMATION FOR SEQ ID NO: 227:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 227:

CCTGGAAAGC TGAGATGGAG GGCGGC                          26

(2) INFORMATION FOR SEQ ID NO: 228:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 228:

CCTGGAAAGC TGAGATGGAG GGCGG                           25

(2) INFORMATION FOR SEQ ID NO: 229:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 229:

CCTGGAAAGC TGAGATGGAG GGCG                            24

(2) INFORMATION FOR SEQ ID NO: 230:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 230:

CCTGGAAAGC TGAGATGGAG GGC                             23

(2) INFORMATION FOR SEQ ID NO: 231:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 231:

CCTGGAAAGC TGAGATGGAG GG                              22

(2) INFORMATION FOR SEQ ID NO: 232:

(i) SEQUENCE CHARACTERISTICS:

(A) LENGTH: 21 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 232:

CCTGGAAAGC TGAGATGGAG G                                              21

(2) INFORMATION FOR SEQ ID NO: 233:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 233:

CCTGGAAAGC TGAGATGGAG                                                20

(2) INFORMATION FOR SEQ ID NO: 234:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 234:

CCTGGAAAGC TGAGATGGA                                                 19

(2) INFORMATION FOR SEQ ID NO: 235:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 235:

CCTGGAAAGC TGAGATGG                                                  18

(2) INFORMATION FOR SEQ ID NO: 236:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 236:

CCTGGAAAGC TGAGATG                                                   17

(2) INFORMATION FOR SEQ ID NO: 237:

(i) SEQUENCE CHARACTERISTICS:
       (A) LENGTH: 16 base pairs
       (B) TYPE: nucleic acid
       (C) STRANDEDNESS: single
       (D) TOPOLOGY: linear

```
      (ii) MOLECULE TYPE: DNA (genomic)

(xi) SEQUENCE DESCRIPTION: SEQ ID NO: 237:

CCTGGAAAGC TGAGAT                                                 16

(2) INFORMATION FOR SEQ ID NO: 238:

(i) SEQUENCE CHARACTERISTICS:
           (A) LENGTH: 15 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 238:

CCTGGAAAGC TGAGA                                                  15

(2) INFORMATION FOR SEQ ID NO: 239:

(i) SEQUENCE CHARACTERISTICS:
           (A) LENGTH: 14 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 239:

CCTGGAAAGC TGAG                                                   14

(2) INFORMATION FOR SEQ ID NO: 240:

(i) SEQUENCE CHARACTERISTICS:
           (A) LENGTH: 13 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 240:

CCTGGAAAGC TGA                                                    13

(2) INFORMATION FOR SEQ ID NO: 241:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 241:

CCTGGAAAGC TG                                                     12

(2) INFORMATION FOR SEQ ID NO: 242:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 242:
```

```
CCTGGAAAGC T                                                    11

(2) INFORMATION FOR SEQ ID NO: 243:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 243:

CCTGGAAAGC                                                      10

(2) INFORMATION FOR SEQ ID NO: 244:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 244:

CTGGAAAGCT GAGATGGAGG GCGGCATGGC GGGCACAGGC TGGGC               45

(2) INFORMATION FOR SEQ ID NO: 245:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 245:

CTGGAAAGCT GAGATGGAGG GCGGCATGGC GGGCACAGGC TGGG                44

(2) INFORMATION FOR SEQ ID NO: 246:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 246:

CTGGAAAGCT GAGATGGAGG GCGGCATGGC GGGCACAGGC TGG                 43

(2) INFORMATION FOR SEQ ID NO: 247:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 247:

CTGGAAAGCT GAGATGGAGG GCGGCATGGC GGGCACAGGC TG                  42
```

(2) INFORMATION FOR SEQ ID NO: 248:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 248:

CTGGAAAGCT GAGATGGAGG GCGGCATGGC GGGCACAGGC T          41

(2) INFORMATION FOR SEQ ID NO: 249:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 249:

CTGGAAAGCT GAGATGGAGG GCGGCATGGC GGGCACAGGC            40

(2) INFORMATION FOR SEQ ID NO: 250:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 250:

CTGGAAAGCT GAGATGGAGG GCGGCATGGC GGGCACAGG             39

(2) INFORMATION FOR SEQ ID NO: 251:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 251:

CTGGAAAGCT GAGATGGAGG GCGGCATGGC GGGCACAG              38

(2) INFORMATION FOR SEQ ID NO: 252:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 252:

CTGGAAAGCT GAGATGGAGG GCGGCATGGC GGGCACA               37

(2) INFORMATION FOR SEQ ID NO: 253:

(i) SEQUENCE CHARACTERISTICS:
        (A) LENGTH: 36 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 253:

CTGGAAAGCT GAGATGGAGG GCGGCATGGC GGGCAC                                 36

(2) INFORMATION FOR SEQ ID NO: 254:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 254:

CTGGAAAGCT GAGATGGAGG GCGGCATGGC GGGCA                                  35

(2) INFORMATION FOR SEQ ID NO: 255:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 255:

CTGGAAAGCT GAGATGGAGG GCGGCATGGC GGGC                                   34

(2) INFORMATION FOR SEQ ID NO: 256:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 256:

CTGGAAAGCT GAGATGGAGG GCGGCATGGC GGG                                    33

(2) INFORMATION FOR SEQ ID NO: 257:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 257:

CTGGAAAGCT GAGATGGAGG GCGGCATGGC GG                                     32

(2) INFORMATION FOR SEQ ID NO: 258:

(i) SEQUENCE CHARACTERISTICS:
            (A) LENGTH: 31 base pairs
            (B) TYPE: nucleic acid
            (C) STRANDEDNESS: single
            (D) TOPOLOGY: linear
```

(ii) MOLECULE TYPE: DNA (genomic)

(xi) SEQUENCE DESCRIPTION: SEQ ID NO: 258:

CTGGAAAGCT GAGATGGAGG GCGGCATGGC G                                               31

(2) INFORMATION FOR SEQ ID NO: 259:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 259:

CTGGAAAGCT GAGATGGAGG GCGGCATGGC                                                 30

(2) INFORMATION FOR SEQ ID NO: 260:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 260:

CTGGAAAGCT GAGATGGAGG GCGGCATGG                                                  29

(2) INFORMATION FOR SEQ ID NO: 261:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 261:

CTGGAAAGCT GAGATGGAGG GCGGCATG                                                   28

(2) INFORMATION FOR SEQ ID NO: 262:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 262:

CTGGAAAGCT GAGATGGAGG GCGGCAT                                                    27

(2) INFORMATION FOR SEQ ID NO: 263:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 263:

| CTGGAAAGCT GAGATGGAGG GCGGCA | 26 |

(2) INFORMATION FOR SEQ ID NO: 264:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 264:

| CTGGAAAGCT GAGATGGAGG GCGGC | 25 |

(2) INFORMATION FOR SEQ ID NO: 265:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 265:

| CTGGAAAGCT GAGATGGAGG GCGG | 24 |

(2) INFORMATION FOR SEQ ID NO: 266:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 266:

| CTGGAAAGCT GAGATGGAGG GCG | 23 |

(2) INFORMATION FOR SEQ ID NO: 267:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 267:

| CTGGAAAGCT GAGATGGAGG GC | 22 |

(2) INFORMATION FOR SEQ ID NO: 268:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 268:

| CTGGAAAGCT GAGATGGAGG G | 21 |

(2) INFORMATION FOR SEQ ID NO: 269:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 269:

CTGGAAAGCT GAGATGGAGG                                                   20

(2) INFORMATION FOR SEQ ID NO: 270:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 270:

CTGGAAAGCT GAGATGGAG                                                    19

(2) INFORMATION FOR SEQ ID NO: 271:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 271:

CTGGAAAGCT GAGATGGA                                                     18

(2) INFORMATION FOR SEQ ID NO: 272:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 272:

CTGGAAAGCT GAGATGG                                                      17

(2) INFORMATION FOR SEQ ID NO: 273:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 273:

CTGGAAAGCT GAGATG                                                       16

(2) INFORMATION FOR SEQ ID NO: 274:

(i) SEQUENCE CHARACTERISTICS:
        (A) LENGTH: 15 base pairs
        (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO: 274:

CTGGAAAGCT GAGAT                                                15

(2) INFORMATION FOR SEQ ID NO: 275:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 275:

CTGGAAAGCT GAGA                                                 14

(2) INFORMATION FOR SEQ ID NO: 276:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 276:

CTGGAAAGCT GAG                                                  13

(2) INFORMATION FOR SEQ ID NO: 277:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 277:

CTGGAAAGCT GA                                                   12

(2) INFORMATION FOR SEQ ID NO: 278:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 278:

CTGGAAAGCT G                                                    11

(2) INFORMATION FOR SEQ ID NO: 279:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO: 279:

CTGGAAAGCT                                                                                    10

(2) INFORMATION FOR SEQ ID NO: 280:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 280:

TGGAAAGCTG AGATGGAGGG CGGCATGGCG GGCACAGGCT GGGC                                               44

(2) INFORMATION FOR SEQ ID NO: 281:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 281:

TGGAAAGCTG AGATGGAGGG CGGCATGGCG GGCACAGGCT GGG                                                43

(2) INFORMATION FOR SEQ ID NO: 282:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 282:

TGGAAAGCTG AGATGGAGGG CGGCATGGCG GGCACAGGCT GG                                                 42

(2) INFORMATION FOR SEQ ID NO: 283:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 283:

TGGAAAGCTG AGATGGAGGG CGGCATGGCG GGCACAGGCT G                                                  41

(2) INFORMATION FOR SEQ ID NO: 284:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 284:

TGGAAAGCTG AGATGGAGGG CGGCATGGCG GGCACAGGCT                                                    40

(2) INFORMATION FOR SEQ ID NO: 285:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 285:

TGGAAAGCTG AGATGGAGGG CGGCATGGCG GGCACAGGC        39

(2) INFORMATION FOR SEQ ID NO: 286:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 286:

TGGAAAGCTG AGATGGAGGG CGGCATGGCG GGCACAGG        38

(2) INFORMATION FOR SEQ ID NO: 287:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 287:

TGGAAAGCTG AGATGGAGGG CGGCATGGCG GGCACAG        37

(2) INFORMATION FOR SEQ ID NO: 288:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 288:

TGGAAAGCTG AGATGGAGGG CGGCATGGCG GGCACA        36

(2) INFORMATION FOR SEQ ID NO: 289:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 289:

TGGAAAGCTG AGATGGAGGG CGGCATGGCG GGCAC        35

(2) INFORMATION FOR SEQ ID NO: 290:

```
    (i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 290:

TGGAAAGCTG AGATGGAGGG CGGCATGGCG GGCA                                34

(2) INFORMATION FOR SEQ ID NO: 291:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 291:

TGGAAAGCTG AGATGGAGGG CGGCATGGCG GGC                                 33

(2) INFORMATION FOR SEQ ID NO: 292:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 292:

TGGAAAGCTG AGATGGAGGG CGGCATGGCG GG                                  32

(2) INFORMATION FOR SEQ ID NO: 293:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 293:

TGGAAAGCTG AGATGGAGGG CGGCATGGCG G                                   31

(2) INFORMATION FOR SEQ ID NO: 294:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 294:

TGGAAAGCTG AGATGGAGGG CGGCATGGCG                                     30

(2) INFORMATION FOR SEQ ID NO: 295:

(i) SEQUENCE CHARACTERISTICS:
        (A) LENGTH: 29 base pairs
        (B) TYPE: nucleic acid
        (C) STRANDEDNESS: single
```

-continued (D) TOPOLOGY: linear (ii) MOLECULE TYPE: DNA (genomic)

(xi) SEQUENCE DESCRIPTION: SEQ ID NO: 295:

TGGAAAGCTG AGATGGAGGG CGGCATGGC                                          29

(2) INFORMATION FOR SEQ ID NO: 296:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 296:

TGGAAAGCTG AGATGGAGGG CGGCATGG                                           28

(2) INFORMATION FOR SEQ ID NO: 297:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 297:

TGGAAAGCTG AGATGGAGGG CGGCATG                                            27

(2) INFORMATION FOR SEQ ID NO: 298:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 298:

TGGAAAGCTG AGATGGAGGG CGGCAT                                             26

(2) INFORMATION FOR SEQ ID NO: 299:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 299:

TGGAAAGCTG AGATGGAGGG CGGCA                                              25

(2) INFORMATION FOR SEQ ID NO: 300:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 300:

TGGAAAGCTG AGATGGAGGG CGGC                                           24

(2) INFORMATION FOR SEQ ID NO: 301:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 301:

TGGAAAGCTG AGATGGAGGG CGG                                            23

(2) INFORMATION FOR SEQ ID NO: 302:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 302:

TGGAAAGCTG AGATGGAGGG CG                                             22

(2) INFORMATION FOR SEQ ID NO: 303:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 303:

TGGAAAGCTG AGATGGAGGG C                                              21

(2) INFORMATION FOR SEQ ID NO: 304:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 304:

TGGAAAGCTG AGATGGAGGG                                                20

(2) INFORMATION FOR SEQ ID NO: 305:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 305:

TGGAAAGCTG AGATGGAGG                                                 19

(2) INFORMATION FOR SEQ ID NO: 306:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 306:

TGGAAAGCTG AGATGGAG                                                 18

(2) INFORMATION FOR SEQ ID NO: 307:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 307:

TGGAAAGCTG AGATGGA                                                  17

(2) INFORMATION FOR SEQ ID NO: 308:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 308:

TGGAAAGCTG AGATGG                                                   16

(2) INFORMATION FOR SEQ ID NO: 309:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 309:

TGGAAAGCTG AGATG                                                    15

(2) INFORMATION FOR SEQ ID NO: 310:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 310:

TGGAAAGCTG AGAT                                                     14

(2) INFORMATION FOR SEQ ID NO: 311:

(i) SEQUENCE CHARACTERISTICS:

(A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 311:

TGGAAAGCTG AGA                                              13

(2) INFORMATION FOR SEQ ID NO: 312:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 312:

TGGAAAGCTG AG                                               12

(2) INFORMATION FOR SEQ ID NO: 313:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 313:

TGGAAAGCTG A                                                11

(2) INFORMATION FOR SEQ ID NO: 314:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 314:

TGGAAAGCTG                                                  10

(2) INFORMATION FOR SEQ ID NO: 315:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 315:

GGAAAGCTGA GATGGAGGGC GGCATGGCGG GCACAGGCTG GGC              43

(2) INFORMATION FOR SEQ ID NO: 316:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 316:

GGAAAGCTGA GATGGAGGGC GGCATGGCGG GCACAGGCTG GG                              42

(2) INFORMATION FOR SEQ ID NO: 317:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 317:

GGAAAGCTGA GATGGAGGGC GGCATGGCGG GCACAGGCTG G                               41

(2) INFORMATION FOR SEQ ID NO: 318:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 318:

GGAAAGCTGA GATGGAGGGC GGCATGGCGG GCACAGGCTG                                 40

(2) INFORMATION FOR SEQ ID NO: 319:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 319:

GGAAAGCTGA GATGGAGGGC GGCATGGCGG GCACAGGCT                                  39

(2) INFORMATION FOR SEQ ID NO: 320:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 320:

GGAAAGCTGA GATGGAGGGC GGCATGGCGG GCACAGGC                                   38

(2) INFORMATION FOR SEQ ID NO: 321:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 321:

-continued

GGAAAGCTGA GATGGAGGGC GGCATGGCGG GCACAGG                                37

(2) INFORMATION FOR SEQ ID NO: 322:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 322:

GGAAAGCTGA GATGGAGGGC GGCATGGCGG GCACAG                                 36

(2) INFORMATION FOR SEQ ID NO: 323:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 323:

GGAAAGCTGA GATGGAGGGC GGCATGGCGG GCACA                                  35

(2) INFORMATION FOR SEQ ID NO: 324:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 324:

GGAAAGCTGA GATGGAGGGC GGCATGGCGG GCAC                                   34

(2) INFORMATION FOR SEQ ID NO: 325:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 325:

GGAAAGCTGA GATGGAGGGC GGCATGGCGG GCA                                    33

(2) INFORMATION FOR SEQ ID NO: 326:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 326:

GGAAAGCTGA GATGGAGGGC GGCATGGCGG GC                                     32

(2) INFORMATION FOR SEQ ID NO: 327:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 327:

GGAAAGCTGA GATGGAGGGC GGCATGGCGG G                          31

(2) INFORMATION FOR SEQ ID NO: 328:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 328:

GGAAAGCTGA GATGGAGGGC GGCATGGCGG                            30

(2) INFORMATION FOR SEQ ID NO: 329:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 329:

GGAAAGCTGA GATGGAGGGC GGCATGGCG                             29

(2) INFORMATION FOR SEQ ID NO: 330:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 330:

GGAAAGCTGA GATGGAGGGC GGCATGGC                              28

(2) INFORMATION FOR SEQ ID NO: 331:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 331:

GGAAAGCTGA GATGGAGGGC GGCATGG                               27

(2) INFORMATION FOR SEQ ID NO: 332:

(i) SEQUENCE CHARACTERISTICS:
        (A) LENGTH: 26 base pairs

-continued

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 332:

GGAAAGCTGA GATGGAGGGC GGCATG                                              26

(2) INFORMATION FOR SEQ ID NO: 333:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 333:

GGAAAGCTGA GATGGAGGGC GGCAT                                               25

(2) INFORMATION FOR SEQ ID NO: 334:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 334:

GGAAAGCTGA GATGGAGGGC GGCA                                                24

(2) INFORMATION FOR SEQ ID NO: 335:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 335:

GGAAAGCTGA GATGGAGGGC GGC                                                 23

(2) INFORMATION FOR SEQ ID NO: 336:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 336:

GGAAAGCTGA GATGGAGGGC GG                                                  22

(2) INFORMATION FOR SEQ ID NO: 337:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

-continued (ii) MOLECULE TYPE: DNA (genomic)

(xi) SEQUENCE DESCRIPTION: SEQ ID NO: 337:

GGAAAGCTGA GATGGAGGGC G                                              21

(2) INFORMATION FOR SEQ ID NO: 338:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 338:

GGAAAGCTGA GATGGAGGGC                                                20

(2) INFORMATION FOR SEQ ID NO: 339:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 339:

GGAAAGCTGA GATGGAGGG                                                 19

(2) INFORMATION FOR SEQ ID NO: 340:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 340:

GGAAAGCTGA GATGGAGG                                                  18

(2) INFORMATION FOR SEQ ID NO: 341:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 341:

GGAAAGCTGA GATGGAG                                                   17

(2) INFORMATION FOR SEQ ID NO: 342:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 342:

```
GGAAAGCTGA GATGGA                                                  16

(2) INFORMATION FOR SEQ ID NO: 343:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 343:

GGAAAGCTGA GATGG                                                   15

(2) INFORMATION FOR SEQ ID NO: 344:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 344:

GGAAAGCTGA GATG                                                    14

(2) INFORMATION FOR SEQ ID NO: 345:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 345:

GGAAAGCTGA GAT                                                     13

(2) INFORMATION FOR SEQ ID NO: 346:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 346:

GGAAAGCTGA GA                                                      12

(2) INFORMATION FOR SEQ ID NO: 347:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 347:

GGAAAGCTGA G                                                       11

(2) INFORMATION FOR SEQ ID NO: 348:
```

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 348:

GGAAAGCTGA                                                          10

(2) INFORMATION FOR SEQ ID NO: 349:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 349:

GAAAGCTGAG ATGGAGGGCG GCATGGCGGG CACAGGCTGG GC                      42

(2) INFORMATION FOR SEQ ID NO: 350:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 350:

GAAAGCTGAG ATGGAGGGCG GCATGGCGGG CACAGGCTGG G                       41

(2) INFORMATION FOR SEQ ID NO: 351:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 351:

GAAAGCTGAG ATGGAGGGCG GCATGGCGGG CACAGGCTGG                         40

(2) INFORMATION FOR SEQ ID NO: 352:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 352:

GAAAGCTGAG ATGGAGGGCG GCATGGCGGG CACAGGCTG                          39

(2) INFORMATION FOR SEQ ID NO: 353:

(i) SEQUENCE CHARACTERISTICS:
        (A) LENGTH: 38 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO: 353:

GAAAGCTGAG ATGGAGGGCG GCATGGCGGG CACAGGCT                                38

(2) INFORMATION FOR SEQ ID NO: 354:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 354:

GAAAGCTGAG ATGGAGGGCG GCATGGCGGG CACAGGC                                 37

(2) INFORMATION FOR SEQ ID NO: 355:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 355:

GAAAGCTGAG ATGGAGGGCG GCATGGCGGG CACAGG                                  36

(2) INFORMATION FOR SEQ ID NO: 356:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 356:

GAAAGCTGAG ATGGAGGGCG GCATGGCGGG CACAG                                   35

(2) INFORMATION FOR SEQ ID NO: 357:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 357:

GAAAGCTGAG ATGGAGGGCG GCATGGCGGG CACA                                    34

(2) INFORMATION FOR SEQ ID NO: 358:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 358:

GAAAGCTGAG ATGGAGGGCG GCATGGCGGG CAC                                    33

(2) INFORMATION FOR SEQ ID NO: 359:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 359:

GAAAGCTGAG ATGGAGGGCG GCATGGCGGG CA                                     32

(2) INFORMATION FOR SEQ ID NO: 360:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 360:

GAAAGCTGAG ATGGAGGGCG GCATGGCGGG C                                      31

(2) INFORMATION FOR SEQ ID NO: 361:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 361:

GAAAGCTGAG ATGGAGGGCG GCATGGCGGG                                        30

(2) INFORMATION FOR SEQ ID NO: 362:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 362:

GAAAGCTGAG ATGGAGGGCG GCATGGCGG                                         29

(2) INFORMATION FOR SEQ ID NO: 363:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 363:

GAAAGCTGAG ATGGAGGGCG GCATGGCG                                          28

(2) INFORMATION FOR SEQ ID NO: 364:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 364:

GAAAGCTGAG ATGGAGGGCG GCATGGC                                          27

(2) INFORMATION FOR SEQ ID NO: 365:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 365:

GAAAGCTGAG ATGGAGGGCG GCATGG                                           26

(2) INFORMATION FOR SEQ ID NO: 366:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 366:

GAAAGCTGAG ATGGAGGGCG GCATG                                            25

(2) INFORMATION FOR SEQ ID NO: 367:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 367:

GAAAGCTGAG ATGGAGGGCG GCAT                                             24

(2) INFORMATION FOR SEQ ID NO: 368:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 368:

GAAAGCTGAG ATGGAGGGCG GCA                                              23

(2) INFORMATION FOR SEQ ID NO: 369:

```
      (i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 369:

GAAAGCTGAG ATGGAGGGCG GC                                              22

(2) INFORMATION FOR SEQ ID NO: 370:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 370:

GAAAGCTGAG ATGGAGGGCG G                                               21

(2) INFORMATION FOR SEQ ID NO: 371:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 371:

GAAAGCTGAG ATGGAGGGCG                                                 20

(2) INFORMATION FOR SEQ ID NO: 372:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 372:

GAAAGCTGAG ATGGAGGGC                                                  19

(2) INFORMATION FOR SEQ ID NO: 373:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 373:

GAAAGCTGAG ATGGAGGG                                                   18

(2) INFORMATION FOR SEQ ID NO: 374:

(i) SEQUENCE CHARACTERISTICS:
          (A) LENGTH: 17 base pairs
          (B) TYPE: nucleic acid
          (C) STRANDEDNESS: single
```

(D) TOPOLOGY: linear (ii) MOLECULE TYPE: DNA (genomic)

(xi) SEQUENCE DESCRIPTION: SEQ ID NO: 374:

GAAAGCTGAG ATGGAGG                                                    17

(2) INFORMATION FOR SEQ ID NO: 375:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 375:

GAAAGCTGAG ATGGAG                                                     16

(2) INFORMATION FOR SEQ ID NO: 376:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 376:

GAAAGCTGAG ATGGA                                                      15

(2) INFORMATION FOR SEQ ID NO: 377:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 377:

GAAAGCTGAG ATGG                                                       14

(2) INFORMATION FOR SEQ ID NO: 378:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 378:

GAAAGCTGAG ATG                                                        13

(2) INFORMATION FOR SEQ ID NO: 379:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 379:

GAAAGCTGAG AT                                                   12

(2) INFORMATION FOR SEQ ID NO: 380:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 380:

GAAAGCTGAG A                                                    11

(2) INFORMATION FOR SEQ ID NO: 381:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 381:

GAAAGCTGAG                                                      10

(2) INFORMATION FOR SEQ ID NO: 382:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 382:

AAAGCTGAGA TGGAGGGCGG CATGGCGGGC ACAGGCTGGG C                   41

(2) INFORMATION FOR SEQ ID NO: 383:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 383:

AAAGCTGAGA TGGAGGGCGG CATGGCGGGC ACAGGCTGGG                     40

(2) INFORMATION FOR SEQ ID NO: 384:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 384:

AAAGCTGAGA TGGAGGGCGG CATGGCGGGC ACAGGCTGG                      39

-continued (2) INFORMATION FOR SEQ ID NO: 385:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 385:

AAAGCTGAGA TGGAGGGCGG CATGGCGGGC ACAGGCTG                    38

(2) INFORMATION FOR SEQ ID NO: 386:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 386:

AAAGCTGAGA TGGAGGGCGG CATGGCGGGC ACAGGCT                     37

(2) INFORMATION FOR SEQ ID NO: 387:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 387:

AAAGCTGAGA TGGAGGGCGG CATGGCGGGC ACAGGC                      36

(2) INFORMATION FOR SEQ ID NO: 388:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 388:

AAAGCTGAGA TGGAGGGCGG CATGGCGGGC ACAGG                       35

(2) INFORMATION FOR SEQ ID NO: 389:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 389:

AAAGCTGAGA TGGAGGGCGG CATGGCGGGC ACAG                        34

(2) INFORMATION FOR SEQ ID NO: 390:

(i) SEQUENCE CHARACTERISTICS:

(A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 390:

AAAGCTGAGA TGGAGGGCGG CATGGCGGGC ACA                                    33

(2) INFORMATION FOR SEQ ID NO: 391:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 391:

AAAGCTGAGA TGGAGGGCGG CATGGCGGGC AC                                     32

(2) INFORMATION FOR SEQ ID NO: 392:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 392:

AAAGCTGAGA TGGAGGGCGG CATGGCGGGC A                                      31

(2) INFORMATION FOR SEQ ID NO: 393:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 393:

AAAGCTGAGA TGGAGGGCGG CATGGCGGGC                                        30

(2) INFORMATION FOR SEQ ID NO: 394:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 394:

AAAGCTGAGA TGGAGGGCGG CATGGCGGG                                         29

(2) INFORMATION FOR SEQ ID NO: 395:

(i) SEQUENCE CHARACTERISTICS:
            (A) LENGTH: 28 base pairs
            (B) TYPE: nucleic acid
            (C) STRANDEDNESS: single
            (D) TOPOLOGY: linear

```
        (ii) MOLECULE TYPE: DNA (genomic)

(xi) SEQUENCE DESCRIPTION: SEQ ID NO: 395:

AAAGCTGAGA TGGAGGGCGG CATGGCGG                                          28

(2) INFORMATION FOR SEQ ID NO: 396:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 396:

AAAGCTGAGA TGGAGGGCGG CATGGCG                                           27

(2) INFORMATION FOR SEQ ID NO: 397:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 397:

AAAGCTGAGA TGGAGGGCGG CATGGC                                            26

(2) INFORMATION FOR SEQ ID NO: 398:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 398:

AAAGCTGAGA TGGAGGGCGG CATGG                                             25

(2) INFORMATION FOR SEQ ID NO: 399:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 399:

AAAGCTGAGA TGGAGGGCGG CATG                                              24

(2) INFORMATION FOR SEQ ID NO: 400:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 400:
```

```
AAAGCTGAGA TGGAGGGCGG CAT                                            23

(2) INFORMATION FOR SEQ ID NO: 401:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 401:

AAAGCTGAGA TGGAGGGCGG CA                                             22

(2) INFORMATION FOR SEQ ID NO: 402:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 402:

AAAGCTGAGA TGGAGGGCGG C                                              21

(2) INFORMATION FOR SEQ ID NO: 403:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 403:

AAAGCTGAGA TGGAGGGCGG                                                20

(2) INFORMATION FOR SEQ ID NO: 404:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 404:

AAAGCTGAGA TGGAGGGCG                                                 19

(2) INFORMATION FOR SEQ ID NO: 405:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 405:

AAAGCTGAGA TGGAGGGC                                                  18
```

-continued (2) INFORMATION FOR SEQ ID NO: 406:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 406:

AAAGCTGAGA TGGAGGG                                                   17

(2) INFORMATION FOR SEQ ID NO: 407:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 407:

AAAGCTGAGA TGGAGG                                                    16

(2) INFORMATION FOR SEQ ID NO: 408:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 408:

AAAGCTGAGA TGGAG                                                     15

(2) INFORMATION FOR SEQ ID NO: 409:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 409:

AAAGCTGAGA TGGA                                                      14

(2) INFORMATION FOR SEQ ID NO: 410:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 410:

AAAGCTGAGA TGG                                                       13

(2) INFORMATION FOR SEQ ID NO: 411:

(i) SEQUENCE CHARACTERISTICS:
        (A) LENGTH: 12 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 411:

AAAGCTGAGA TG                                                          12

(2) INFORMATION FOR SEQ ID NO: 412:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 412:

AAAGCTGAGA T                                                           11

(2) INFORMATION FOR SEQ ID NO: 413:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 413:

AAAGCTGAGA                                                             10

(2) INFORMATION FOR SEQ ID NO: 414:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 414:

AAGCTGAGAT GGAGGGCGGC ATGGCGGGCA CAGGCTGGGC                             40

(2) INFORMATION FOR SEQ ID NO: 415:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 415:

AAGCTGAGAT GGAGGGCGGC ATGGCGGGCA CAGGCTGGG                              39

(2) INFORMATION FOR SEQ ID NO: 416:

(i) SEQUENCE CHARACTERISTICS:
        (A) LENGTH: 38 base pairs
        (B) TYPE: nucleic acid
        (C) STRANDEDNESS: single
        (D) TOPOLOGY: linear
```

```
    (ii) MOLECULE TYPE: DNA (genomic)

(xi) SEQUENCE DESCRIPTION: SEQ ID NO: 416:

AAGCTGAGAT GGAGGGCGGC ATGGCGGGCA CAGGCTGG                    38

(2) INFORMATION FOR SEQ ID NO: 417:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 417:

AAGCTGAGAT GGAGGGCGGC ATGGCGGGCA CAGGCTG                     37

(2) INFORMATION FOR SEQ ID NO: 418:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 418:

AAGCTGAGAT GGAGGGCGGC ATGGCGGGCA CAGGCT                      36

(2) INFORMATION FOR SEQ ID NO: 419:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 419:

AAGCTGAGAT GGAGGGCGGC ATGGCGGGCA CAGGC                       35

(2) INFORMATION FOR SEQ ID NO: 420:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 420:

AAGCTGAGAT GGAGGGCGGC ATGGCGGGCA CAGG                        34

(2) INFORMATION FOR SEQ ID NO: 421:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 421:
```

```
AAGCTGAGAT GGAGGGCGGC ATGGCGGGCA CAG                                33
```

(2) INFORMATION FOR SEQ ID NO: 422:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 422:

```
AAGCTGAGAT GGAGGGCGGC ATGGCGGGCA CA                                 32
```

(2) INFORMATION FOR SEQ ID NO: 423:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 423:

```
AAGCTGAGAT GGAGGGCGGC ATGGCGGGCA C                                  31
```

(2) INFORMATION FOR SEQ ID NO: 424:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 424:

```
AAGCTGAGAT GGAGGGCGGC ATGGCGGGCA                                    30
```

(2) INFORMATION FOR SEQ ID NO: 425:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 425:

```
AAGCTGAGAT GGAGGGCGGC ATGGCGGGC                                     29
```

(2) INFORMATION FOR SEQ ID NO: 426:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 426:

```
AAGCTGAGAT GGAGGGCGGC ATGGCGGG                                      28
```

(2) INFORMATION FOR SEQ ID NO: 427:

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 427:

AAGCTGAGAT GGAGGGCGGC ATGGCGG                                              27

(2) INFORMATION FOR SEQ ID NO: 428:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 428:

AAGCTGAGAT GGAGGGCGGC ATGGCG                                               26

(2) INFORMATION FOR SEQ ID NO: 429:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 429:

AAGCTGAGAT GGAGGGCGGC ATGGC                                                25

(2) INFORMATION FOR SEQ ID NO: 430:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 430:

AAGCTGAGAT GGAGGGCGGC ATGG                                                 24

(2) INFORMATION FOR SEQ ID NO: 431:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 431:

AAGCTGAGAT GGAGGGCGGC ATG                                                  23

(2) INFORMATION FOR SEQ ID NO: 432:

(i) SEQUENCE CHARACTERISTICS:
        (A) LENGTH: 22 base pairs
        (B) TYPE: nucleic acid
```

(C) STRANDEDNESS: single
        (D) TOPOLOGY: linear (ii) MOLECULE TYPE: DNA (genomic)

(xi) SEQUENCE DESCRIPTION: SEQ ID NO: 432:

AAGCTGAGAT GGAGGGCGGC AT                                            22

(2) INFORMATION FOR SEQ ID NO: 433:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 433:

AAGCTGAGAT GGAGGGCGGC A                                             21

(2) INFORMATION FOR SEQ ID NO: 434:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 434:

AAGCTGAGAT GGAGGGCGGC                                               20

(2) INFORMATION FOR SEQ ID NO: 435:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 435:

AAGCTGAGAT GGAGGGCGG                                                19

(2) INFORMATION FOR SEQ ID NO: 436:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 436:

AAGCTGAGAT GGAGGGCG                                                 18

(2) INFORMATION FOR SEQ ID NO: 437:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 437:

AAGCTGAGAT GGAGGGC 17

(2) INFORMATION FOR SEQ ID NO: 438:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 438:

AAGCTGAGAT GGAGGG 16

(2) INFORMATION FOR SEQ ID NO: 439:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 439:

AAGCTGAGAT GGAGG 15

(2) INFORMATION FOR SEQ ID NO: 440:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 440:

AAGCTGAGAT GGAG 14

(2) INFORMATION FOR SEQ ID NO: 441:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 441:

AAGCTGAGAT GGA 13

(2) INFORMATION FOR SEQ ID NO: 442:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 442:

AAGCTGAGAT GG 12

(2) INFORMATION FOR SEQ ID NO: 443:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 443:

AAGCTGAGAT G                                    11

(2) INFORMATION FOR SEQ ID NO: 444:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 444:

AAGCTGAGAT                                    10

(2) INFORMATION FOR SEQ ID NO: 445:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 445:

AGCTGAGATG GAGGGCGGCA TGGCGGGCAC AGGCTGGGC        39

(2) INFORMATION FOR SEQ ID NO: 446:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 446:

AGCTGAGATG GAGGGCGGCA TGGCGGGCAC AGGCTGGG         38

(2) INFORMATION FOR SEQ ID NO: 447:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 447:

AGCTGAGATG GAGGGCGGCA TGGCGGGCAC AGGCTGG          37

(2) INFORMATION FOR SEQ ID NO: 448:

```
        (i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 448:

AGCTGAGATG GAGGGCGGCA TGGCGGGCAC AGGCTG                                       36

(2) INFORMATION FOR SEQ ID NO: 449:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 449:

AGCTGAGATG GAGGGCGGCA TGGCGGGCAC AGGCT                                        35

(2) INFORMATION FOR SEQ ID NO: 450:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 450:

AGCTGAGATG GAGGGCGGCA TGGCGGGCAC AGGC                                         34

(2) INFORMATION FOR SEQ ID NO: 451:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 451:

AGCTGAGATG GAGGGCGGCA TGGCGGGCAC AGG                                          33

(2) INFORMATION FOR SEQ ID NO: 452:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 452:

AGCTGAGATG GAGGGCGGCA TGGCGGGCAC AG                                           32

(2) INFORMATION FOR SEQ ID NO: 453:

(i) SEQUENCE CHARACTERISTICS:
            (A) LENGTH: 31 base pairs
            (B) TYPE: nucleic acid
            (C) STRANDEDNESS: single
```

(D) TOPOLOGY: linear (ii) MOLECULE TYPE: DNA (genomic)

(xi) SEQUENCE DESCRIPTION: SEQ ID NO: 453:

AGCTGAGATG GAGGGCGGCA TGGCGGGCAC A                                31

(2) INFORMATION FOR SEQ ID NO: 454:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 454:

AGCTGAGATG GAGGGCGGCA TGGCGGGCAC                                  30

(2) INFORMATION FOR SEQ ID NO: 455:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 455:

AGCTGAGATG GAGGGCGGCA TGGCGGGCA                                   29

(2) INFORMATION FOR SEQ ID NO: 456:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 456:

AGCTGAGATG GAGGGCGGCA TGGCGGGC                                    28

(2) INFORMATION FOR SEQ ID NO: 457:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 457:

AGCTGAGATG GAGGGCGGCA TGGCGGG                                     27

(2) INFORMATION FOR SEQ ID NO: 458:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO: 458:

AGCTGAGATG GAGGGCGGCA TGGCGG                                          26

(2) INFORMATION FOR SEQ ID NO: 459:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 459:

AGCTGAGATG GAGGGCGGCA TGGCG                                           25

(2) INFORMATION FOR SEQ ID NO: 460:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 460:

AGCTGAGATG GAGGGCGGCA TGGC                                            24

(2) INFORMATION FOR SEQ ID NO: 461:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 461:

AGCTGAGATG GAGGGCGGCA TGG                                             23

(2) INFORMATION FOR SEQ ID NO: 462:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 462:

AGCTGAGATG GAGGGCGGCA TG                                              22

(2) INFORMATION FOR SEQ ID NO: 463:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 463:

AGCTGAGATG GAGGGCGGCA T                                               21

-continued (2) INFORMATION FOR SEQ ID NO: 464:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 464:

AGCTGAGATG GAGGGCGGCA                                               20

(2) INFORMATION FOR SEQ ID NO: 465:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 465:

AGCTGAGATG GAGGGCGGC                                                19

(2) INFORMATION FOR SEQ ID NO: 466:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 466:

AGCTGAGATG GAGGGCGG                                                 18

(2) INFORMATION FOR SEQ ID NO: 467:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 467:

AGCTGAGATG GAGGGCG                                                  17

(2) INFORMATION FOR SEQ ID NO: 468:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 468:

AGCTGAGATG GAGGGC                                                   16

(2) INFORMATION FOR SEQ ID NO: 469:

(i) SEQUENCE CHARACTERISTICS:

(A) LENGTH: 15 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 469:

AGCTGAGATG GAGGG                                                15

(2) INFORMATION FOR SEQ ID NO: 470:

(i) SEQUENCE CHARACTERISTICS:
           (A) LENGTH: 14 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 470:

AGCTGAGATG GAGG                                                 14

(2) INFORMATION FOR SEQ ID NO: 471:

(i) SEQUENCE CHARACTERISTICS:
           (A) LENGTH: 13 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 471:

AGCTGAGATG GAG                                                  13

(2) INFORMATION FOR SEQ ID NO: 472:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 472:

AGCTGAGATG GA                                                   12

(2) INFORMATION FOR SEQ ID NO: 473:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 473:

AGCTGAGATG G                                                    11

(2) INFORMATION FOR SEQ ID NO: 474:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 474:

AGCTGAGATG                                                                   10

(2) INFORMATION FOR SEQ ID NO: 475:

(i) SEQUENCE CHARACTERISTICS:
              (A) LENGTH: 38 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 475:

GCTGAGATGG AGGGCGGCAT GGCGGGCACA GGCTGGGC                                    38

(2) INFORMATION FOR SEQ ID NO: 476:

(i) SEQUENCE CHARACTERISTICS:
              (A) LENGTH: 37 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 476:

GCTGAGATGG AGGGCGGCAT GGCGGGCACA GGCTGGG                                     37

(2) INFORMATION FOR SEQ ID NO: 477:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 477:

GCTGAGATGG AGGGCGGCAT GGCGGGCACA GGCTGG                                      36

(2) INFORMATION FOR SEQ ID NO: 478:

(i) SEQUENCE CHARACTERISTICS:
              (A) LENGTH: 35 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 478:

GCTGAGATGG AGGGCGGCAT GGCGGGCACA GGCTG                                       35

(2) INFORMATION FOR SEQ ID NO: 479:

(i) SEQUENCE CHARACTERISTICS:
              (A) LENGTH: 34 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 479:

GCTGAGATGG AGGGCGGCAT GGCGGGCACA GGCT                    34

(2) INFORMATION FOR SEQ ID NO: 480:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 480:

GCTGAGATGG AGGGCGGCAT GGCGGGCACA GGC                     33

(2) INFORMATION FOR SEQ ID NO: 481:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 481:

GCTGAGATGG AGGGCGGCAT GGCGGGCACA GG                      32

(2) INFORMATION FOR SEQ ID NO: 482:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 482:

GCTGAGATGG AGGGCGGCAT GGCGGGCACA G                       31

(2) INFORMATION FOR SEQ ID NO: 483:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 483:

GCTGAGATGG AGGGCGGCAT GGCGGGCACA                         30

(2) INFORMATION FOR SEQ ID NO: 484:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 484:

GCTGAGATGG AGGGCGGCAT GGCGGGCAC                          29

-continued (2) INFORMATION FOR SEQ ID NO: 485:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 485:

GCTGAGATGG AGGGCGGCAT GGCGGGCA                                              28

(2) INFORMATION FOR SEQ ID NO: 486:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 486:

GCTGAGATGG AGGGCGGCAT GGCGGGC                                               27

(2) INFORMATION FOR SEQ ID NO: 487:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 487:

GCTGAGATGG AGGGCGGCAT GGCGGG                                                 26

(2) INFORMATION FOR SEQ ID NO: 488:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 488:

GCTGAGATGG AGGGCGGCAT GGCGG                                                   25

(2) INFORMATION FOR SEQ ID NO: 489:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 489:

GCTGAGATGG AGGGCGGCAT GGCG                                                     24

(2) INFORMATION FOR SEQ ID NO: 490:

(i) SEQUENCE CHARACTERISTICS:
        (A) LENGTH: 23 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 490:

GCTGAGATGG AGGGCGGCAT GGC                                              23

(2) INFORMATION FOR SEQ ID NO: 491:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 491:

GCTGAGATGG AGGGCGGCAT GG                                               22

(2) INFORMATION FOR SEQ ID NO: 492:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 492:

GCTGAGATGG AGGGCGGCAT G                                                21

(2) INFORMATION FOR SEQ ID NO: 493:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 493:

GCTGAGATGG AGGGCGGCAT                                                  20

(2) INFORMATION FOR SEQ ID NO: 494:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 494:

GCTGAGATGG AGGGCGGCA                                                   19

(2) INFORMATION FOR SEQ ID NO: 495:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 495:

GCTGAGATGG AGGGCGGC                                                    18

(2) INFORMATION FOR SEQ ID NO: 496:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 496:

GCTGAGATGG AGGGCGG                                                     17

(2) INFORMATION FOR SEQ ID NO: 497:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 497:

GCTGAGATGG AGGGCG                                                      16

(2) INFORMATION FOR SEQ ID NO: 498:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 498:

GCTGAGATGG AGGGC                                                       15

(2) INFORMATION FOR SEQ ID NO: 499:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 499:

GCTGAGATGG AGGG                                                        14

(2) INFORMATION FOR SEQ ID NO: 500:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 500:

| | |
|---|---|
| GCTGAGATGG AGG | 13 |

(2) INFORMATION FOR SEQ ID NO: 501:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 501:

| | |
|---|---|
| GCTGAGATGG AG | 12 |

(2) INFORMATION FOR SEQ ID NO: 502:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 502:

| | |
|---|---|
| GCTGAGATGG A | 11 |

(2) INFORMATION FOR SEQ ID NO: 503:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 503:

| | |
|---|---|
| GCTGAGATGG | 10 |

(2) INFORMATION FOR SEQ ID NO: 504:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 504:

| | |
|---|---|
| CTGAGATGGA GGGCGGCATG GCGGGCACAG GCTGGGC | 37 |

(2) INFORMATION FOR SEQ ID NO: 505:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 505:

| | |
|---|---|
| CTGAGATGGA GGGCGGCATG GCGGGCACAG GCTGGG | 36 |

(2) INFORMATION FOR SEQ ID NO: 506:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 506:

CTGAGATGGA GGGCGGCATG GCGGGCACAG GCTGG                                35

(2) INFORMATION FOR SEQ ID NO: 507:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 507:

CTGAGATGGA GGGCGGCATG GCGGGCACAG GCTG                                 34

(2) INFORMATION FOR SEQ ID NO: 508:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 508:

CTGAGATGGA GGGCGGCATG GCGGGCACAG GCT                                  33

(2) INFORMATION FOR SEQ ID NO: 509:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 509:

CTGAGATGGA GGGCGGCATG GCGGGCACAG GC                                   32

(2) INFORMATION FOR SEQ ID NO: 510:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 510:

CTGAGATGGA GGGCGGCATG GCGGGCACAG G                                    31

(2) INFORMATION FOR SEQ ID NO: 511:

(i) SEQUENCE CHARACTERISTICS:
            (A) LENGTH: 30 base pairs
            (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO: 511:

CTGAGATGGA GGGCGGCATG GCGGGCACAG                                30

(2) INFORMATION FOR SEQ ID NO: 512:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 512:

CTGAGATGGA GGGCGGCATG GCGGGCACA                                 29

(2) INFORMATION FOR SEQ ID NO: 513:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 513:

CTGAGATGGA GGGCGGCATG GCGGGCAC                                  28

(2) INFORMATION FOR SEQ ID NO: 514:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 514:

CTGAGATGGA GGGCGGCATG GCGGGCA                                   27

(2) INFORMATION FOR SEQ ID NO: 515:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 515:

CTGAGATGGA GGGCGGCATG GCGGGC                                    26

(2) INFORMATION FOR SEQ ID NO: 516:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)
```

```
        (xi) SEQUENCE DESCRIPTION: SEQ ID NO: 516:

CTGAGATGGA GGGCGGCATG GCGGG                                              25

(2) INFORMATION FOR SEQ ID NO: 517:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 517:

CTGAGATGGA GGGCGGCATG GCGG                                               24

(2) INFORMATION FOR SEQ ID NO: 518:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 518:

CTGAGATGGA GGGCGGCATG GCG                                                23

(2) INFORMATION FOR SEQ ID NO: 519:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 519:

CTGAGATGGA GGGCGGCATG GC                                                 22

(2) INFORMATION FOR SEQ ID NO: 520:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 520:

CTGAGATGGA GGGCGGCATG G                                                  21

(2) INFORMATION FOR SEQ ID NO: 521:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 521:

CTGAGATGGA GGGCGGCATG                                                    20
```

(2) INFORMATION FOR SEQ ID NO: 522:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 522:

CTGAGATGGA GGGCGGCAT                                  19

(2) INFORMATION FOR SEQ ID NO: 523:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 523:

CTGAGATGGA GGGCGGCA                                   18

(2) INFORMATION FOR SEQ ID NO: 524:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 524:

CTGAGATGGA GGGCGGC                                    17

(2) INFORMATION FOR SEQ ID NO: 525:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 525:

CTGAGATGGA GGGCGG                                     16

(2) INFORMATION FOR SEQ ID NO: 526:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 526:

CTGAGATGGA GGGCG                                        15

(2) INFORMATION FOR SEQ ID NO: 527:

```
    (i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 527:

CTGAGATGGA GGGC                                                         14

(2) INFORMATION FOR SEQ ID NO: 528:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 528:

CTGAGATGGA GGG                                                          13

(2) INFORMATION FOR SEQ ID NO: 529:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 529:

CTGAGATGGA GG                                                           12

(2) INFORMATION FOR SEQ ID NO: 530:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 530:

CTGAGATGGA G                                                            11

(2) INFORMATION FOR SEQ ID NO: 531:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 531:

CTGAGATGGA                                                              10

(2) INFORMATION FOR SEQ ID NO: 532:

(i) SEQUENCE CHARACTERISTICS:
        (A) LENGTH: 36 base pairs
        (B) TYPE: nucleic acid
        (C) STRANDEDNESS: single
```

-continued (D) TOPOLOGY: linear (ii) MOLECULE TYPE: DNA (genomic)

(xi) SEQUENCE DESCRIPTION: SEQ ID NO: 532:

TGAGATGGAG GGCGGCATGG CGGGCACAGG CTGGGC                                  36

(2) INFORMATION FOR SEQ ID NO: 533:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 533:

TGAGATGGAG GGCGGCATGG CGGGCACAGG CTGGG                                   35

(2) INFORMATION FOR SEQ ID NO: 534:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 534:

TGAGATGGAG GGCGGCATGG CGGGCACAGG CTGG                                    34

(2) INFORMATION FOR SEQ ID NO: 535:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 535:

TGAGATGGAG GGCGGCATGG CGGGCACAGG CTG                                     33

(2) INFORMATION FOR SEQ ID NO: 536:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 536:

TGAGATGGAG GGCGGCATGG CGGGCACAGG CT                                      32

(2) INFORMATION FOR SEQ ID NO: 537:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 537:

TGAGATGGAG GGCGGCATGG CGGGCACAGG C                                       31

(2) INFORMATION FOR SEQ ID NO: 538:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 538:

TGAGATGGAG GGCGGCATGG CGGGCACAGG                                         30

(2) INFORMATION FOR SEQ ID NO: 539:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 539:

TGAGATGGAG GGCGGCATGG CGGGCACAG                                          29

(2) INFORMATION FOR SEQ ID NO: 540:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 540:

TGAGATGGAG GGCGGCATGG CGGGCACA                                           28

(2) INFORMATION FOR SEQ ID NO: 541:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 541:

TGAGATGGAG GGCGGCATGG CGGGCAC                                            27

(2) INFORMATION FOR SEQ ID NO: 542:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 542:

TGAGATGGAG GGCGGCATGG CGGGCA                                             26

```
(2) INFORMATION FOR SEQ ID NO: 543:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 543:

TGAGATGGAG GGCGGCATGG CGGGC                                              25

(2) INFORMATION FOR SEQ ID NO: 544:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 544:

TGAGATGGAG GGCGGCATGG CGGG                                               24

(2) INFORMATION FOR SEQ ID NO: 545:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 545:

TGAGATGGAG GGCGGCATGG CGG                                                23

(2) INFORMATION FOR SEQ ID NO: 546:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 546:

TGAGATGGAG GGCGGCATGG CG                                                 22

(2) INFORMATION FOR SEQ ID NO: 547:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 547:

TGAGATGGAG GGCGGCATGG C                                                  21

(2) INFORMATION FOR SEQ ID NO: 548:

(i) SEQUENCE CHARACTERISTICS:
```

```
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 548:

TGAGATGGAG GGCGGCATGG                                           20

(2) INFORMATION FOR SEQ ID NO: 549:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 549:

TGAGATGGAG GGCGGCATG                                            19

(2) INFORMATION FOR SEQ ID NO: 550:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 550:

TGAGATGGAG GGCGGCAT                                             18

(2) INFORMATION FOR SEQ ID NO: 551:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 551:

TGAGATGGAG GGCGGCA                                              17

(2) INFORMATION FOR SEQ ID NO: 552:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 552:

TGAGATGGAG GGCGGC                                               16

(2) INFORMATION FOR SEQ ID NO: 553:

(i) SEQUENCE CHARACTERISTICS:
        (A) LENGTH: 15 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 553:

TGAGATGGAG GGCGG                                                                15

(2) INFORMATION FOR SEQ ID NO: 554:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 554:

TGAGATGGAG GGCG                                                                 14

(2) INFORMATION FOR SEQ ID NO: 555:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 555:

TGAGATGGAG GGC                                                                  13

(2) INFORMATION FOR SEQ ID NO: 556:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 556:

TGAGATGGAG GG                                                                   12

(2) INFORMATION FOR SEQ ID NO: 557:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 557:

TGAGATGGAG G                                                                    11

(2) INFORMATION FOR SEQ ID NO: 558:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 558:

TGAGATGGAG                                                                       10

(2) INFORMATION FOR SEQ ID NO: 559:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 559:

GAGATGGAGG GCGGCATGGC GGGCACAGGC TGGGC                                            35

(2) INFORMATION FOR SEQ ID NO: 560:

(i) SEQUENCE CHARACTERISTICS:
          (A) LENGTH: 34 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 560:

GAGATGGAGG GCGGCATGGC GGGCACAGGC TGGG                                             34

(2) INFORMATION FOR SEQ ID NO: 561:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 561:

GAGATGGAGG GCGGCATGGC GGGCACAGGC TGG                                              33

(2) INFORMATION FOR SEQ ID NO: 562:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 562:

GAGATGGAGG GCGGCATGGC GGGCACAGGC TG                                               32

(2) INFORMATION FOR SEQ ID NO: 563:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 563:

GAGATGGAGG GCGGCATGGC GGGCACAGGC T                                                31

(2) INFORMATION FOR SEQ ID NO: 564:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 564:

GAGATGGAGG GCGGCATGGC GGGCACAGGC                                              30

(2) INFORMATION FOR SEQ ID NO: 565:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 565:

GAGATGGAGG GCGGCATGGC GGGCACAGG                                               29

(2) INFORMATION FOR SEQ ID NO: 566:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 566:

GAGATGGAGG GCGGCATGGC GGGCACAG                                                28

(2) INFORMATION FOR SEQ ID NO: 567:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 567:

GAGATGGAGG GCGGCATGGC GGGCACA                                                 27

(2) INFORMATION FOR SEQ ID NO: 568:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 568:

GAGATGGAGG GCGGCATGGC GGGCAC                                                  26

(2) INFORMATION FOR SEQ ID NO: 569:

(i) SEQUENCE CHARACTERISTICS:
        (A) LENGTH: 25 base pairs

-continued

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 569:

GAGATGGAGG GCGGCATGGC GGGCA                                            25

(2) INFORMATION FOR SEQ ID NO: 570:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 570:

GAGATGGAGG GCGGCATGGC GGGC                                             24

(2) INFORMATION FOR SEQ ID NO: 571:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 571:

GAGATGGAGG GCGGCATGGC GGG                                              23

(2) INFORMATION FOR SEQ ID NO: 572:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 572:

GAGATGGAGG GCGGCATGGC GG                                               22

(2) INFORMATION FOR SEQ ID NO: 573:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 573:

GAGATGGAGG GCGGCATGGC G                                                21

(2) INFORMATION FOR SEQ ID NO: 574:

(i) SEQUENCE CHARACTERISTICS:
            (A) LENGTH: 20 base pairs
            (B) TYPE: nucleic acid
            (C) STRANDEDNESS: single
            (D) TOPOLOGY: linear
```

(ii) MOLECULE TYPE: DNA (genomic)

(xi) SEQUENCE DESCRIPTION: SEQ ID NO: 574:

GAGATGGAGG GCGGCATGGC                                                    20

(2) INFORMATION FOR SEQ ID NO: 575:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 575:

GAGATGGAGG GCGGCATGG                                                     19

(2) INFORMATION FOR SEQ ID NO: 576:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 576:

GAGATGGAGG GCGGCATG                                                      18

(2) INFORMATION FOR SEQ ID NO: 577:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 577:

GAGATGGAGG GCGGCAT                                                       17

(2) INFORMATION FOR SEQ ID NO: 578:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 578:

GAGATGGAGG GCGGCA                                                        16

(2) INFORMATION FOR SEQ ID NO: 579:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 579:

```
GAGATGGAGG GCGGC                                                          15
```

(2) INFORMATION FOR SEQ ID NO: 580:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 580:

```
GAGATGGAGG GCGG                                                           14
```

(2) INFORMATION FOR SEQ ID NO: 581:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 581:

```
GAGATGGAGG GCG                                                            13
```

(2) INFORMATION FOR SEQ ID NO: 582:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 582:

```
GAGATGGAGG GC                                                             12
```

(2) INFORMATION FOR SEQ ID NO: 583:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 583:

```
GAGATGGAGG G                                                              11
```

(2) INFORMATION FOR SEQ ID NO: 584:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 584:

```
GAGATGGAGG                                                                10
```

(2) INFORMATION FOR SEQ ID NO: 585:

(i) SEQUENCE CHARACTERISTICS:
           (A) LENGTH: 34 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 585:

AGATGGAGGG CGGCATGGCG GGCACAGGCT GGGC                                      34

(2) INFORMATION FOR SEQ ID NO: 586:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 586:

AGATGGAGGG CGGCATGGCG GGCACAGGCT GGG                                       33

(2) INFORMATION FOR SEQ ID NO: 587:

(i) SEQUENCE CHARACTERISTICS:
           (A) LENGTH: 32 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 587:

AGATGGAGGG CGGCATGGCG GGCACAGGCT GG                                        32

(2) INFORMATION FOR SEQ ID NO: 588:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 588:

AGATGGAGGG CGGCATGGCG GGCACAGGCT G                                         31

(2) INFORMATION FOR SEQ ID NO: 589:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 589:

AGATGGAGGG CGGCATGGCG GGCACAGGCT                                           30

(2) INFORMATION FOR SEQ ID NO: 590:

(i) SEQUENCE CHARACTERISTICS:
           (A) LENGTH: 29 base pairs
           (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO: 590:

AGATGGAGGG CGGCATGGCG GGCACAGGC                                    29

(2) INFORMATION FOR SEQ ID NO: 591:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 591:

AGATGGAGGG CGGCATGGCG GGCACAGG                                     28

(2) INFORMATION FOR SEQ ID NO: 592:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 592:

AGATGGAGGG CGGCATGGCG GGCACAG                                      27

(2) INFORMATION FOR SEQ ID NO: 593:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 593:

AGATGGAGGG CGGCATGGCG GGCACA                                       26

(2) INFORMATION FOR SEQ ID NO: 594:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 594:

AGATGGAGGG CGGCATGGCG GGCAC                                        25

(2) INFORMATION FOR SEQ ID NO: 595:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 595:

AGATGGAGGG CGGCATGGCG GGCA                                             24

(2) INFORMATION FOR SEQ ID NO: 596:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 596:

AGATGGAGGG CGGCATGGCG GGC                                              23

(2) INFORMATION FOR SEQ ID NO: 597:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 597:

AGATGGAGGG CGGCATGGCG GG                                               22

(2) INFORMATION FOR SEQ ID NO: 598:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 598:

AGATGGAGGG CGGCATGGCG G                                                21

(2) INFORMATION FOR SEQ ID NO: 599:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 599:

AGATGGAGGG CGGCATGGCG                                                  20

(2) INFORMATION FOR SEQ ID NO: 600:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 600:

AGATGGAGGG CGGCATGGC                                                   19

-continued (2) INFORMATION FOR SEQ ID NO: 601:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 601:

AGATGGAGGG CGGCATGG                                                  18

(2) INFORMATION FOR SEQ ID NO: 602:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 602:

AGATGGAGGG CGGCATG                                                   17

(2) INFORMATION FOR SEQ ID NO: 603:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 603:

AGATGGAGGG CGGCAT                                                     16

(2) INFORMATION FOR SEQ ID NO: 604:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 604:

AGATGGAGGG CGGCA                                                       15

(2) INFORMATION FOR SEQ ID NO: 605:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 605:

AGATGGAGGG CGGC                                                         14

(2) INFORMATION FOR SEQ ID NO: 606:

```
    (i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 606:

AGATGGAGGG CGG                                                        13

(2) INFORMATION FOR SEQ ID NO: 607:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 607:

AGATGGAGGG CG                                                         12

(2) INFORMATION FOR SEQ ID NO: 608:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 608:

AGATGGAGGG C                                                          11

(2) INFORMATION FOR SEQ ID NO: 609:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 609:

AGATGGAGGG                                                            10

(2) INFORMATION FOR SEQ ID NO: 610:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 610:

GATGGAGGGC GGCATGGCGG GCACAGGCTG GGC                                  33

(2) INFORMATION FOR SEQ ID NO: 611:

(i) SEQUENCE CHARACTERISTICS:
        (A) LENGTH: 32 base pairs
        (B) TYPE: nucleic acid
        (C) STRANDEDNESS: single
```

```
        (D) TOPOLOGY: linear (ii) MOLECULE TYPE: DNA (genomic)

(xi) SEQUENCE DESCRIPTION: SEQ ID NO: 611:

GATGGAGGGC GGCATGGCGG GCACAGGCTG GG                                        32

(2) INFORMATION FOR SEQ ID NO: 612:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 612:

GATGGAGGGC GGCATGGCGG GCACAGGCTG G                                         31

(2) INFORMATION FOR SEQ ID NO: 613:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 613:

GATGGAGGGC GGCATGGCGG GCACAGGCTG                                           30

(2) INFORMATION FOR SEQ ID NO: 614:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 614:

GATGGAGGGC GGCATGGCGG GCACAGGCT                                            29

(2) INFORMATION FOR SEQ ID NO: 615:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 615:

GATGGAGGGC GGCATGGCGG GCACAGGC                                             28

(2) INFORMATION FOR SEQ ID NO: 616:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)
```

-continued (xi) SEQUENCE DESCRIPTION: SEQ ID NO: 616:

GATGGAGGGC GGCATGGCGG GCACAGG                                              27

(2) INFORMATION FOR SEQ ID NO: 617:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 617:

GATGGAGGGC GGCATGGCGG GCACAG                                               26

(2) INFORMATION FOR SEQ ID NO: 618:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 618:

GATGGAGGGC GGCATGGCGG GCACA                                                25

(2) INFORMATION FOR SEQ ID NO: 619:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 619:

GATGGAGGGC GGCATGGCGG GCAC                                                 24

(2) INFORMATION FOR SEQ ID NO: 620:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 620:

GATGGAGGGC GGCATGGCGG GCA                                                  23

(2) INFORMATION FOR SEQ ID NO: 621:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 621:

GATGGAGGGC GGCATGGCGG GC                                                   22

(2) INFORMATION FOR SEQ ID NO: 622:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 622:

GATGGAGGGC GGCATGGCGG G                                              21

(2) INFORMATION FOR SEQ ID NO: 623:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 623:

GATGGAGGGC GGCATGGCGG                                                20

(2) INFORMATION FOR SEQ ID NO: 624:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 624:

GATGGAGGGC GGCATGGCG                                                 19

(2) INFORMATION FOR SEQ ID NO: 625:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 625:

GATGGAGGGC GGCATGGC                                                  18

(2) INFORMATION FOR SEQ ID NO: 626:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 626:

GATGGAGGGC GGCATGG                                                   17

(2) INFORMATION FOR SEQ ID NO: 627:

(i) SEQUENCE CHARACTERISTICS:

(A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 627:

GATGGAGGGC GGCATG                                                     16

(2) INFORMATION FOR SEQ ID NO: 628:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 628:

GATGGAGGGC GGCAT                                                      15

(2) INFORMATION FOR SEQ ID NO: 629:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 629:

GATGGAGGGC GGCA                                                       14

(2) INFORMATION FOR SEQ ID NO: 630:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 630:

GATGGAGGGC GGC                                                        13

(2) INFORMATION FOR SEQ ID NO: 631:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 631:

GATGGAGGGC GG                                                         12

(2) INFORMATION FOR SEQ ID NO: 632:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 632:

GATGGAGGGC G                                                11

(2) INFORMATION FOR SEQ ID NO: 633:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 633:

GATGGAGGGC                                                  10

(2) INFORMATION FOR SEQ ID NO: 634:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 634:

ATGGAGGGCG GCATGGCGGG CACAGGCTGG GC                          32

(2) INFORMATION FOR SEQ ID NO: 635:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 635:

ATGGAGGGCG GCATGGCGGG CACAGGCTGG G                           31

(2) INFORMATION FOR SEQ ID NO: 636:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 636:

ATGGAGGGCG GCATGGCGGG CACAGGCTGG                             30

(2) INFORMATION FOR SEQ ID NO: 637:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 637:

```
ATGGAGGGCG GCATGGCGGG CACAGGCTG                                     29

(2) INFORMATION FOR SEQ ID NO: 638:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 638:

ATGGAGGGCG GCATGGCGGG CACAGGCT                                      28

(2) INFORMATION FOR SEQ ID NO: 639:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 639:

ATGGAGGGCG GCATGGCGGG CACAGGC                                       27

(2) INFORMATION FOR SEQ ID NO: 640:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 640:

ATGGAGGGCG GCATGGCGGG CACAGG                                        26

(2) INFORMATION FOR SEQ ID NO: 641:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 641:

ATGGAGGGCG GCATGGCGGG CACAG                                         25

(2) INFORMATION FOR SEQ ID NO: 642:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 642:

ATGGAGGGCG GCATGGCGGG CACA                                          24
```

(2) INFORMATION FOR SEQ ID NO: 643:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 643:

ATGGAGGGCG GCATGGCGGG CAC                                    23

(2) INFORMATION FOR SEQ ID NO: 644:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 644:

ATGGAGGGCG GCATGGCGGG CA                                     22

(2) INFORMATION FOR SEQ ID NO: 645:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 645:

ATGGAGGGCG GCATGGCGGG C                                      21

(2) INFORMATION FOR SEQ ID NO: 646:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 646:

ATGGAGGGCG GCATGGCGGG                                       20

(2) INFORMATION FOR SEQ ID NO: 647:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 647:

ATGGAGGGCG GCATGGCGG                                        19

(2) INFORMATION FOR SEQ ID NO: 648:

(i) SEQUENCE CHARACTERISTICS:
        (A) LENGTH: 18 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 648:

ATGGAGGGCG GCATGGCG                                                18

(2) INFORMATION FOR SEQ ID NO: 649:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 649:

ATGGAGGGCG GCATGGC                                                 17

(2) INFORMATION FOR SEQ ID NO: 650:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 650:

ATGGAGGGCG GCATGG                                                  16

(2) INFORMATION FOR SEQ ID NO: 651:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 651:

ATGGAGGGCG GCATG                                                   15

(2) INFORMATION FOR SEQ ID NO: 652:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 652:

ATGGAGGGCG GCAT                                                    14

(2) INFORMATION FOR SEQ ID NO: 653:

(i) SEQUENCE CHARACTERISTICS:
            (A) LENGTH: 13 base pairs
            (B) TYPE: nucleic acid
            (C) STRANDEDNESS: single
            (D) TOPOLOGY: linear
```

(ii) MOLECULE TYPE: DNA (genomic)

(xi) SEQUENCE DESCRIPTION: SEQ ID NO: 653:

ATGGAGGGCG GCA                                                          13

(2) INFORMATION FOR SEQ ID NO: 654:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 654:

ATGGAGGGCG GC                                                           12

(2) INFORMATION FOR SEQ ID NO: 655:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 655:

ATGGAGGGCG G                                                            11

(2) INFORMATION FOR SEQ ID NO: 656:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 656:

ATGGAGGGCG                                                              10

(2) INFORMATION FOR SEQ ID NO: 657:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 657:

TGGAGGGCGG CATGGCGGGC ACAGGCTGGG C                                      31

(2) INFORMATION FOR SEQ ID NO: 658:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 658:

```
TGGAGGGCGG CATGGCGGGC ACAGGCTGGG                                    30

(2) INFORMATION FOR SEQ ID NO: 659:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 659:

TGGAGGGCGG CATGGCGGGC ACAGGCTGG                                     29

(2) INFORMATION FOR SEQ ID NO: 660:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 660:

TGGAGGGCGG CATGGCGGGC ACAGGCTG                                      28

(2) INFORMATION FOR SEQ ID NO: 661:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 661:

TGGAGGGCGG CATGGCGGGC ACAGGCT                                       27

(2) INFORMATION FOR SEQ ID NO: 662:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 662:

TGGAGGGCGG CATGGCGGGC ACAGGC                                        26

(2) INFORMATION FOR SEQ ID NO: 663:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 663:

TGGAGGGCGG CATGGCGGGC ACAGG                                         25

(2) INFORMATION FOR SEQ ID NO: 664:
```

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 664:

TGGAGGGCGG CATGGCGGGC ACAG                                              24

(2) INFORMATION FOR SEQ ID NO: 665:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 665:

TGGAGGGCGG CATGGCGGGC ACA                                               23

(2) INFORMATION FOR SEQ ID NO: 666:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 666:

TGGAGGGCGG CATGGCGGGC AC                                                22

(2) INFORMATION FOR SEQ ID NO: 667:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 667:

TGGAGGGCGG CATGGCGGGC A                                                 21

(2) INFORMATION FOR SEQ ID NO: 668:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 668:

TGGAGGGCGG CATGGCGGGC                                                   20

(2) INFORMATION FOR SEQ ID NO: 669:

(i) SEQUENCE CHARACTERISTICS:
        (A) LENGTH: 19 base pairs
        (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO: 669:

TGGAGGGCGG CATGGCGGG                                                    19

(2) INFORMATION FOR SEQ ID NO: 670:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 670:

TGGAGGGCGG CATGGCGG                                                     18

(2) INFORMATION FOR SEQ ID NO: 671:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 671:

TGGAGGGCGG CATGGCG                                                      17

(2) INFORMATION FOR SEQ ID NO: 672:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 672:

TGGAGGGCGG CATGGC                                                       16

(2) INFORMATION FOR SEQ ID NO: 673:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 673:

TGGAGGGCGG CATGG                                                        15

(2) INFORMATION FOR SEQ ID NO: 674:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 674:

TGGAGGGCGG CATG                                                           14

(2) INFORMATION FOR SEQ ID NO: 675:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 675:

TGGAGGGCGG CAT                                                            13

(2) INFORMATION FOR SEQ ID NO: 676:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 676:

TGGAGGGCGG CA                                                             12

(2) INFORMATION FOR SEQ ID NO: 677:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 677:

TGGAGGGCGG C                                                              11

(2) INFORMATION FOR SEQ ID NO: 678:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 678:

TGGAGGGCGG                                                                10

(2) INFORMATION FOR SEQ ID NO: 679:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 679:

GGAGGGCGGC ATGGCGGGCA CAGGCTGGGC                                          30

(2) INFORMATION FOR SEQ ID NO: 680:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 680:

GGAGGGCGGC ATGGCGGGCA CAGGCTGGG                              29

(2) INFORMATION FOR SEQ ID NO: 681:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 681:

GGAGGGCGGC ATGGCGGGCA CAGGCTGG                               28

(2) INFORMATION FOR SEQ ID NO: 682:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 682:

GGAGGGCGGC ATGGCGGGCA CAGGCTG                                27

(2) INFORMATION FOR SEQ ID NO: 683:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 683:

GGAGGGCGGC ATGGCGGGCA CAGGCT                                 26

(2) INFORMATION FOR SEQ ID NO: 684:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 684:

GGAGGGCGGC ATGGCGGGCA CAGGC                                  25

(2) INFORMATION FOR SEQ ID NO: 685:

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 685:

GGAGGGCGGC ATGGCGGGCA CAGG                                              24

(2) INFORMATION FOR SEQ ID NO: 686:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 686:

GGAGGGCGGC ATGGCGGGCA CAG                                               23

(2) INFORMATION FOR SEQ ID NO: 687:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 687:

GGAGGGCGGC ATGGCGGGCA CA                                                22

(2) INFORMATION FOR SEQ ID NO: 688:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 688:

GGAGGGCGGC ATGGCGGGCA C                                                 21

(2) INFORMATION FOR SEQ ID NO: 689:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 689:

GGAGGGCGGC ATGGCGGGCA                                                   20

(2) INFORMATION FOR SEQ ID NO: 690:

(i) SEQUENCE CHARACTERISTICS:
        (A) LENGTH: 19 base pairs
        (B) TYPE: nucleic acid
        (C) STRANDEDNESS: single
```

-continued (D) TOPOLOGY: linear (ii) MOLECULE TYPE: DNA (genomic)

(xi) SEQUENCE DESCRIPTION: SEQ ID NO: 690:

GGAGGGCGGC ATGGCGGGC                                                19

(2) INFORMATION FOR SEQ ID NO: 691:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 691:

GGAGGGCGGC ATGGCGGG                                                 18

(2) INFORMATION FOR SEQ ID NO: 692:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 692:

GGAGGGCGGC ATGGCGG                                                  17

(2) INFORMATION FOR SEQ ID NO: 693:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 693:

GGAGGGCGGC ATGGCG                                                   16

(2) INFORMATION FOR SEQ ID NO: 694:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 694:

GGAGGGCGGC ATGGC                                                    15

(2) INFORMATION FOR SEQ ID NO: 695:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: DNA (genomic)

```
    (xi) SEQUENCE DESCRIPTION: SEQ ID NO: 695:

GGAGGGCGGC ATGG                                                          14

(2) INFORMATION FOR SEQ ID NO: 696:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 696:

GGAGGGCGGC ATG                                                           13

(2) INFORMATION FOR SEQ ID NO: 697:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 697:

GGAGGGCGGC AT                                                            12

(2) INFORMATION FOR SEQ ID NO: 698:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 698:

GGAGGGCGGC A                                                             11

(2) INFORMATION FOR SEQ ID NO: 699:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 699:

GGAGGGCGGC                                                               10

(2) INFORMATION FOR SEQ ID NO: 700:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 700:

GAGGGCGGCA TGGCGGGCAC AGGCTGGGC                                          29
```

(2) INFORMATION FOR SEQ ID NO: 701:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 701:

GAGGGCGGCA TGGCGGGCAC AGGCTGGG                         28

(2) INFORMATION FOR SEQ ID NO: 702:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 702:

GAGGGCGGCA TGGCGGGCAC AGGCTGG                          27

(2) INFORMATION FOR SEQ ID NO: 703:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 703:

GAGGGCGGCA TGGCGGGCAC AGGCTG                           26

(2) INFORMATION FOR SEQ ID NO: 704:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 704:

GAGGGCGGCA TGGCGGGCAC AGGCT                            25

(2) INFORMATION FOR SEQ ID NO: 705:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 705:

GAGGGCGGCA TGGCGGGCAC AGGC                             24

(2) INFORMATION FOR SEQ ID NO: 706:

(i) SEQUENCE CHARACTERISTICS:

(A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 706:

GAGGGCGGCA TGGCGGGCAC AGG                                               23

(2) INFORMATION FOR SEQ ID NO: 707:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 707:

GAGGGCGGCA TGGCGGGCAC AG                                                22

(2) INFORMATION FOR SEQ ID NO: 708:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 708:

GAGGGCGGCA TGGCGGGCAC A                                                 21

(2) INFORMATION FOR SEQ ID NO: 709:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 709:

GAGGGCGGCA TGGCGGGCAC                                                   20

(2) INFORMATION FOR SEQ ID NO: 710:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 710:

GAGGGCGGCA TGGCGGGCA                                                    19

(2) INFORMATION FOR SEQ ID NO: 711:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 711:

GAGGGCGGCA TGGCGGGC                                                 18

(2) INFORMATION FOR SEQ ID NO: 712:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 712:

GAGGGCGGCA TGGCGGG                                                  17

(2) INFORMATION FOR SEQ ID NO: 713:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 713:

GAGGGCGGCA TGGCGG                                                   16

(2) INFORMATION FOR SEQ ID NO: 714:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 714:

GAGGGCGGCA TGGCG                                                    15

(2) INFORMATION FOR SEQ ID NO: 715:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 715:

GAGGGCGGCA TGGC                                                     14

(2) INFORMATION FOR SEQ ID NO: 716:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 716:

```
GAGGGCGGCA TGG                                                              13

(2) INFORMATION FOR SEQ ID NO: 717:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 717:

GAGGGCGGCA TG                                                               12

(2) INFORMATION FOR SEQ ID NO: 718:

(i) SEQUENCE CHARACTERISTICS:
          (A) LENGTH: 11 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 718:

GAGGGCGGCA T                                                                11

(2) INFORMATION FOR SEQ ID NO: 719:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 719:

GAGGGCGGCA                                                                  10

(2) INFORMATION FOR SEQ ID NO: 720:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 720:

AGGGCGGCAT GGCGGGCACA GGCTGGGC                                              28

(2) INFORMATION FOR SEQ ID NO: 721:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 721:

AGGGCGGCAT GGCGGGCACA GGCTGGG                                               27
```

(2) INFORMATION FOR SEQ ID NO: 722:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 722:

AGGGCGGCAT GGCGGGCACA GGCTGG     26

(2) INFORMATION FOR SEQ ID NO: 723:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 723:

AGGGCGGCAT GGCGGGCACA GGCTG     25

(2) INFORMATION FOR SEQ ID NO: 724:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 724:

AGGGCGGCAT GGCGGGCACA GGCT     24

(2) INFORMATION FOR SEQ ID NO: 725:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 725:

AGGGCGGCAT GGCGGGCACA GGC     23

(2) INFORMATION FOR SEQ ID NO: 726:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 726:

AGGGCGGCAT GGCGGGCACA GG     22

(2) INFORMATION FOR SEQ ID NO: 727:

(i) SEQUENCE CHARACTERISTICS:
        (A) LENGTH: 21 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 727:

AGGGCGGCAT GGCGGGCACA G                                           21

(2) INFORMATION FOR SEQ ID NO: 728:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 728:

AGGGCGGCAT GGCGGGCACA                                             20

(2) INFORMATION FOR SEQ ID NO: 729:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 729:

AGGGCGGCAT GGCGGGCAC                                              19

(2) INFORMATION FOR SEQ ID NO: 730:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 730:

AGGGCGGCAT GGCGGGCA                                               18

(2) INFORMATION FOR SEQ ID NO: 731:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 731:

AGGGCGGCAT GGCGGGC                                                17

(2) INFORMATION FOR SEQ ID NO: 732:

(i) SEQUENCE CHARACTERISTICS:
        (A) LENGTH: 16 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 732:

AGGGCGGCAT GGCGGG                                                16

(2) INFORMATION FOR SEQ ID NO: 733:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 733:

AGGGCGGCAT GGCGG                                                 15

(2) INFORMATION FOR SEQ ID NO: 734:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 734:

AGGGCGGCAT GGCG                                                  14

(2) INFORMATION FOR SEQ ID NO: 735:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 735:

AGGGCGGCAT GGC                                                   13

(2) INFORMATION FOR SEQ ID NO: 736:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 736:

AGGGCGGCAT GG                                                    12

(2) INFORMATION FOR SEQ ID NO: 737:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 737:

```
AGGGCGGCAT G                                                                    11

(2) INFORMATION FOR SEQ ID NO: 738:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 738:

AGGGCGGCAT                                                                      10

(2) INFORMATION FOR SEQ ID NO: 739:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 739:

GGGCGGCATG GCGGGCACAG GCTGGGC                                                   27

(2) INFORMATION FOR SEQ ID NO: 740:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 740:

GGGCGGCATG GCGGGCACAG GCTGGG                                                    26

(2) INFORMATION FOR SEQ ID NO: 741:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 741:

GGGCGGCATG GCGGGCACAG GCTGG                                                     25

(2) INFORMATION FOR SEQ ID NO: 742:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 742:

GGGCGGCATG GCGGGCACAG GCTG                                                      24

(2) INFORMATION FOR SEQ ID NO: 743:
```

```
    (i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 743:

GGGCGGCATG GCGGGCACAG GCT                                               23

(2) INFORMATION FOR SEQ ID NO: 744:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 744:

GGGCGGCATG GCGGGCACAG GC                                                22

(2) INFORMATION FOR SEQ ID NO: 745:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 745:

GGGCGGCATG GCGGGCACAG G                                                 21

(2) INFORMATION FOR SEQ ID NO: 746:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 746:

GGGCGGCATG GCGGGCACAG                                                   20

(2) INFORMATION FOR SEQ ID NO: 747:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 747:

GGGCGGCATG GCGGGCACA                                                    19

(2) INFORMATION FOR SEQ ID NO: 748:

(i) SEQUENCE CHARACTERISTICS:
        (A) LENGTH: 18 base pairs
        (B) TYPE: nucleic acid
```

```
          (C) STRANDEDNESS: single
          (D) TOPOLOGY: linear (ii) MOLECULE TYPE: DNA (genomic)

(xi) SEQUENCE DESCRIPTION: SEQ ID NO: 748:

GGGCGGCATG GCGGGCAC                                           18

(2) INFORMATION FOR SEQ ID NO: 749:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 749:

GGGCGGCATG GCGGGCA                                            17

(2) INFORMATION FOR SEQ ID NO: 750:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 750:

GGGCGGCATG GCGGGC                                             16

(2) INFORMATION FOR SEQ ID NO: 751:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 751:

GGGCGGCATG GCGGG                                              15

(2) INFORMATION FOR SEQ ID NO: 752:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 752:

GGGCGGCATG GCGG                                               14

(2) INFORMATION FOR SEQ ID NO: 753:

(i) SEQUENCE CHARACTERISTICS:
          (A) LENGTH: 13 base pairs
          (B) TYPE: nucleic acid
          (C) STRANDEDNESS: single
          (D) TOPOLOGY: linear (ii) MOLECULE TYPE: DNA (genomic)
```

(xi) SEQUENCE DESCRIPTION: SEQ ID NO: 753:

GGGCGGCATG GCG                                                              13

(2) INFORMATION FOR SEQ ID NO: 754:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 754:

GGGCGGCATG GC                                                               12

(2) INFORMATION FOR SEQ ID NO: 755:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 755:

GGGCGGCATG G                                                                11

(2) INFORMATION FOR SEQ ID NO: 756:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 756:

GGGCGGCATG                                                                  10

(2) INFORMATION FOR SEQ ID NO: 757:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 757:

GGCGGCATGG CGGGCACAGG CTGGGC                                                26

(2) INFORMATION FOR SEQ ID NO: 758:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 758:

GGCGGCATGG CGGGCACAGG CTGGG                                                 25

(2) INFORMATION FOR SEQ ID NO: 759:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 759:

GGCGGCATGG CGGGCACAGG CTGG                           24

(2) INFORMATION FOR SEQ ID NO: 760:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 760:

GGCGGCATGG CGGGCACAGG CTG                            23

(2) INFORMATION FOR SEQ ID NO: 761:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 761:

GGCGGCATGG CGGGCACAGG CT                             22

(2) INFORMATION FOR SEQ ID NO: 762:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 762:

GGCGGCATGG CGGGCACAGG C                               21

(2) INFORMATION FOR SEQ ID NO: 763:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 763:

GGCGGCATGG CGGGCACAGG                                20

(2) INFORMATION FOR SEQ ID NO: 764:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 764:

GGCGGCATGG CGGGCACAG                                              19

(2) INFORMATION FOR SEQ ID NO: 765:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 765:

GGCGGCATGG CGGGCACA                                               18

(2) INFORMATION FOR SEQ ID NO: 766:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 766:

GGCGGCATGG CGGGCAC                                                17

(2) INFORMATION FOR SEQ ID NO: 767:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 767:

GGCGGCATGG CGGGCA                                                 16

(2) INFORMATION FOR SEQ ID NO: 768:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 768:

GGCGGCATGG CGGGC                                                  15

(2) INFORMATION FOR SEQ ID NO: 769:

(i) SEQUENCE CHARACTERISTICS:
       (A) LENGTH: 14 base pairs
       (B) TYPE: nucleic acid
       (C) STRANDEDNESS: single -continued (D) TOPOLOGY: linear (ii) MOLECULE TYPE: DNA (genomic)

(xi) SEQUENCE DESCRIPTION: SEQ ID NO: 769:

GGCGGCATGG CGGG                                                      14

(2) INFORMATION FOR SEQ ID NO: 770:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 770:

GGCGGCATGG CGG                                                       13

(2) INFORMATION FOR SEQ ID NO: 771:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 771:

GGCGGCATGG CG                                                         12

(2) INFORMATION FOR SEQ ID NO: 772:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 772:

GGCGGCATGG C                                                           11

(2) INFORMATION FOR SEQ ID NO: 773:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 773:

GGCGGCATGG                                                              10

(2) INFORMATION FOR SEQ ID NO: 774:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

```
     (xi) SEQUENCE DESCRIPTION: SEQ ID NO: 774:

GCGGCATGGC GGGCACAGGC TGGGC                                              25

(2) INFORMATION FOR SEQ ID NO: 775:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 775:

GCGGCATGGC GGGCACAGGC TGGG                                               24

(2) INFORMATION FOR SEQ ID NO: 776:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 776:

GCGGCATGGC GGGCACAGGC TGG                                                23

(2) INFORMATION FOR SEQ ID NO: 777:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 777:

GCGGCATGGC GGGCACAGGC TG                                                 22

(2) INFORMATION FOR SEQ ID NO: 778:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 778:

GCGGCATGGC GGGCACAGGC T                                                  21

(2) INFORMATION FOR SEQ ID NO: 779:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 779:

GCGGCATGGC GGGCACAGGC                                                    20
```

-continued (2) INFORMATION FOR SEQ ID NO: 780:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 780:

GCGGCATGGC GGGCACAGG                                                19

(2) INFORMATION FOR SEQ ID NO: 781:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 781:

GCGGCATGGC GGGCACAG                                                 18

(2) INFORMATION FOR SEQ ID NO: 782:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 782:

GCGGCATGGC GGGCACA                                                  17

(2) INFORMATION FOR SEQ ID NO: 783:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 783:

GCGGCATGGC GGGCAC                                                   16

(2) INFORMATION FOR SEQ ID NO: 784:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 784:

GCGGCATGGC GGGCA                                                    15

(2) INFORMATION FOR SEQ ID NO: 785:

(i) SEQUENCE CHARACTERISTICS:

(A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 785:

GCGGCATGGC GGGC                                                           14

(2) INFORMATION FOR SEQ ID NO: 786:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 786:

GCGGCATGGC GGG                                                            13

(2) INFORMATION FOR SEQ ID NO: 787:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 787:

GCGGCATGGC GG                                                             12

(2) INFORMATION FOR SEQ ID NO: 788:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 788:

GCGGCATGGC G                                                              11

(2) INFORMATION FOR SEQ ID NO: 789:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 789:

GCGGCATGGC                                                                10

(2) INFORMATION FOR SEQ ID NO: 790:

(i) SEQUENCE CHARACTERISTICS:
        (A) LENGTH: 24 base pairs
        (B) TYPE: nucleic acid
        (C) STRANDEDNESS: single
        (D) TOPOLOGY: linear

```
    (ii) MOLECULE TYPE: DNA (genomic)

(xi) SEQUENCE DESCRIPTION: SEQ ID NO: 790:

CGGCATGGCG GGCACAGGCT GGGC                                           24

(2) INFORMATION FOR SEQ ID NO: 791:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 791:

CGGCATGGCG GGCACAGGCT GGG                                            23

(2) INFORMATION FOR SEQ ID NO: 792:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 792:

CGGCATGGCG GGCACAGGCT GG                                             22

(2) INFORMATION FOR SEQ ID NO: 793:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 793:

CGGCATGGCG GGCACAGGCT G                                              21

(2) INFORMATION FOR SEQ ID NO: 794:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 794:

CGGCATGGCG GGCACAGGCT                                                20

(2) INFORMATION FOR SEQ ID NO: 795:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 795:
```

```
CGGCATGGCG GGCACAGGC                                                  19

(2) INFORMATION FOR SEQ ID NO: 796:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 796:

CGGCATGGCG GGCACAGG                                                   18

(2) INFORMATION FOR SEQ ID NO: 797:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 797:

CGGCATGGCG GGCACAG                                                    17

(2) INFORMATION FOR SEQ ID NO: 798:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 798:

CGGCATGGCG GGCACA                                                     16

(2) INFORMATION FOR SEQ ID NO: 799:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 799:

CGGCATGGCG GGCAC                                                      15

(2) INFORMATION FOR SEQ ID NO: 800:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 800:

CGGCATGGCG GGCA                                                       14
```

(2) INFORMATION FOR SEQ ID NO: 801:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 801:

CGGCATGGCG GGC                                                      13

(2) INFORMATION FOR SEQ ID NO: 802:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 802:

CGGCATGGCG GG                                                       12

(2) INFORMATION FOR SEQ ID NO: 803:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 803:

CGGCATGGCG G                                                         11

(2) INFORMATION FOR SEQ ID NO: 804:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 804:

CGGCATGGCG                                                            10

(2) INFORMATION FOR SEQ ID NO: 805:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 805:

GGCATGGCGG GCACAGGCTG GGC                                  23

(2) INFORMATION FOR SEQ ID NO: 806:

(i) SEQUENCE CHARACTERISTICS:
        (A) LENGTH: 22 base pairs (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 806:

GGCATGGCGG GCACAGGCTG GG                                            22

(2) INFORMATION FOR SEQ ID NO: 807:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 807:

GGCATGGCGG GCACAGGCTG G                                             21

(2) INFORMATION FOR SEQ ID NO: 808:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 808:

GGCATGGCGG GCACAGGCTG                                               20

(2) INFORMATION FOR SEQ ID NO: 809:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 809:

GGCATGGCGG GCACAGGCT                                                19

(2) INFORMATION FOR SEQ ID NO: 810:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 810:

GGCATGGCGG GCACAGGC                                                 18

(2) INFORMATION FOR SEQ ID NO: 811:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 811:

GGCATGGCGG GCACAGG                                                          17

(2) INFORMATION FOR SEQ ID NO: 812:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 812:

GGCATGGCGG GCACAG                                                           16

(2) INFORMATION FOR SEQ ID NO: 813:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 813:

GGCATGGCGG GCACA                                                            15

(2) INFORMATION FOR SEQ ID NO: 814:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 814:

GGCATGGCGG GCAC                                                             14

(2) INFORMATION FOR SEQ ID NO: 815:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 815:

GGCATGGCGG GCA                                                              13

(2) INFORMATION FOR SEQ ID NO: 816:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 816:

```
GGCATGGCGG GC                                                   12

(2) INFORMATION FOR SEQ ID NO: 817:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 817:

GGCATGGCGG G                                                    11

(2) INFORMATION FOR SEQ ID NO: 818:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 818:

GGCATGGCGG                                                      10

(2) INFORMATION FOR SEQ ID NO: 819:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 819:

GCATGGCGGG CACAGGCTGG GC                                        22

(2) INFORMATION FOR SEQ ID NO: 820:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 820:

GCATGGCGGG CACAGGCTGG G                                         21

(2) INFORMATION FOR SEQ ID NO: 821:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 821:

GCATGGCGGG CACAGGCTGG                                           20

(2) INFORMATION FOR SEQ ID NO: 822:
```

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 822:

GCATGGCGGG CACAGGCTG                                            19

(2) INFORMATION FOR SEQ ID NO: 823:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 823:

GCATGGCGGG CACAGGCT                                             18

(2) INFORMATION FOR SEQ ID NO: 824:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 824:

GCATGGCGGG CACAGGC                                              17

(2) INFORMATION FOR SEQ ID NO: 825:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 825:

GCATGGCGGG CACAGG                                               16

(2) INFORMATION FOR SEQ ID NO: 826:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 826:

GCATGGCGGG CACAG                                                15

(2) INFORMATION FOR SEQ ID NO: 827:

(i) SEQUENCE CHARACTERISTICS:
        (A) LENGTH: 14 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO: 827:

GCATGGCGGG CACA                                              14

(2) INFORMATION FOR SEQ ID NO: 828:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 828:

GCATGGCGGG CAC                                               13

(2) INFORMATION FOR SEQ ID NO: 829:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 829:

GCATGGCGGG CA                                                12

(2) INFORMATION FOR SEQ ID NO: 830:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 830:

GCATGGCGGG C                                                 11

(2) INFORMATION FOR SEQ ID NO: 831:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 831:

GCATGGCGGG                                                   10

(2) INFORMATION FOR SEQ ID NO: 832:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 832:

CATGGCGGGC ACAGGCTGGG C                                       21

(2) INFORMATION FOR SEQ ID NO: 833:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 833:

CATGGCGGGC ACAGGCTGGG                                         20

(2) INFORMATION FOR SEQ ID NO: 834:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 834:

CATGGCGGGC ACAGGCTGG                                          19

(2) INFORMATION FOR SEQ ID NO: 835:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 835:

CATGGCGGGC ACAGGCTG                                           18

(2) INFORMATION FOR SEQ ID NO: 836:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 836:

CATGGCGGGC ACAGGCT                                            17

(2) INFORMATION FOR SEQ ID NO: 837:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 837:

CATGGCGGGC ACAGGC                                             16

(2) INFORMATION FOR SEQ ID NO: 838:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 838:

CATGGCGGGC ACAGG                                               15

(2) INFORMATION FOR SEQ ID NO: 839:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 839:

CATGGCGGGC ACAG                                                14

(2) INFORMATION FOR SEQ ID NO: 840:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 840:

CATGGCGGGC ACA                                                 13

(2) INFORMATION FOR SEQ ID NO: 841:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 841:

CATGGCGGGC AC                                                  12

(2) INFORMATION FOR SEQ ID NO: 842:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 842:

CATGGCGGGC A                                                   11

(2) INFORMATION FOR SEQ ID NO: 843:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 843:

CATGGCGGGC                                                              10

(2) INFORMATION FOR SEQ ID NO: 844:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 844:

ATGGCGGGCA CAGGCTGGGC                                                   20

(2) INFORMATION FOR SEQ ID NO: 845:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 845:

ATGGCGGGCA CAGGCTGGG                                                    19

(2) INFORMATION FOR SEQ ID NO: 846:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 846:

ATGGCGGGCA CAGGCTGG                                                     18

(2) INFORMATION FOR SEQ ID NO: 847:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 847:

ATGGCGGGCA CAGGCTG                                                      17

(2) INFORMATION FOR SEQ ID NO: 848:

(i) SEQUENCE CHARACTERISTICS:
            (A) LENGTH: 16 base pairs
            (B) TYPE: nucleic acid
            (C) STRANDEDNESS: single

```
        (D) TOPOLOGY: linear (ii) MOLECULE TYPE: DNA (genomic)

(xi) SEQUENCE DESCRIPTION: SEQ ID NO: 848:

ATGGCGGGCA CAGGCT                                              16

(2) INFORMATION FOR SEQ ID NO: 849:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 849:

ATGGCGGGCA CAGGC                                               15

(2) INFORMATION FOR SEQ ID NO: 850:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 850:

ATGGCGGGCA CAGG                                                14

(2) INFORMATION FOR SEQ ID NO: 851:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 851:

ATGGCGGGCA CAG                                                 13

(2) INFORMATION FOR SEQ ID NO: 852:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 852:

ATGGCGGGCA CA                                                  12

(2) INFORMATION FOR SEQ ID NO: 853:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)
```

```
    (xi) SEQUENCE DESCRIPTION: SEQ ID NO: 853:

ATGGCGGGCA C                                                        11

(2) INFORMATION FOR SEQ ID NO: 854:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 854:

ATGGCGGGCA                                                          10

(2) INFORMATION FOR SEQ ID NO: 855:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 855:

TGGCGGGCAC AGGCTGGGC                                                19

(2) INFORMATION FOR SEQ ID NO: 856:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 856:

TGGCGGGCAC AGGCTGGG                                                 18

(2) INFORMATION FOR SEQ ID NO: 857:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 857:

TGGCGGGCAC AGGCTGG                                              17

(2) INFORMATION FOR SEQ ID NO: 858:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 858:

TGGCGGGCAC AGGCTG                                                   16
```

(2) INFORMATION FOR SEQ ID NO: 859:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 859:

TGGCGGGCAC AGGCT                                                 15

(2) INFORMATION FOR SEQ ID NO: 860:

(i) SEQUENCE CHARACTERISTICS:
       (A) LENGTH: 14 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 860:

TGGCGGGCAC AGGC                                                  14

(2) INFORMATION FOR SEQ ID NO: 861:

(i) SEQUENCE CHARACTERISTICS:
       (A) LENGTH: 13 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 861:

TGGCGGGCAC AGG                                                   13

(2) INFORMATION FOR SEQ ID NO: 862:

(i) SEQUENCE CHARACTERISTICS:
       (A) LENGTH: 12 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 862:

TGGCGGGCAC AG                                                    12

(2) INFORMATION FOR SEQ ID NO: 863:

(i) SEQUENCE CHARACTERISTICS:
       (A) LENGTH: 11 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 863:

TGGCGGGCAC A                                                     11

(2) INFORMATION FOR SEQ ID NO: 864:

(i) SEQUENCE CHARACTERISTICS:

(A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 864:

TGGCGGGCAC                                                          10

(2) INFORMATION FOR SEQ ID NO: 865:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 865:

GGCGGGCACA GGCTGGGC                                                 18

(2) INFORMATION FOR SEQ ID NO: 866:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 866:

GGCGGGCACA GGCTGGG                                                  17

(2) INFORMATION FOR SEQ ID NO: 867:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 867:

GGCGGGCACA GGCTGG                                                   16

(2) INFORMATION FOR SEQ ID NO: 868:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 868:

GGCGGGCACA GGCTG                                                    15

(2) INFORMATION FOR SEQ ID NO: 869:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 869:

GGCGGGCACA GGCT                                                                14

(2) INFORMATION FOR SEQ ID NO: 870:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 870:

GGCGGGCACA GGC                                                                 13

(2) INFORMATION FOR SEQ ID NO: 871:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 871:

GGCGGGCACA GG                                                                  12

(2) INFORMATION FOR SEQ ID NO: 872:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 872:

GGCGGGCACA G                                                                   11

(2) INFORMATION FOR SEQ ID NO: 873:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 873:

GGCGGGCACA                                                                     10

(2) INFORMATION FOR SEQ ID NO: 874:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 874:

```
GCGGGCACAG GCTGGGC                                                    17

(2) INFORMATION FOR SEQ ID NO: 875:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 875:

GCGGGCACAG GCTGGG                                                     16

(2) INFORMATION FOR SEQ ID NO: 876:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 876:

GCGGGCACAG GCTGG                                                      15

(2) INFORMATION FOR SEQ ID NO: 877:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 877:

GCGGGCACAG GCTG                                                       14

(2) INFORMATION FOR SEQ ID NO: 878:

(i) SEQUENCE CHARACTERISTICS:
         (A) LENGTH: 13 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 878:

GCGGGCACAG GCT                                                        13

(2) INFORMATION FOR SEQ ID NO: 879:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 879:

GCGGGCACAG GC                                                         12
```

-continued (2) INFORMATION FOR SEQ ID NO: 880:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 880:

GCGGGCACAG G                                        11

(2) INFORMATION FOR SEQ ID NO: 881:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 881:

GCGGGCACAG                                        10

(2) INFORMATION FOR SEQ ID NO: 882:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 882:

CGGGCACAGG CTGGGC                                16

(2) INFORMATION FOR SEQ ID NO: 883:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 883:

CGGGCACAGG CTGGG                                 15

(2) INFORMATION FOR SEQ ID NO: 884:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 884:

CGGGCACAGG CTGG                                  14

(2) INFORMATION FOR SEQ ID NO: 885:

(i) SEQUENCE CHARACTERISTICS:
        (A) LENGTH: 13 base pairs

```
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 885:

CGGGCACAGG CTG                                                          13

(2) INFORMATION FOR SEQ ID NO: 886:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 886:

CGGGCACAGG CT                                                           12

(2) INFORMATION FOR SEQ ID NO: 887:

(i) SEQUENCE CHARACTERISTICS:
          (A) LENGTH: 11 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 887:

CGGGCACAGG C                                                            11

(2) INFORMATION FOR SEQ ID NO: 888:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 888:

CGGGCACAGG                                                              10

(2) INFORMATION FOR SEQ ID NO: 889:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 889:

GGGCACAGGC TGGGC                                                        15

(2) INFORMATION FOR SEQ ID NO: 890:

(i) SEQUENCE CHARACTERISTICS:
          (A) LENGTH: 14 base pairs
          (B) TYPE: nucleic acid
          (C) STRANDEDNESS: single
          (D) TOPOLOGY: linear
```

(ii) MOLECULE TYPE: DNA (genomic)

(xi) SEQUENCE DESCRIPTION: SEQ ID NO: 890:

GGGCACAGGC TGGG                                                          14

(2) INFORMATION FOR SEQ ID NO: 891:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 891:

GGGCACAGGC TGG                                                           13

(2) INFORMATION FOR SEQ ID NO: 892:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 892:

GGGCACAGGC TG                                                            12

(2) INFORMATION FOR SEQ ID NO: 893:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 893:

GGGCACAGGC T                                                             11

(2) INFORMATION FOR SEQ ID NO: 894:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 894:

GGGCACAGGC                                                               10

(2) INFORMATION FOR SEQ ID NO: 895:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 895:

-continued

GGCACAGGCT GGGC                                      14

(2) INFORMATION FOR SEQ ID NO: 896:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 896:

GGCACAGGCT GGG                                       13

(2) INFORMATION FOR SEQ ID NO: 897:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 897:

GGCACAGGCT GG                                        12

(2) INFORMATION FOR SEQ ID NO: 898:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 898:

GGCACAGGCT G                                         11

(2) INFORMATION FOR SEQ ID NO: 899:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 899:

GGCACAGGCT                                           10

(2) INFORMATION FOR SEQ ID NO: 900:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 900:

GCACAGGCTG GGC                                       13

(2) INFORMATION FOR SEQ ID NO: 901:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 901:

GCACAGGCTG GG                                                              12

(2) INFORMATION FOR SEQ ID NO: 902:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 902:

GCACAGGCTG G                                                               11

(2) INFORMATION FOR SEQ ID NO: 903:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 903:

GCACAGGCTG                                                                 10

(2) INFORMATION FOR SEQ ID NO: 904:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 904:

CACAGGCTGG GC                                                              12

(2) INFORMATION FOR SEQ ID NO: 905:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 905:

CACAGGCTGG G                                                               11

(2) INFORMATION FOR SEQ ID NO: 906:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO: 906:

CACAGGCTGG                                                              10

(2) INFORMATION FOR SEQ ID NO: 907:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 907:

ACAGGCTGGG C                                                            11

(2) INFORMATION FOR SEQ ID NO: 908:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 908:

ACAGGCTGGG                                                              10

(2) INFORMATION FOR SEQ ID NO: 909:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 909:

CAGGCTGGGC                                                              10

(2) INFORMATION FOR SEQ ID NO: 910:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 910:

GGCGGCCTGG AAAGCTGAGA TGGAGGGCGG CATGGCGGGC ACAGGCTGGG C                 51

(2) INFORMATION FOR SEQ ID NO: 911:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 911:

GCGGCCTGGA AAGCTGAGAT GGAGGGCGGC ATGGCGGGCA CAGGCTGGGC        50

(2) INFORMATION FOR SEQ ID NO: 912:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 912:

CGGCCTGGAA AGCTGAGATG GAGGGCGGCA TGGCGGGCAC AGGCTGGGC         49

(2) INFORMATION FOR SEQ ID NO: 913:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 913:

GGCCTGGAAA GCTGAGATGG AGGGCGGCAT GGCGGGCACA GGCTGGGC          48

(2) INFORMATION FOR SEQ ID NO: 914:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 914:

GCCTGGAAAG CTGAGATGGA GGGCGGCATG GCGGGCACAG GCTGGGC           47

(2) INFORMATION FOR SEQ ID NO: 915:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 915:

CCTGGAAAGC TGAGATGGAG GCGGCATGG CGGGCACAGG CTGGGC             46

(2) INFORMATION FOR SEQ ID NO: 916:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 916:

CTGGAAAGCT GAGATGGAGG GCGGCATGGC GGGCACAGGC TGGGC             45

(2) INFORMATION FOR SEQ ID NO: 917:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 917:

TGGAAAGCTG AGATGGAGGG CGGCATGGCG GGCACAGGCT GGGC                  44

(2) INFORMATION FOR SEQ ID NO: 918:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 918:

GGAAAGCTGA GATGGAGGGC GGCATGGCGG GCACAGGCTG GGC                    43

(2) INFORMATION FOR SEQ ID NO: 919:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 919:

GAAAGCTGAG ATGGAGGGCG GCATGGCGGG CACAGGCTGG GC                     42

(2) INFORMATION FOR SEQ ID NO: 920:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 920:

AAAGCTGAGA TGGAGGGCGG CATGGCGGGC ACAGGCTGGG C                      41

(2) INFORMATION FOR SEQ ID NO: 921:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 921:

AAGCTGAGAT GGAGGGCGGC ATGGCGGGCA CAGGCTGGGC                       40

(2) INFORMATION FOR SEQ ID NO: 922:

```
    (i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 922:

AGCTGAGATG GAGGGCGGCA TGGCGGGCAC AGGCTGGGC                              39

(2) INFORMATION FOR SEQ ID NO: 923:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 923:

GCTGAGATGG AGGGCGGCAT GGCGGGCACA GGCTGGGC                               38

(2) INFORMATION FOR SEQ ID NO: 924:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 924:

CTGAGATGGA GGGCGGCATG GCGGGCACAG GCTGGGC                                37

(2) INFORMATION FOR SEQ ID NO: 925:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 925:

TGAGATGGAG GCGGCATGG CGGGCACAGG CTGGGC                                  36

(2) INFORMATION FOR SEQ ID NO: 926:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 926:

GAGATGGAGG CGGCATGGC GGGCACAGGC TGGGC                                   35

(2) INFORMATION FOR SEQ ID NO: 927:

(i) SEQUENCE CHARACTERISTICS:
        (A) LENGTH: 34 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO: 927:

AGATGGAGGG CGGCATGGCG GGCACAGGCT GGGC                                      34

(2) INFORMATION FOR SEQ ID NO: 928:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 928:

GATGGAGGGC GGCATGGCGG GCACAGGCTG GGC                                       33

(2) INFORMATION FOR SEQ ID NO: 929:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 929:

ATGGAGGGCG GCATGGCGGG CACAGGCTGG GC                                        32

(2) INFORMATION FOR SEQ ID NO: 930:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 930:

TGGAGGGCGG CATGGCGGGC ACAGGCTGGG C                                         31

(2) INFORMATION FOR SEQ ID NO: 931:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 931:

GGAGGGCGGC ATGGCGGGCA CAGGCTGGGC                                           30

(2) INFORMATION FOR SEQ ID NO: 932:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: DNA (genomic)

-continued (xi) SEQUENCE DESCRIPTION: SEQ ID NO: 932:

GAGGGCGGCA TGGCGGGCAC AGGCTGGGC                                29

(2) INFORMATION FOR SEQ ID NO: 933:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 933:

AGGGCGGCAT GGCGGGCACA GGCTGGGC                                 28

(2) INFORMATION FOR SEQ ID NO: 934:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 934:

GGGCGGCATG GCGGGCACAG GCTGGGC                                  27

(2) INFORMATION FOR SEQ ID NO: 935:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 935:

GGCGGCATGG CGGGCACAGG CTGGGC                                   26

(2) INFORMATION FOR SEQ ID NO: 936:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 936:

GCGGCATGGC GGGCACAGGC TGGGC                                    25

(2) INFORMATION FOR SEQ ID NO: 937:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 937:

CGGCATGGCG GCACAGGCT GGGC                                      24

(2) INFORMATION FOR SEQ ID NO: 938:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 938:

GGCATGGCGG GCACAGGCTG GGC                                            23

(2) INFORMATION FOR SEQ ID NO: 939:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 939:

GCATGGCGGG CACAGGCTGG GC                                             22

(2) INFORMATION FOR SEQ ID NO: 940:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 940:

CATGGCGGGC ACAGGCTGGG C                                              21

(2) INFORMATION FOR SEQ ID NO: 941:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 941:

ATGGCGGGCA CAGGCTGGGC                                                20

(2) INFORMATION FOR SEQ ID NO: 942:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 942:

TGGCGGGCAC AGGCTGGGC                                                 19

(2) INFORMATION FOR SEQ ID NO: 943:

(i) SEQUENCE CHARACTERISTICS:

```
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 943:

GGCGGGCACA GGCTGGGC                                              18

(2) INFORMATION FOR SEQ ID NO: 944:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 944:

GCGGGCACAG GCTGGGC                                               17

(2) INFORMATION FOR SEQ ID NO: 945:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 945:

CGGGCACAGG CTGGGC                                                16

(2) INFORMATION FOR SEQ ID NO: 946:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 946:

GGGCACAGGC TGGGC                                                 15

(2) INFORMATION FOR SEQ ID NO: 947:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 947:

GGCACAGGCT GGGC                                                  14

(2) INFORMATION FOR SEQ ID NO: 948:

(i) SEQUENCE CHARACTERISTICS:
        (A) LENGTH: 13 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 948:

GCACAGGCTG GGC                                                              13

(2) INFORMATION FOR SEQ ID NO: 949:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 949:

CACAGGCTGG GC                                                               12

(2) INFORMATION FOR SEQ ID NO: 950:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 950:

ACAGGCTGGG C                                                                11

(2) INFORMATION FOR SEQ ID NO: 951:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 951:

CAGGCTGGGC                                                                  10

(2) INFORMATION FOR SEQ ID NO: 952:

(i) SEQUENCE CHARACTERISTICS:
         (A) LENGTH: 9 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 952:

AGGCTGGGC                                                                    9

(2) INFORMATION FOR SEQ ID NO: 953:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 953:

```
TTT TCC TTC CTT TGT CTC TCT TC                              23
```

(2) INFORMATION FOR SEQ ID NO: 954:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 954:

```
GCT CCC GGC TGC CTG                                         15
```

(2) INFORMATION FOR SEQ ID NO: 955:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 955:

```
CTC GGC CGT GCG GCT CTG TCG CTC CCG GT                      29
```

(2) INFORMATION FOR SEQ ID NO: 956:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 956:

```
CCG CCG CCC TCC GGG GGG TC                                  20
```

(2) INFORMATION FOR SEQ ID NO: 957:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 957:

```
TGC TGC CGT TGG CTG CCC                                     18
```

(2) INFORMATION FOR SEQ ID NO: 958:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 958:

```
CTT CTG CGG GTC GCC GG                                      17
```

(2) INFORMATION FOR SEQ ID NO: 959:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 959:

TGC TGG GCT TGT GGC     15

(2) INFORMATION FOR SEQ ID NO: 960:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 960:

GGC CTC TCT TCT GGG     15

(2) INFORMATION FOR SEQ ID NO: 961:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 961:

CCT GGT CCC TCC GT     14

(2) INFORMATION FOR SEQ ID NO: 962:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 962:

GGT GGC TCC TCT GC     14

(2) INFORMATION FOR SEQ ID NO: 963:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 963:

GCT TGG TCC TGG GGC TGC     18

(2) INFORMATION FOR SEQ ID NO: 964:

(i) SEQUENCE CHARACTERISTICS:
        (A) LENGTH: 15 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 964:

TGC TCT CCT CTC CTT                                                     15

(2) INFORMATION FOR SEQ ID NO: 965:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 965:

TGC TTT TCT TTT CTG GGC CTC                                             21

(2) INFORMATION FOR SEQ ID NO: 966:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 966:

TGT GGT CTG TTT TTT TCT G                                               19

(2) INFORMATION FOR SEQ ID NO: 967:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 967:

GCC CTG CTG GGG CGC TCT CC                                              20

(2) INFORMATION FOR SEQ ID NO: 968:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 968:

GCC GCC CGC CTG GCT CCC                                                 18

(2) INFORMATION FOR SEQ ID NO: 969:

(i) SEQUENCE CHARACTERISTICS:
        (A) LENGTH: 21 base pairs
        (B) TYPE: nucleic acid
        (C) STRANDEDNESS: single
        (D) TOPOLOGY: linear

```
            (ii) MOLECULE TYPE: DNA (genomic)

(xi) SEQUENCE DESCRIPTION: SEQ ID NO: 969:

GGB GCC CBT GBT GGG CBT GCC                                                 21

(2) INFORMATION FOR SEQ ID NO: 970:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 970:

GTG GTT CTT GCC CTC CTT TGG CTG                                             24

(2) INFORMATION FOR SEQ ID NO: 971:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 971:

CCG TGC CCG CTC CCC GGC                                                     18

(2) INFORMATION FOR SEQ ID NO: 972:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 972:

CTC CTG GCG GGT GGC CGT TG                                                  20

(2) INFORMATION FOR SEQ ID NO: 973:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 973:

GGC CCG TGT TCC CCT GGG                                                     18

(2) INFORMATION FOR SEQ ID NO: 974:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 974:
```

```
GCC TGG GGC TCC CTT CTC TC                                    20

(2) INFORMATION FOR SEQ ID NO: 975:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 975:

GCC CTT CTT GCT GGG CCT C                                     19

(2) INFORMATION FOR SEQ ID NO: 976:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 976:

TGC TGC TGC TGG TGC TGT GGC CCC C                             25

(2) INFORMATION FOR SEQ ID NO: 977:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 977:

GTA CAC CGA GGA GCC CAT GAT GGG CAT GCC ACA GAC GAC AGG C     43

(2) INFORMATION FOR SEQ ID NO: 978:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 978:

GTB CBC CGB GGB GCC CBT GBT GGG CBT GCC BCB GBC GBC BGG C     43

(2) INFORMATION FOR SEQ ID NO: 979:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 979:

GGC GCC GTG CCG CGT CTT GGT GGC GGC GG                        29

(2) INFORMATION FOR SEQ ID NO: 980:
```

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 980:

GTT CGC GCC CGC GCG GGG CCC CTC CGG TCC                            30

(2) INFORMATION FOR SEQ ID NO: 981:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 981:

TTG GCC CGC GCG CCC GCC CGT CTC GGG CTG GGC GG                     35

(2) INFORMATION FOR SEQ ID NO: 982:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 982:

CGG GTC GGG GCC CCC CGC GGC C                                      22

(2) INFORMATION FOR SEQ ID NO: 983:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 983:

GCC TCG GGG CTG GGG CGC TGG TGG CCG GG                             29

(2) INFORMATION FOR SEQ ID NO: 984:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 984:

CCG CGC CTC CGC CTG CCG CTT CTG                                    24

(2) INFORMATION FOR SEQ ID NO: 985:

(i) SEQUENCE CHARACTERISTICS:
        (A) LENGTH: 21 base pairs
        (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO: 985:

GCT GGG CCC CGG GCG CCC CCT                                         21

(2) INFORMATION FOR SEQ ID NO: 986:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 986:

CCC CTC TTG CTC GGG TCC CCG TG                                      23

(2) INFORMATION FOR SEQ ID NO: 987:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 987:

ACA GCG CGT CCT GTG TCT CCA GCA GCA TGG CCG GGC CAG CTG GGC CCC     48

(2) INFORMATION FOR SEQ ID NO: 988:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 988:

BCB GCG CGT CCT GTG TCT CCB GCB GCB TGG CCG GGC CBG CTG GGC CCC     48

(2) INFORMATION FOR SEQ ID NO: 989:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 989:

ACA GAG CAT GCT GTT GTT GGG CAT CTT GCC TTC CCA GGG                 39

(2) INFORMATION FOR SEQ ID NO: 990:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)
```

-continued

```
    (xi) SEQUENCE DESCRIPTION: SEQ ID NO: 990:

BCB GBG CBT GCT GTT GTT GGG CBT CTT GCC TTC CCB GGG                    39

(2) INFORMATION FOR SEQ ID NO: 991:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 991:

CCC TTT TCT GGT GGG GTG                                                18

(2) INFORMATION FOR SEQ ID NO: 992:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 992:

GTG CTG TTG TTG GGC                                                    15

(2) INFORMATION FOR SEQ ID NO: 993:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 993:

TTT CTT CTG TTC CC                                                     14

(2) INFORMATION FOR SEQ ID NO: 994:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 994:

CCC TTT TCT GGT GGG GTG                                                18

(2) INFORMATION FOR SEQ ID NO: 995:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 995:

GTG CTG TTG TTG GGC                                                    15
```

(2) INFORMATION FOR SEQ ID NO: 996:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 996:

TTT CTT CTG TTC CC        14